(12) United States Patent
Redshaw et al.

(10) Patent No.: US 12,138,076 B2
(45) Date of Patent: Nov. 12, 2024

(54) ORAL APPLIANCE

(71) Applicant: SPORTS & WELL BEING ANALYTICS LIMITED, Swansea (GB)

(72) Inventors: Nicholas Andrew Redshaw, Swansea (GB); William Stephen Powell, Swansea (GB); Jonathan Michael William Cassidy, Swansea (GB)

(73) Assignee: SPORTS & WELL BEING ANALYTICS LIMITED, Swansea (GB)

( * ) Notice: Subject to any disclaimer, the term of this patent is extended or adjusted under 35 U.S.C. 154(b) by 1012 days.

(21) Appl. No.: 16/986,848

(22) Filed: Aug. 6, 2020

(65) Prior Publication Data

US 2020/0367821 A1 Nov. 26, 2020

Related U.S. Application Data

(63) Continuation of application No. PCT/GB2019/050325, filed on Feb. 6, 2019.

(30) Foreign Application Priority Data

Feb. 6, 2018 (GB) .................................... 1801914
Oct. 12, 2018 (GB) .................................... 1816668
(Continued)

(51) Int. Cl.
*A61B 5/00* (2006.01)
*A61B 5/01* (2006.01)
(Continued)

(52) U.S. Cl.
CPC ............ *A61B 5/682* (2013.01); *A61B 5/0002* (2013.01); *A61B 5/01* (2013.01); *A61B 5/11* (2013.01);
(Continued)

(58) Field of Classification Search
CPC ......... A61B 5/682; A61B 5/0002; A61B 5/01; A61B 5/11; A61B 5/14546; A61B 5/4875;
(Continued)

(56) References Cited

U.S. PATENT DOCUMENTS 5,490,520 A * 2/1996 Schaefer ................. A61F 5/566
128/848
10,278,644 B1 * 5/2019 Etzkorn ............... A61B 5/6821
(Continued)

FOREIGN PATENT DOCUMENTS

CA 3167546 A1 * 8/2021 ......... A61B 5/14551
CN 106056848 A 10/2016
(Continued)

OTHER PUBLICATIONS

International Search Report dated May 23, 2019 from corresponding International Patent Application No. PCT/GB2019/050325, 5 pages.
(Continued)

*Primary Examiner* — Tarla R Patel
(74) *Attorney, Agent, or Firm* — Ruggiero McAllister & McMahon LLC

(57) ABSTRACT

The mouth-guard, includes a body with a formation for extending around a portion of at least one of maxillary and mandibular teeth of a wearer and located against a portion of at least one of maxillary and mandibular teeth and at least at one of: an anterior teeth region of the wearer; a posterior teeth region of the wearer; and a position between the anterior and posterior teeth regions of the wearer. The mouth-guard includes a system for monitoring the mouth-guard's acceleration and communicates acceleration data to a monitoring station, and a power source for monitoring acceleration. The power source is embedded within the body
(Continued)

and is located within a region that is at a posterior teeth region of the wearer. The system for monitoring acceleration is embedded within the body and is located within a region that is at a posterior teeth region of the wearer.

12 Claims, 18 Drawing Sheets

(30) Foreign Application Priority Data

Nov. 5, 2018 (GB) ...................................... 1818054
Feb. 6, 2019 (GB) ...................................... 1901654

(51) Int. Cl.
    *A61B 5/11*     (2006.01)
    *A61B 5/145*     (2006.01)
    *A63B 71/08*     (2006.01)
    *G06F 1/3203*     (2019.01)
    *G08C 17/02*     (2006.01)
    *G16H 40/67*     (2018.01)

(52) U.S. Cl.
    CPC ........ *A61B 5/14546* (2013.01); *A61B 5/4875* (2013.01); *A63B 71/085* (2013.01); *G06F 1/3203* (2013.01); *G08C 17/02* (2013.01); *G16H 40/67* (2018.01); *A61B 2503/10* (2013.01); *A61B 2560/0214* (2013.01); *A61B 2562/0219* (2013.01); *A63B 2209/00* (2013.01)

(58) Field of Classification Search
    CPC ........ A61B 2503/10; A61B 2560/0214; A61B 2562/0219; A61B 5/6803; A63B 71/085; A63B 2209/00; A63B 2220/40; A63B 2230/50; A63B 2220/53; G06F 1/3203; G08C 17/02; G16H 40/67; G16H 20/30; G16H 40/63
    See application file for complete search history.

(56) References Cited

U.S. PATENT DOCUMENTS

| | | | |
|---|---|---|---|
| 11,684,314 B2* | 6/2023 | Stitzel, Jr. .............. | A61B 5/682 600/595 |
| 2006/0233200 A1 | 10/2006 | Fifield et al. | |
| 2009/0017422 A1* | 1/2009 | Creamer .............. | A61C 19/066 433/215 |
| 2012/0172679 A1* | 7/2012 | Logan .................. | A61B 5/6803 600/301 |
| 2012/0304767 A1 | 12/2012 | Howard et al. | |
| 2013/0211270 A1* | 8/2013 | St. Laurent ............ | A61B 5/682 600/595 |
| 2014/0187875 A1* | 7/2014 | Paris ...................... | A61B 5/682 600/595 |
| 2014/0188010 A1 | 7/2014 | Paris et al. | |
| 2014/0257051 A1* | 9/2014 | Cam .................... | A61B 5/0004 600/595 |
| 2014/0357392 A1 | 12/2014 | Goel et al. | |
| 2015/0119759 A1* | 4/2015 | Gonzales ............... | A61B 5/682 600/595 |
| 2015/0173666 A1 | 6/2015 | Smith et al. | |
| 2015/0305671 A1* | 10/2015 | Yoon ....................... | A61B 5/01 600/28 |
| 2015/0374274 A1 | 12/2015 | Jovanovski | |
| 2016/0242692 A1 | 8/2016 | McAuliffe et al. | |
| 2016/0325143 A1 | 11/2016 | Yuen et al. | |
| 2017/0095204 A1* | 4/2017 | Stitzel, Jr. .............. | A61B 5/682 |
| 2017/0156635 A1* | 6/2017 | Kuo ....................... | A61B 5/682 |
| 2017/0238850 A1 | 8/2017 | Gonzales et al. | |
| 2017/0291081 A1 | 10/2017 | Hirabgayashi | |

FOREIGN PATENT DOCUMENTS

| | | | | |
|---|---|---|---|---|
| JP | 2012-147280 A | | 8/2012 | |
| WO | WO-2011153175 A1 | * | 12/2011 | .......... A63B 71/085 |
| WO | 2014/110548 A1 | | 7/2014 | |
| WO | 2015/061710 A1 | | 4/2015 | |
| WO | 2017/070343 A1 | | 4/2017 | |
| WO | WO-2018172409 A1 | * | 9/2018 | .......... A61B 5/4519 |
| WO | WO-2019155209 A1 | * | 8/2019 | .......... A61B 5/0002 |

OTHER PUBLICATIONS

Written Opinion dated May 23, 2019 from corresponding International Patent Application No. PCT/GB2019/050325, 7 pages.
GB Search Report dated Jul. 16, 2018 from corresponding GB Patent Application No. GB1801914.1, 2 pages.
GB Search Report dated Apr. 12, 2019 from corresponding GB Patent Application No. GB1818054.7, 2 pages.
GB Search Report dated Aug. 1, 2019 from corresponding GB Patent Application No. GB1901654.2, 2 pages.
GB Search Report dated Apr. 11, 2019 from corresponding GB Patent Application No. GB1816668.6, 2 pages.

* cited by examiner

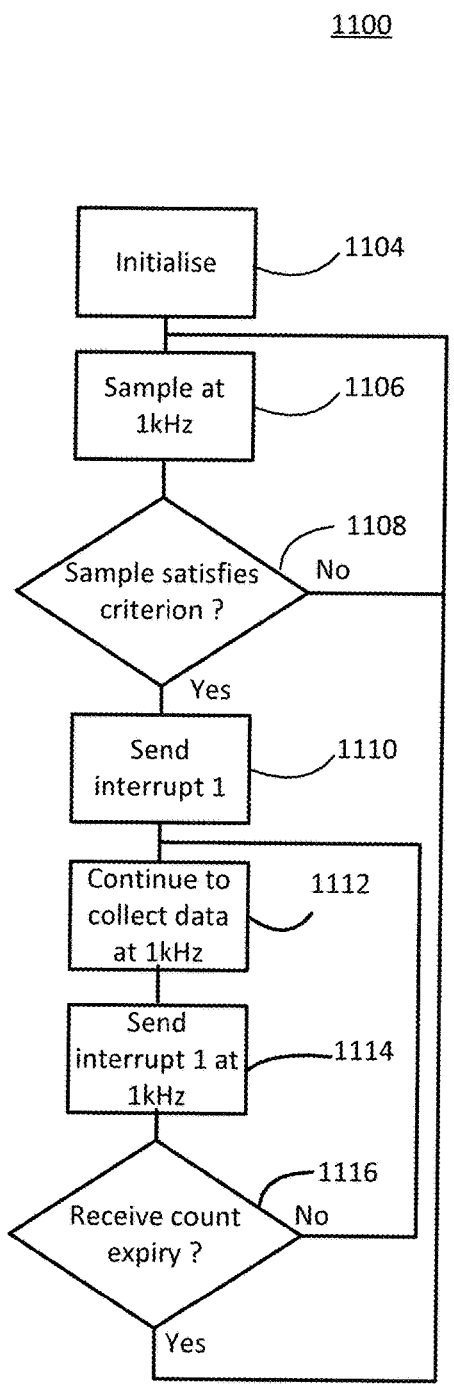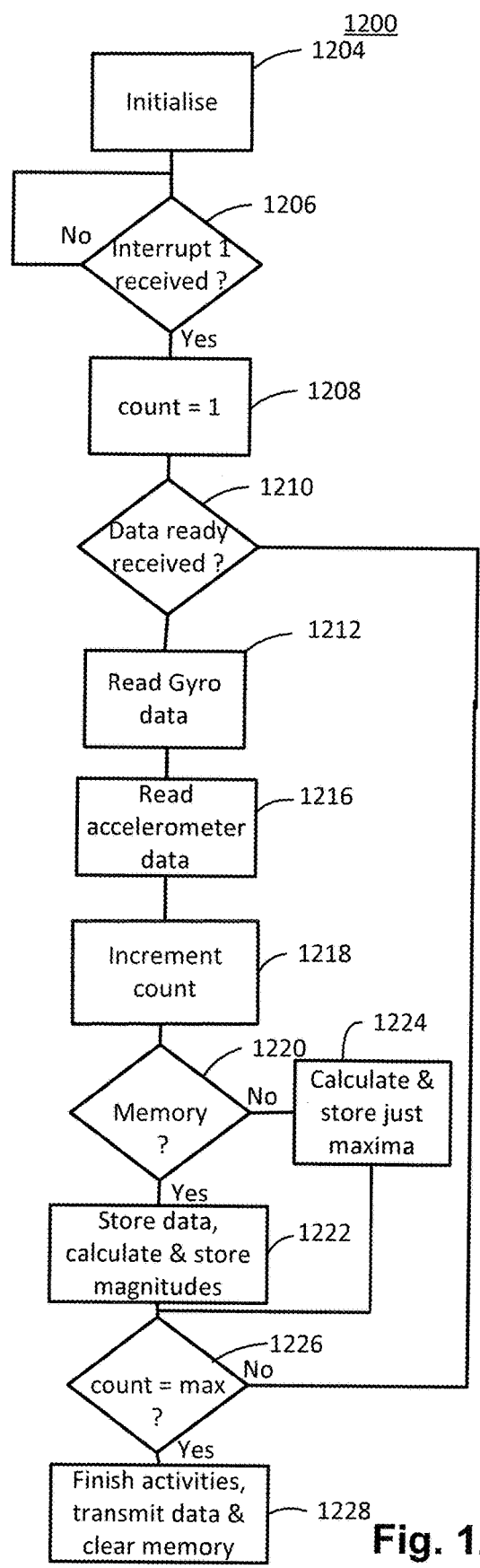
Fig. 11
Fig. 12

ORAL APPLIANCE

CROSS REFERENCE TO RELATED APPLICATIONS

This application claims the benefit under 35 U.S.C. § 119(a) of United Kingdom Application No. 1801914.1 filed Feb. 6, 2018, United Kingdom Application No. 1816668.6 filed Oct. 12, 2018, United Kingdom Application No. 1818054.7 filed Nov. 5, 2018, United Kingdom Application No. 1901654.2 filed Feb. 6, 2019, and is a continuation of International Application number PCT/GB2019/050325 filed Feb. 6, 2019, the contents of each which are incorporated by reference herein in their entirety.

BACKGROUND OF THE DISCLOSURE

1. Field of the Disclosure

The present disclosure relates to an oral appliance for monitoring impacts to a wearer and particularly, but not exclusively, to a mouth-guard for wear by a participant in a contact sport.

2. Description of the Related Art

Participants in sports, particularly contact sports, such as, for example, Rugby Football, American (NFL) Football, Boxing, Mixed martial arts (MMA), etc., and particularly professional participants in sports, receive impacts from collisions with other participants during match play. These impacts may be, and often are, heavy, violent impacts and may include direct head impacts. A head of the participant receiving such a heavy impact may be moved violently and be subject to great accelerative forces, termed hereinafter "head impact event." While an individual head impact event may not cause a concussion event of its own effect, the effect of such violent movements can be cumulative. Therefore, when a participant has sustained a critical number of violent head movements over a certain period it is advisable to prevent the participant from playing in further games to reduce the risk of the participant being exposed to the chance of a potential serious head injury event, for example, one that might cause concussion, or further concussion, or other serious injury. It is possible to monitor impacts sustained by participants, not only during individual matches, but also over the course of their careers so that a medical team or coach, for example, can be made aware of the situation. A participant may be advised as to when they should next play or train.

Historically, it has been difficult to monitor head impact events, particularly the linear and rotational acceleration and forces actually encountered by a participant during a game. One method used to date in professional games has involved a "spotter" for each participant. The "spotter" typically may be located in the audience at the sporting event, or may be viewing the sporting event remotely via a video link. Each "spotter" is tasked with monitoring impacts, or blows, received by their assigned participant. If the "spotter" observes an impact event that they deem to be a head impact event, they can coordinate the stoppage of play in order to remove their assigned participant from the field-of-play to be assessed by a qualified medical practitioner. However, such assessment is, generally, subjective and does not provide an accurate indication of the forces sustained, which may be different for each participant involved in a collision leading to one or more head impact events. Furthermore, it is highly expensive, because personnel may be required for each participant on the field-of-play. Additionally, such a monitoring environment is generally not available in amateur-level contact sports matches and thus amateur sportsmen are not afforded the same level of monitoring for head impact events as their professional counterparts.

In an attempt to objectively measure the accelerations or forces sustained by a participant, it has been suggested to use monitoring units, to be worn by the participant. Such monitoring units include sensors, for example inertial measurement units, which operate to monitor acceleration experienced by a wearer during the course of match play. Data produced by the sensors of the monitoring units can be stored in an on-board memory and/or transmitted to a monitoring station for review by a technician. However, use of such monitoring units, particularly in professional games, may be prohibited under the regulations of certain sports, because the regulations prohibit the attachment of solid objects to the outside of a body of the participant (i.e. either worn by the participant or worn in the clothing of the participant).

In addition, there has been resistance from participants who are reluctant to adopt the use of such monitoring units. This may stem from a concern that their careers may be ended prematurely if they are involved in what is assessed to be too many head impact events. It is therefore desirable that any system developed to address the problems of low adoption rates and reducing subjectivity in assessments can accurately measure the accelerations sustained to try to reduce instances of false positives, and possibly lengthen a playing career otherwise shortened due to the inaccuracy and procedures associated with conventional approaches.

One type of known monitoring unit comprises an adhesive-backed unit, which allows for mounting of the unit behind an ear of a participant. The unit is operative to monitor for head impact events. However, measured impact readings from such units can vary extensively, depending on the location of the sensor behind the ear, which puts into question the accuracy of the measurements. Furthermore, as discussed above, use of such devices in professional games are prohibited.

Another type of known monitoring unit comprises a unit integrated with, or embedded in, a helmet (e.g. as used in American Football). Again this type of unit is operative to monitor for head impact events during match play. However, as the helmets may move relative to the head during an impact event the measurements may be inaccurate and may not provide an accurate indication of whether or not a head impact event has occurred. In addition, such a system is suitable only for sports like American Football where helmets are used and is not suitable for other sports such as, for example, Rugby Football.

A further known type of monitoring unit comprises a mouth-guard or gum-shield (hereinafter "mouth-guard") embedded with sensors. Such types of units have been increasingly adopted, because they are worn within a mouth of the participant (and so their use is unlikely to be prohibited by the regulation of many sports, because they are not worn outside the body). Furthermore, they are seen as potentially more accurate than external units worn on the body, or located in helmets, because they may measure more accurately the sustained acceleration by a participant due to an impact on the participant (from which acceleration an impact force can be derived). This is because they are typically worn against teeth of the upper jaw, and since the upper jaw is a fixed part of the head (as opposed to the lower jaw, which is moveable relative to the rest of the head), will move with the head. Therefore, the unit will typically undergo the same movement during an impact event (and experience the same forces and accelerations) as that experienced by the head itself. Such units are seen to be beneficial, because no adhesions of sensors to the head or neck of the participant are required.

In many of these mouth-guard types of units, the monitoring sensors are located in a portion of the mouth-guard that is locatable against an outer surface of the upper teeth of the participant. This is to ensure that a data signal transmitted by the unit to a monitoring station does not suffer interference, or attenuation, that may be caused by having to pass through the teeth. Locating at least the transceiver element of such units in an outer portion of the mouth-guard may reduce, or inhibit, these issues.

Concerning another aspect, participants in sports, particularly contact sports, such as, for example, Rugby Football, American (NFL) Football, Boxing, Mixed Martial Arts (MMA), Association Football (soccer) etc., and particularly professional participants in sports, receive impacts from collisions with other participants during match play. These impacts may be, and often are, heavy, violent impacts and may include direct head impacts. A head of the participant receiving such a heavy impact may be moved violently and be subject to great accelerative forces, termed hereinafter "head impact event." While an individual head impact event may not cause a concussion event of its own effect, the effect of such violent movements can be cumulative. Therefore, when a participant has sustained a critical number of violent head movements over a certain period it is advisable to prevent the participant from playing in further games to reduce the risk of the participant being exposed to the chance of a potential serious head injury event, for example, one that might cause concussion, or further concussion, or other serious injury. It is possible to monitor impacts sustained by participants, not only during individual matches, but also over the course of their careers so that a medical team or coach, for example, can be made aware of the situation. A participant may be advised as to when they should next play or train.

Historically, it has been difficult to monitor head impact events, particularly the linear and rotational acceleration and forces actually encountered by a participant during a game. One method used to date in professional games has involved a "spotter" for each participant. The "spotter" typically may be located in the audience at the sporting event, or may be viewing the sporting event remotely via a video link. Each "spotter" is tasked with monitoring impacts, or blows, received by their assigned participant. If the "spotter" observes an impact event that they deem to be a head impact event, they can coordinate the stoppage of play in order to remove their assigned participant from the field-of-play to be assessed by a qualified medical practitioner. However, such assessment is, generally, subjective and does not provide an accurate indication of the forces sustained, which may be different for each participant involved in a collision leading to one or more head impact events. Furthermore, it is highly expensive, because personnel may be required for each participant on the field-of-play. Additionally, such a monitoring environment is generally not available in amateur-level contact sports matches and thus amateur sportsmen are not afforded the same level of monitoring for head impact events as their professional counterparts.

In an attempt to objectively measure the accelerations or forces sustained by a participant, it has been suggested to use monitoring units, to be worn by the participant. Such monitoring units include sensors, for example inertial measurement units, which operate to monitor acceleration experienced by a wearer during the course of match play. Data produced by the sensors of the monitoring units can be stored in an on-board memory and/or transmitted to a monitoring station for review by a technician. However, use of such monitoring units, particularly in professional games, may be prohibited under the regulations of certain sports, because the regulations prohibit the attachment of solid objects to the outside of a body of the participant (i.e. either worn by the participant or worn in the clothing of the participant).

In addition, there has been resistance from participants who are reluctant to adopt the use of such monitoring units. This may stem from a concern that their careers may be ended prematurely if they are involved in what is assessed to be too many head impact events. It is therefore desirable that any system developed to address the problems of low adoption rates and reducing subjectivity in assessments can accurately measure the accelerations sustained to try to reduce instances of false positives, and possibly lengthen a playing career otherwise shortened due to the inaccuracy and procedures associated with conventional approaches.

One type of known monitoring unit comprises an adhesive-backed unit, which allows for mounting of the unit behind an ear of a participant. The unit is operative to monitor for head impact events. However, measured impact readings from such units can vary extensively, depending on the location of the sensor behind the ear, which puts into question the accuracy of the measurements. Furthermore, as discussed above, use of such devices in professional games are prohibited.

Another type of known monitoring unit comprises a unit integrated with, or embedded in, a helmet (e.g. as used in American Football). Again this type of unit is operative to monitor for head impact events during match play. However, as the helmets may move relative to the head during an impact event the measurements may be inaccurate and may not provide an accurate indication of whether or not a head impact event has occurred. In addition, such a system is suitable only for sports like American Football where helmets are used and is not suitable for other sports such as, for example, Rugby Football.

A further known type of monitoring unit comprises a removable intra oral appliance such as a mouth-guard or gum-shield (hereinafter "mouth-guard") embedded with sensors. Such types of units have been increasingly adopted, because they are worn within a mouth of the participant (and so their use is unlikely to be prohibited by the regulation of many sports, because they are not worn outside the body). Furthermore, they are seen as potentially more accurate than external units worn on the body, or located in helmets, because they may measure more accurately the sustained acceleration by a participant due to an impact on the participant (from which acceleration an impact force can be derived). This is because they are typically worn against teeth of the upper jaw, and since the upper jaw is a fixed part of the head (as opposed to the lower jaw, which is moveable relative to the rest of the head), will move with the head. Therefore, the unit will typically undergo the same movement during an impact event (and experience the same forces and accelerations) as that experienced by the head itself. Such units are seen to be beneficial, because no adhesions of sensors to the head or neck of the participant are required.

Known devices such as disclosed in US2015119759, US2017238850 and US2011179852 utilise impact severity indicators to indicate if an impact event causes an acceleration sensor to experience an acceleration that exceeds an acceleration threshold. There may be two thresholds, one for a low level severity impact event and higher threshold indicative of a more severe impact event.

In many of these mouth-guard types of units, the monitoring sensors are located in a portion of the mouth-guard that is locatable against an outer surface of the upper teeth of the participant. This is to ensure that a data signal transmitted by the unit to a monitoring station does not suffer interference, or attenuation, that may be caused by having to pass through the teeth. Locating at least the transceiver element of such units in an outer portion of the mouth-guard may reduce, or inhibit, these issues.

Matches and training during which a mouth-guard may be used may extend over significant time periods during which the detection of acceleration takes place. In a match environment, the time period may be uncertain due to stoppages of play and access to a participant to change a mouth-guard due to running out of power may be limited. The power unit for the monitoring unit will be of a size suitable to be worn by the participant, typically within the mouth-guard itself, and therefore likely to be small and of limited capacity. Should the power unit for the mouth-guard run out of power or have insufficient power to operate reliably then it may not be able to detect acceleration and therefore possibly not alert medical staff and or coaches to a head impact event relevant to the health and well-being of the participant and which may be sufficient for a head impact assessment to be undertaken.

Concerning still another aspect, participants in sports, particularly contact sports, such as, for example, Rugby Football, American (NFL) Football, Boxing, Mixed martial arts (MMA), Association Football (soccer), etc., and particularly professional participants in sports, receive impacts from collisions with other participants during match play. These impacts may be, and often are, heavy, violent impacts and may include direct head impacts. A head of the participant receiving such a heavy impact may be moved violently and be subject to great accelerative forces, termed hereinafter "head impact event." While an individual head impact event may not cause a concussion event of its own effect, the effect of such violent movements can be cumulative. Therefore, when a participant has sustained a critical number of violent head movements over a certain period it is advisable to prevent the participant from playing in further games to reduce the risk of the participant being exposed to the chance of a potential serious head injury event, for example, one that might cause concussion, or further concussion, or other serious injury. It is possible to monitor impacts sustained by participants, not only during individual matches, but also over the course of their careers so that a medical team or coach, for example, can be made aware of the situation. A participant may be advised as to when they should next play or train.

Historically, it has been difficult to monitor head impact events, particularly the linear and rotational acceleration and forces actually encountered by a participant during a game. One method used to date in professional games has involved a "spotter" for each participant. The "spotter" typically may be located in the audience at the sporting event, or may be viewing the sporting event remotely via a video link. Each "spotter" is tasked with monitoring impacts, or blows, received by their assigned participant. If the "spotter" observes an impact event that they deem to be a head impact event, they can coordinate the stoppage of play in order to remove their assigned participant from the field-of-play to be assessed by a qualified medical practitioner. However, such assessment is, generally, subjective and does not provide an accurate indication of the forces sustained, which may be different for each participant involved in a collision leading to one or more head impact events. Furthermore, it is highly expensive, because personnel may be required for each participant on the field-of-play. Additionally, such a monitoring environment is generally not available in amateur-level contact sports matches and thus amateur sportsmen are not afforded the same level of monitoring for head impact events as their professional counterparts.

In an attempt to objectively measure the accelerations or forces sustained by a participant, it has been suggested to use monitoring units, to be worn by the participant. Such monitoring units include sensors, for example inertial measurement units, which operate to monitor acceleration experienced by a wearer during the course of match play. Data produced by the sensors of the monitoring units can be stored in an on-board memory and/or transmitted to a monitoring station for review by a technician. However, use of such monitoring units, particularly in professional games, may be prohibited under the regulations of certain sports, because the regulations prohibit the attachment of solid objects to the outside of a body of the participant (i.e. either worn by the participant or worn in the clothing of the participant).

In addition, there has been resistance from participants who are reluctant to adopt the use of such monitoring units. This may stem from a concern that their careers may be ended prematurely if they are involved in what is assessed to be too many head impact events. It is therefore desirable that any system developed to address the problems of low adoption rates and reducing subjectivity in assessments can accurately measure the accelerations sustained to try to reduce instances of false positives, and possibly lengthen a playing career otherwise shortened due to the inaccuracy and procedures associated with conventional approaches.

One type of known monitoring unit comprises an adhesive-backed unit, which allows for mounting of the unit behind an ear of a participant. The unit is operative to monitor for head impact events. However, measured impact readings from such units can vary extensively, depending on the location of the sensor behind the ear, which puts into question the accuracy of the measurements. Furthermore, as discussed above, use of such devices in professional games are prohibited.

Another type of known monitoring unit comprises a unit integrated with, or embedded in, a helmet (e.g. as used in American Football). Again this type of unit is operative to monitor for head impact events during match play. However, as the helmets may move relative to the head during an impact event the measurements may be inaccurate and may not provide an accurate indication of whether or not a head impact event has occurred. In addition, such a system is suitable only for sports like American Football where helmets are used and is not suitable for other sports such as, for example, Rugby Football.

A further known type of monitoring unit comprises a mouth-guard or gum-shield (hereinafter "mouth-guard") embedded with sensors. Such types of units have been increasingly adopted, because they are worn within a mouth of the participant (and so their use is unlikely to be prohibited by the regulation of many sports, because they are not worn outside the body). Furthermore, they are seen as potentially more accurate than external units worn on the body, or located in helmets, because they may measure more accurately the sustained acceleration by a participant due to an impact on the participant (from which acceleration an impact force can be derived). This is because they are typically worn against teeth of the upper jaw, and since the upper jaw is a fixed part of the head (as opposed to the lower jaw, which is moveable relative to the rest of the head), will move with the head. Therefore, the unit will typically undergo the same movement during an impact event (and experience the same forces and accelerations) as that experienced by the head itself. Such units are seen to be beneficial, because no adhesions of sensors to the head or neck of the participant are required.

In many of these mouth-guard types of units, the monitoring sensors are located in a portion of the mouth-guard that is locatable against an outer surface of the upper teeth of the participant. This is to ensure that a data signal transmitted by the unit to a monitoring station does not suffer interference, or attenuation, that may be caused by having to pass through the teeth. Locating at least the transceiver element of such units in an outer portion of the mouth-guard may reduce, or inhibit, these issues.

Matches and training during which a mouth-guard may be used may extend over significant time periods during which the detection of acceleration takes place. In a match environment, the time period may be uncertain due to stoppages of play and access to a participant to change a mouth-guard due to running out of power may be limited. The power unit for the monitoring unit will be of a size suitable to be worn by the participant, typically within the mouth-guard itself, and therefore likely to be small and of limited capacity. Should the power unit for the mouth-guard run out of power or have insufficient power to operate reliably then it may not be able to detect acceleration and therefore possibly not alert medical staff and or coaches to a head impact event relevant to the health and well-being of the participant and which may be sufficient for a head impact assessment to be undertaken.

Whilst mouth-guards of the types as described above have been satisfactory and may continue to be satisfactory in certain instances, the inventors have recognised that it may be desirable to provide an indication when a charge level of an on-board power source of a mouth-guard becomes low. This may enable appropriate corrective action to be taken, e.g. substituting a mouth-guard having a "low-charge" status with a mouth-guard with a power source having a higher charge level.

In addition to charge level considerations, in an impact assessment system where there is a plurality of mouth-guards, i.e. one per participant on a field of play, the system may operate to collect and monitor impact data from a plurality of mouth-guards. In some environments, data transmissions to send impact data from a mouth-guard to a monitoring station may be interrupted and/or there may be errors in a data transmission.

Data networking and telecommunications systems employ protocols based on positive acknowledgement ("ACK") of receipt of messages, or negative-acknowledgement ("NACK"). In an ACK protocol, receipt of a message is positively acknowledged, i.e. received packets are acknowledged by sending back a packet with an ACK bit set. In a NACK-based protocol, a receiver will only respond to a message if there is a problem, for example, if missing packets are detected in a message received by a receiver, a request is sent for re-transmission of the missing packets.

The inventors have recognised that it may be desirable to provide a system in which a likelihood of impact data obtained by a mouth-guard not reaching a monitoring station is minimized. Missing impact data could result in a potential serious head injury event being overlooked and thus participant welfare could be compromised. Thus, the inventors have recognized that an acknowledgment-based protocol should be employed in the system to reduce the likelihood of impact data not reaching the monitoring station. For the avoidance of doubt, an acknowledgement-based system may include a system which implements a "no-acknowledgement (NACK) protocol" since such a protocol concerns acknowledgements to the extent that it works based on the absence of acknowledgements. However, the inventors have also recognized that the consideration of minimizing the likelihood of impact data not reaching a monitoring station may be a competing consideration to other competing considerations of optimizing available bandwidth and optimizing power source life of on-board power sources on the mouth-guards.

Aspects and embodiments of the present disclosure have been devised with the foregoing in mind.

SUMMARY

According to an aspect of the present disclosure, there is provided an oral appliance, such as a mouth-guard, for detecting acceleration experienced by a head of a wearer, the mouth-guard comprising: a body comprising a formation for surrounding at least a portion of at least one of maxillary and mandibular teeth of a wearer and configured for location against at least a portion of at least one of maxillary and mandibular teeth at least at one of: an anterior teeth region of a mouth of the wearer; a posterior teeth region of a mouth of the wearer; and a position between the anterior and posterior teeth regions of a mouth of the wearer; a system for monitoring acceleration experienced by the mouth-guard and operative to communicate acceleration data to a monitoring station; a power source electrically coupled to the system for monitoring acceleration and for providing power thereto; wherein the power source is embedded within material of the body and is located within a region of the body that is locatable at a posterior teeth region of a mouth of a wearer, and further wherein the system for monitoring acceleration is embedded within the material of the body and is located within a region of the body that is locatable at a posterior teeth region of a mouth of a wearer.

Locating the power source and system for monitoring acceleration in a region of the body that is locatable at a posterior teeth region of a mouth of a wearer results in these components, when the mouth-guard is worn, being located closer to a centre of mass of a head of the wearer and therefore closer to where an acceleration of the brain is experienced. Also, location toward the back of the mouth may inhibit damage to the components because the front of the mouth is typically more vulnerable to experiencing an impact.

Optionally, the formation may comprise a trench in which at least one of maxillary and mandibular teeth of a wearer are locatable, the trench defined by: a first wall configured to cover at least a portion of a vestibular surface of at least one of maxillary and mandibular teeth of a wearer; a second wall configured to cover at least a portion of a palatal surface of at least one of maxillary and mandibular teeth of a wearer; and a third wall connecting the first and second walls and configured to cover at least a portion of incisal and occlusal surfaces of at least one of maxillary and mandibular teeth of a wearer.

Optionally, the power source may be embedded within material of the second wall. Further optionally, the system for monitoring acceleration may be embedded within material of the second wall. Embedding the power source and/or the system for monitoring acceleration within the second wall may further protect one, other, or both, of the power source and system, because the second wall is protected from external impact, in part at least, by the teeth of the wearer.

Optionally, the system for monitoring acceleration may be embedded within material of the first wall.

Optionally, the power source and/or the system for monitoring acceleration may be encapsulated in an inert material. Further optionally, the inert material may comprise parylene C.

Optionally, the power source and/or the system for monitoring acceleration may be encapsulated in material of the body.

Optionally, an antenna of the system for monitoring acceleration may be located remote from the system for monitoring acceleration towards, or at, a region of the formation locatable against an anterior teeth region of the wearer. Further optionally, the antenna may be embedded within the protective material of the first wall.

Optionally, the system for monitoring acceleration and the power source may comprise separate discrete elements. Further optionally, the system for monitoring acceleration and the power source may be electrically connected by a connection lead. Yet further optionally, the connection lead may comprise an antenna of the system for monitoring acceleration.

Optionally, at least one of: dimensions of components of the system for monitoring acceleration; dimensions of a circuit board upon which the system for monitoring acceleration is disposed; an arrangement and/or configuration of components of the system for monitoring acceleration upon a circuit board upon which the system for monitoring acceleration is disposed, may be optimized, and/or reduced, to reduce a volume and/or footprint of the system for monitoring acceleration.

Therefore, by optimizing/reducing the dimensions of the system for monitoring acceleration so as to decrease the foot-print, there will be an increase in the amount of material in contact between the opposed first and second surfaces. As a result, a weakness of the portion of the mouth-guard where the system for monitoring acceleration force is encapsulated may be reduced (includes reduced air pockets and delamination). Thus, instances of failure of this portion during an impact (e.g. when a wearer may clench together the teeth of the upper and lower jaws, thereby increasing pressure on the mouth-guard) may be reduced.

Minimizing the footprint of electronic components of the system for monitoring acceleration and substrates supporting them, e.g. circuit boards, may improve the integrity of the mouth-guard, because the volume of the mouth-guard that is not occupied by material from which the mouth-guard is formed is minimized. In particular, the space between external surfaces (i.e. first and second surfaces) of the wall of the mouth-guard in which the system for monitoring acceleration is encapsulated may be lessened, if the circuit board is smaller. This may improve the creation of a vacuum in the vacuum forming process and thus improve the integrity of the mouth-guard. Specific implementations may include splitting the circuit board up to have smaller circuit board elements. Also, minimizing the footprint of electronic components of the system for monitoring force and substrates supporting them may provide for a more comfortable mouth-guard, because there are smaller deformities (from the electronic components) compared with known types of mouth-guards.

According to another aspect of the present disclosure, there is provided a device for wearing in the mouth for measuring physiological data, the device comprising: a formation for location against at least a portion of at least one maxillary tooth and/or at least one mandibular tooth of a wearer; monitoring circuitry for monitoring physiological data, the monitoring circuitry embedded within material of the formation; and a power source for providing power to the monitoring circuitry, the power source embedded within material of the formation.

Optionally, the device may further comprise a transmitter communicatively coupled to the monitoring circuitry and operative to transmit physiological data received from the monitoring circuitry to a remote device.

Optionally, the device may further comprise a receiver communicatively coupled to the monitoring circuitry and operative to communicate received data from a remote device to the monitoring circuitry.

Optionally, said physiological data may comprise at least one of: hydration; temperature; and electrolyte levels.

According to still another feature of the present disclosure viewed from a first aspect, there is provided a system for monitoring acceleration of an intra oral appliance, comprising:
control circuitry;
a first motion measurement module operative to provide a value representative of motion;
wherein the first motion measurement module is operative in a first mode to provide a first motion value at a first rate and further operative to send a first signal to the control circuitry responsive to a first motion value criterion having been satisfied, and
the control circuitry responsive to the first signal to send a second signal to the first motion measurement module to invoke a second mode operative to sample the first motion value at a second rate greater than or at least equal to the first rate;
the first motion measurement module operative to send a third signal to the control circuitry indicative of a first motion value being available for reading;
the control circuitry responsive to the third signal to initiate a read of a first motion value provided by the first motion measurement module.

Viewed from a second aspect there is provided a method for monitoring acceleration of an intra oral appliance, comprising:
operating a first motion measurement module in a first mode to provide a first motion value at a first rate and to send a first signal to control circuitry responsive to a first motion value criterion having been satisfied, and
operating the control circuitry to respond to the first signal by sending a second signal to the first motion measurement module to invoke a second mode to provide the first motion value at a second rate greater than or equal to the first rate;
operating the first motion measurement module to send a third signal to the control circuitry indicative of a first motion value being available for reading; and
operating the control circuitry to initiate, responsive to the third signal, a read of a of the first motion value provide by the first motion measurement module.

One or more embodiments in accordance with the first and second aspects may be configured and operated so that the first motion measurement module, and one or more other circuitry, may be operated in a low power mode so as to wait for a first motion value satisfying the first motion value criterion. The control circuitry initiating the second rate may cause the first motion measurement module to provide first motion values more often than for the first sample rate and therefore use more power and operate in a higher power usage mode. The control circuitry may be a processor, microcontroller or some other form of programmable digital circuitry and associated processor resources. The third signal may be an interrupt signal and recognised by the control circuitry as a data ready signal. The data rate may be higher by using an interrupt signal as a data ready signal than otherwise would be the case because using an interrupt signal detectable on a falling or rising edge does not require a "settle" time at a low or high voltage state as would be the case if a signal level were used for timing and to initiate or "gate" providing motion data. Thus, more data or a greater density of data may be obtained for an impact event.

A second motion value representative of a second motion may be provided, for example from a second motion measurement module; the control circuitry responsive to the first signal to invoke a second motion measurement mode operative to measure a second motion, for example by sending a fourth signal to the second motion measurement module, and to initiate a read of a second motion value of the second motion measurement module. Thus a second motion may be measured but only when the first motion has satisfied the first motion value criterion.

The control circuitry may be operative in a low power mode pending receipt of the first signal from the first motion measurement module and to invoke a second higher power mode responsive to receipt of the first signal. Thus, an embodiment may be configured to only use such power as is necessary for respective rates.

The control circuitry may be operative to initiate a read of the sample second motion value subsequent to initiating the read of the current first motion value. Thus, there may only be a minimal delay in reading the first and second motion values because the first motion value may be read as soon as the high power mode is initiated and while the second motion measurement module enters its high power mode.

The motion measurement module may be operative such that the second rate is sufficient for the time period between chronologically adjacent third signals to encompass both reading the first motion value of the first motion measurement module and reading the second motion value of the second motion measurement module. Thus, providing a further signal to initiate reading the second motion value may be obviated.

The first motion measurement module may be operative in the second mode for a pre-set time period. Such a pre-set time period may encompass the duration of violent head movement following a head impact event thereby providing motion data for such violent head movement.

Viewed from a third aspect there is provided a system for monitoring acceleration of an intra oral appliance, comprising:
control circuitry;
a first motion measurement module operative to provide a value representative of a first motion;
wherein the first motion measurement module is operative to provide the value representative of the first motion value at a rate;
the first motion measurement module operative to send a first signal to the control circuitry, the control circuitry responsive to the first signal operative to invoke a read mode for reading values representative of a first motion from the first motion measurement module; and
wherein the first motion measurement module is operative to provide the value representative of the first motion at the rate for the control circuitry to read values representative of the first motion from the first motion measurement module for the control signal operative in the read mode.

Viewed from a fourth aspect there is provided a method for monitoring acceleration of an intra oral appliance, comprising:
operating a first motion measurement module to provide a value representative of a first motion at a rate;
operating the first motion measurement module to send a first signal to the control circuitry responsive to the value representative of the first motion satisfying a criterion;
operating the control circuitry to respond to the first signal by invoking a read mode for reading values representative of the first motion from the first motion measurement module;
operating the first motion measurement module to provide the value representative of the first motion at the rate; and
operating the control circuitry to read values representative of the first motion from the first motion measurement module provided at the rate in the read mode.

Such third and fourth aspects provide for the control of the timing of reading first motion values by the first motion measurement module. The control circuitry may be configured to respond to just a small portion of the first signal, e.g. a rising or falling edge such as may be the case for responding to a trigger signal, rather than a longer portion such as a portion exceeding a voltage threshold. Thus, the timing may be more precise as it is based on a rising or falling edge of a signal.

In one or more embodiments the first signal may be sent to the control circuitry at the rate responsive to the value representative of the first motion satisfying the criterion. Continuing to send the first signal at the rate may maximize the rate at which first motion values may be read as it is at the same rate as they are provided by the first motion measurement module. The first signal may be an interrupt signal and recognised by the control circuitry as a data ready signal. The data rate may be higher by using an interrupt signal as a data ready signal than otherwise would be the case because using an interrupt signal detectable on a falling or rising edge does not require a "settle" time at a low or high voltage state as would be the case if a signal level were used for timing and to initiate or "gate" providing motion data. Thus, more data or a greater density of data may be obtained for an impact event.

There may be provided a second motion measurement module operative to provide a value representative of a second motion; the control circuitry responsive to the first signal to read a value representative of a second motion. A second motion measurement module may measure a complementary motion to that of the first motion detection module so that more information about a head impact event for example, may be collected than if just one type of motion was measured. For example, the second motion may be an angular velocity and the first motion may be a linear acceleration In one or more embodiments the control circuitry may be operative in a low power mode pending receipt of the first signal from the first motion measurement module and invokes the read mode at a higher power than the low power mode responsive to receipt of the first trigger signal. Operating the control circuitry in a low power mode until an event to be measured occurs saves on power usage and may provide for a longer operating time of the system.

In one or more embodiments the rate may be sufficient to read the value representative of the first motion value from the first motion measurement module and to read the value representative of the second motion value of the second motion measurement module within one cycle of the rate. Such an arrangement may obviate the need to provide a second timing circuit or arrangement for reading second motion values and links the read rate for the second motion to the read rate for the first motion thereby maintaining the timing relationship between them without the need for synchronising circuitry, mechanisms or the like.

In one or more embodiments control circuitry may be operative in the read mode for a pre-set time period before ceasing the read mode. Setting a pre-set time period obviates having a second criterion to be satisfied by the first motion value (or second motion value) to initiate a halt of the read mode. Suitably, the pre-set time period is based on the typical length of the type of event for which motion is to be measured, e.g. the typical length (or possibly a little longer to avoid missing relevant data) of a head impact event if that is the type of event for which motion is to be measured.

Suitably, the pre-set time period is at least sufficient to read between 70 to 130 first and second motion values, in particular sufficient to read between 85 to 115 first and second motion values, more particularly sufficient to read between 95 to 110 first and second motion values, yet more particularly sufficient for 104 first and second motion values.

In one or more embodiments there may be provided a fifth signal indicative of the sample first motion value satisfying a second first motion value criterion to return to the first mode. Such embodiments implement an approach in which the period for monitoring the event is halted by the first motion value satisfying a second criterion indicative of the event to be measured coming to or approaching an end. For example, the second first motion value criterion may comprise a first motion value less than a peak first motion value provided during the second mode. Such a reduction may be a half value point or some other fraction of the peak value. Thus there is no need to implement a timer to time the start of the event to the end of the pre-set period.

Suitably, the second first motion value criterion may be provided during the second mode which provides for different second first motion value criteria to be provided, for example dependent on some aspect of the first motion values provided.

In one or more embodiments the fifth signal may be internal to the first motion measurement module which reduces the complexity of circuitry for implementing the system.

In one or more embodiments the first motion measurement module may transmit a sixth signal to the control circuitry responsive to the fifth signal to indicate return to the first mode. Thus the control circuitry may invoke a sleep or low power mode to reduce energy usage.

Optionally, the fifth signal may generated in the control circuitry and transmitted to the first motion module to invoke the return to the first mode. Such an arrangement obviates use of a sixth signal.

Typically, the first motion value may comprise respective component first motion values representative of a first motion measured for each of mutually orthogonal directions (X, Y, Z). Likewise, the second motion value may comprise respective component values representative of a second motion measured for each of mutually orthogonal directions (X, Y, Z). Measurement of the motion values in mutually orthogonal directions or planes is useful because a motion may be analyzed in respective directions or planes.

In one or more embodiments, the first motion measurement module is operative to determine a first motion vector from the first motion measured for each of mutually orthogonal directions (X, Y, Z) and provide the first motion vector as the first motion value. Evaluating such a vector takes into account all contributions of motion.

Optionally or additionally in one or more embodiments the first motion measurement module is operative to sample first motion values measured for each of mutually orthogonal directions (X, Y, Z) and provide the sampled first motion values to the control circuitry. Thus, the first motion measurement module may avoid computing the vector sum which may be computed in the control circuitry. This may be particularly synergistic if the control circuitry comprises processor circuitry.

Suitably, the first motion is a linear motion. Measuring linear motion first can be useful because the linear motion may tend to show the most rapid change in the event of an impact event and so is a useful trigger to initiate the read mode.

Suitably, the linear motion is linear acceleration and the first motion measurement module is a linear acceleration measurement module. Linear acceleration is a relatively easy quantity to understand as proportional to force. Typically. the linear acceleration measurement module is an accelerometer.

In one or more embodiments, the second motion is an angular motion measured around respective axes of rotation in mutually orthogonal directions (X', Y', Z'). Such a motion is particularly useful motion if monitoring for a head impact event as the head tends to rotate after the impact.

In particular the motion may be angular velocity and the second motion measurement module an angular velocity measurement module. Although angular acceleration would have to be derived from the angular velocity values, devices to measure angular velocity are readily available.

According to yet another feature of the present disclosure viewed from a first aspect, there is provided a system for monitoring acceleration of an intra oral appliance, comprising:

control circuitry;
a first motion measurement module operative to provide a value representative of a first motion; and
a second motion measurement module operative to provide a second motion value representative of a second motion;
wherein the first motion measurement module is operative in a first mode to provide a first motion value at a first rate and further operative to send a first signal to the control circuitry responsive to a first motion value criterion having been satisfied, and
the control circuitry responsive to the first signal to:
send a second signal to the first motion measurement module to invoke a second mode operative to provide the first motion value at a second rate greater than or at least equal to the first rate; and
send a "wake up" signal to the second motion measurement module to invoke a second motion measurement mode from a low power mode;
the first motion measurement module operative to send a third signal to the control circuitry indicative of a first motion value being available for reading;
the control circuitry responsive to the third signal to initiate a read of a first motion value provided by the first motion measurement module and a read of a second motion value provided by the second motion measurement module.

Viewed from a second aspect there is provided a system for monitoring acceleration of an intra oral appliance, comprising:
- control circuitry;
- a first motion measurement module operative to provide a value representative of a first motion;
- wherein the first motion measurement module is operative to provide the value representative of the first motion value at a rate; and
- a second motion measurement module operative to provide a second motion value representative of a second motion;
- the first motion measurement module operative to send a first signal to the control circuitry responsive to the value representative of the first motion satisfying a criterion, the control circuitry responsive to the first signal to:
  - send a "wake up" signal to the second motion measurement module to invoke a second motion measurement mode operative to provide the second motion value;
  - invoke a read mode for reading values representative of a first motion from the first motion measurement module; and
- wherein the first motion measurement module is operative to provide the value representative of the first motion at the rate for the control circuitry to read values representative of the first motion from the first motion measurement module and read values representative of the second motion value from the second motion measurement module, for the control signal operative in the read mode.

Viewed from a third aspect there is provided a system for monitoring acceleration of an intra oral appliance, comprising:
- control circuitry operative in a first control circuitry low power sleep mode and a second control circuitry higher power normal operation mode;
- a first motion measurement module operative to provide a value representative of a first motion; and
- a second motion measurement module operative to provide a second motion value representative of a second motion;
- wherein the first motion measurement module is operative in a first mode to provide a first motion value at a first rate and further operative to send a first signal to the control circuitry responsive to a first motion value criterion having been satisfied, and
- the control circuitry responsive to the first signal in the first control circuitry mode to:
  - invoke the second control circuitry mode and in the second control circuitry mode;
  - send a second signal to the first motion measurement module to invoke a second mode operative to provide the first motion value at a second rate greater than or at least equal to the first rate; and
    - send a "wake up" signal to the second motion measurement module to invoke a second motion measurement mode from a low power mode;
- the first motion measurement module operative to send a third signal to the control circuitry indicative of a first motion value being available for reading;
- the control circuitry responsive to the third signal to initiate a read of a first motion value provided by the first motion measurement module and a read of a second motion value provided by the second motion measurement module.

Viewed from a fourth aspect there is provided a system for monitoring acceleration of an intra oral appliance, comprising:
- control circuitry operative in a first control circuitry low power sleep mode and a second control circuitry higher power normal operation mode;
- a first motion measurement module operative to provide a value representative of a first motion;
- wherein the first motion measurement module is operative to provide the value representative of the first motion value at a rate; and
- a second motion measurement module operative to provide a second motion value representative of a second motion;
- the first motion measurement module operative to send a first signal to the control circuitry responsive to the value representative of the first motion satisfying a criterion, the control circuitry responsive to the first signal to:
  - invoke the second control circuitry mode and in the second control circuitry mode;
  - invoke a read mode for reading values representative of a first motion from the first motion measurement module; and
- wherein the first motion measurement module is operative to provide the value representative of the first motion at the rate for the control circuitry to read values representative of the first motion from the first motion measurement module and read values representative of the second motion value from the second motion measurement module, for the control signal operative in the read mode.

One or more embodiments in accordance with the first, second, third and fourth aspects may be configured and operated so that the first motion measurement module, and one or more other circuitry, may be operated in a low power mode so as to wait for a first motion value satisfying the first motion value criterion. The control circuitry initiating the second rate may cause the first motion measurement module to provide first motion values more often than for the first sample rate and therefore use more power and operate in a higher power usage mode. The control circuitry may be a processor, microcontroller or some other form of programmable digital circuitry and associated processor resources. The third signal may be an interrupt signal and recognised by the control circuitry as a data ready signal. The data rate may be higher by using an interrupt signal as a data ready signal than otherwise would be the case because using an interrupt signal detectable on a falling or rising edge does not require a "settle" time at a low or high voltage state as would be the case if a signal level were used for timing and to initiate or "gate" providing motion data. Thus, more data or a greater density of data may be obtained for an impact event.

A second motion value representative of a second motion may be provided, for example from a second motion measurement module; the control circuitry responsive to the first signal to invoke a second motion measurement mode operative to measure a second motion, for example by sending a fourth signal to the second motion measurement module, and to initiate a read of a second motion value of the second motion measurement module. Thus a second motion may be measured but only when the first motion has satisfied the first motion value criterion.

The control circuitry may be operative in a low power mode pending receipt of the first signal from the first motion measurement module and to invoke a second higher power mode responsive to receipt of the first signal. Thus, an embodiment may be configured to only use such power as is necessary for respective rates.

The control circuitry may be operative to initiate a read of the sample second motion value subsequent to initiating the read of the current first motion value. Thus, there may only be a minimal delay in reading the first and second motion values because the first motion value may be read as soon as the high power mode is initiated and while the second motion measurement module enters its high power mode.

The motion measurement module may be operative such that the second rate is sufficient for the time period between chronologically adjacent third signals to encompass both reading the first motion value of the first motion measurement module and reading the second motion value of the second motion measurement module. Thus, providing a further signal to initiate reading the second motion value may be obviated.

The first motion measurement module may be operative in the second mode for a pre-set time period. Such a pre-set time period may encompass the duration of violent head movement following a head impact event thereby providing motion data for such violent head movement.

In one or more embodiments the first signal may be sent to the control circuitry at the rate responsive to the value representative of the first motion satisfying the criterion. Continuing to send the first signal at the rate may maximize the rate at which first motion values may be read as it is at the same rate as they are provided by the first motion measurement module. The first signal may be an interrupt signal and recognised by the control circuitry as a data ready signal. The data rate may be higher by using an interrupt signal as a data ready signal than otherwise would be the case because using an interrupt signal detectable on a falling or rising edge does not require a "settle" time at a low or high voltage state as would be the case if a signal level were used for timing and to initiate or "gate" providing motion data. Thus, more data or a greater density of data may be obtained for an impact event.

There may be provided a second motion measurement module operative to provide a value representative of a second motion; the control circuitry responsive to the first signal to read a value representative of a second motion. A second motion measurement module may measure a complementary motion to that of the first motion detection module so that more information about a head impact event for example, may be collected than if just one type of motion was measured. For example, the second motion may be an angular velocity and the first motion may be a linear acceleration In one or more embodiments the control circuitry may be operative in a low power mode pending receipt of the first signal from the first motion measurement module and invokes the read mode at a higher power than the low power mode responsive to receipt of the first trigger signal. Operating the control circuitry in a low power mode until an event to be measured occurs saves on power usage and may provide for a longer operating time of the system. In one or more embodiments the rate may be sufficient to read the value representative of the first motion value from the first motion measurement module and to read the value representative of the second motion value of the second motion measurement module within one cycle of the rate. Such an arrangement may obviate the need to provide a second timing circuit or arrangement for reading second motion values and links the read rate for the second motion to the read rate for the first motion thereby maintaining the timing relationship between them without the need for synchronising circuitry, mechanisms or the like.

In one or more embodiments, the control circuitry is operative to send a "go to sleep" signal to the second motion measurement module to invoke a low power mode following elapse of a pre-set time period. Optionally, the control circuitry is operative in the read mode for a second pre-set time period before ceasing the read mode.

Typically, the pre-set time period and the second time period are the same time period.

Suitably, the predetermined criterion comprises the value representative of the first motion exceeding an acceleration threshold.

The acceleration threshold may be in the range 3 g to 5 g, in particular the threshold is 5 g, where "g" is the acceleration due to gravity. Force in such a range may be a suitable indication of a significant force that may be the start of a head impact event.

In one or more embodiments, the predetermined criterion may comprise the value representative of the first motion indicative of the first motion comprising increasing acceleration exceeding a threshold rate of increase. Monitoring for and identifying an increase in the rate of increase, i.e. increasing acceleration, may provide an indication of the start of a "true" or "real" impact event. Typically, the predetermined criterion comprises the increasing acceleration exceeding the threshold rate for the increasing acceleration traversing an acceleration threshold. Suitably, the acceleration threshold traversed by the increasing acceleration is in the range 3 g-5 g, in particular 5 g.

In one or more embodiments control circuitry may be operative in the read mode for a pre-set time period before ceasing the read mode. Setting a pre-set time period obviates having a second criterion to be satisfied by the first motion value (or second motion value) to initiate a halt of the read mode. Suitably, the pre-set time period is based on the typical length of the type of event for which motion is to be measured, e.g. the typical length (or possibly a little longer to avoid missing relevant data) of a head impact event if that is the type of event for which motion is to be measured.

Suitably, the pre-set time period is at least sufficient to read between 70 to 130 first and second motion values, in particular sufficient to read between 85 to 115 first and second motion values, more particularly sufficient to read between 95 to 110 first and second motion values, yet more particularly sufficient for 104 first and second motion values.

Typically, the first motion value may comprise respective component first motion values representative of a first motion measured for each of mutually orthogonal directions (X, Y, Z). Likewise, the second motion value may comprise respective component values representative of a second motion measured for each of mutually orthogonal directions (X, Y, Z). Measurement of the motion values in mutually orthogonal directions or planes is useful because a motion may be analyzed in respective directions or planes.

In one or more embodiments, the first motion measurement module is operative to determine a first motion vector from the first motion measured for each of mutually orthogonal directions (X, Y, Z) and provide the first motion vector as the first motion value. Evaluating such a vector takes into account all contributions of motion.

Optionally or additionally in one or more embodiments the first motion measurement module is operative to sample first motion values measured for each of mutually orthogonal directions (X, Y, Z) and provide the sampled first motion values to the control circuitry. Thus, the first motion measurement module may avoid computing the vector sum which may be computed in the control circuitry. This may be particularly synergistic if the control circuitry comprises processor circuitry.

Suitably, the first motion is a linear motion. Measuring linear motion first can be useful because the linear motion may tend to show the most rapid change in the event of an impact event and so is a useful trigger to initiate the read mode.

Suitably, the linear motion is linear acceleration and the first motion measurement module is a linear acceleration measurement module. Linear acceleration is a relatively easy quantity to understand as proportional to force. Typically. the linear acceleration measurement module is an accelerometer.

In one or more embodiments, the second motion is an angular motion measured around respective axes of rotation in mutually orthogonal directions (X', Y', Z'). Such a motion is particularly useful motion if monitoring for a head impact event as the head tends to rotate after the impact.

In particular the motion may be angular velocity and the second motion measurement module an angular velocity measurement module. Although angular acceleration would have to be derived from the angular velocity values, devices to measure angular velocity are readily available.

Viewed from a fifth perspective there is provided a system wherein the control circuitry is further operative to set a flag responsive to a first motion value satisfying a second criterion.

Viewed from a sixth perspective, there is provided a method comprising setting a flag responsive to the first motion value satisfying a second criterion.

Determining whether or not a second first motion value has been satisfied provides for further preliminary analysis of a motion profile permitting earlier decision making concerning that profile.

Suitably, the control circuitry is further operative to unset the flag responsive to the first motion value not satisfying the second criterion. Thus, returning to a default position concerning the acceleration profile.

In one or more embodiments, the control circuitry is further operative to determine the flag as set or unset after a read of a first motion value and to make a subsequent read of the first motion value for determining the flag is set. Thus, the system may enter a low power mode and/or use less power if the criterion is not satisfied thereby conserving power.

In one or more embodiments, the control circuitry is further operative to determine the flag as set or unset after a pre-set number of first motion value read operations and to make subsequent reads of the first motion value for determining the flag is set. Thus, the determination is not made after each read thereby saving power and use of processing resources.

Typically, the first motion value comprises one or more acceleration values and thus the system may determine whether the measured acceleration early in the period following the first criterion being satisfied is indicative of an acceleration event such as an impact event.

According to yet still another feature of the present disclosure viewed from a first aspect, there is provided a system for monitoring acceleration of an intra oral appliance, the system comprising:

a motion monitoring system operative to monitor acceleration experienced by the intra oral application and operative to communicate acceleration data to a monitoring station, the motion monitoring system comprising:

a motion measurement module operative to provide data representative of a motion;

a data packet compiler for compiling a data transmission comprising at least one data packet for transmission to a monitoring station;

an incomplete transmission management module to retrieve at least one data packet from a storage device of said motion monitoring system responsive to notification, from a monitoring station, of an incomplete receipt of a data transmission;

a power source for providing power to the motion monitoring system; and a power source monitoring system to monitor a power source operating parameter of said power source and to output data representative of a power source status based upon a monitored operating parameter of said power source. One or more embodiments in accordance with the first aspect may operate in a manner that consumes less power than conventional low power transmission systems since data acknowledgement signals are not exchanged for each transmission between the motion monitoring system and the monitoring station. Data transmissions are monitored for missing, incomplete or erroneous data packets and a request to resend the relevant data packets is made only if there are missing, incomplete or erroneous data packets thereby saving on transmissions and hence power.

In one or more embodiments the data packet compiler is operative to compile an impact data transmission comprising a plurality of data packets, each data packet comprising data representative of a part of said motion. Compiling packets into an impact data transmission may reduce power usage yet further because erroneous transmission in a plurality of packets may occur when compiled together resulting in one request for a send and resend rather than multiple requests had the packets been transmitted individually.

Typically, the power source monitoring system comprises power source monitoring circuitry and a power source monitoring module, said power source monitoring circuitry coupled to said power source and configured to output, to said power source monitoring module, a signal comprising a measured value of a parameter of said power source. Such a measurement of a parameter of the power source may provide a reliable indication of the power output of the power source.

In one or more embodiments, the power source monitoring module is operative to compare said measured value of said parameter of said power source to a threshold value. Setting a threshold value and comparing a measured value to the threshold is a less computationally intensive process for determining if a power source is providing or ready to provide sufficient power than a more complex approach.

In one or more embodiments, responsive to a determination that said measured value is less than, or equal to, said threshold value, said power source monitoring module issues an instruction invoking an inactive state of said system. Such operation may avoid inaccurate determination of impact parameters and transmission of the same or an unacceptedly great number of corrupt transmissions.

Optionally or additionally, responsive to a determination that said measured value is greater than said threshold value, said power source monitoring module issues an instruction invoking an active state of said system. This may provide a reliable operation since the system has determined there is sufficient power for operation.

In one or more embodiments, the system may further comprise a status monitoring module operative to at least one of:

monitor a status of a plurality of operating conditions and/or parameters of said motion monitoring system and forward data representative of said plurality of operating conditions and/or parameters to said data packet compiler; and retrieve historic impact data from a storage device of said motion monitoring system and forward said historic impact data to said data packet compiler. Monitoring data representative of a plurality of operating conditions and/or parameters provides for the potential to reduce even further the likelihood of errors in determining and transmitting data since other factors may be taken into account. Retrieving historic data may be a suitable approach to address any transmission errors by resending historic data. Simply resending historic data may be less computationally intensive than using other methods of addressing transmission errors, in particular if a standard or preset volume of historic data is to be sent thereby obviating any need to determine what data needs to be resent and thus reducing power usage.

In one or more embodiments, said data packet compiler, responsive to receipt of: said data representative of said plurality of operating conditions and/or parameters; and/or said historic impact data, is operative to, or further operative to, create a status data packet containing: said data representative of said plurality of operating conditions and/or parameters; and/or said historic impact data, for transmission to a monitoring station. Such a status packet may conveniently indicate whether or not the motion measurement module or other relevant art of the monitoring system was active, inactive or possibly in an intermediate state.

Suitably, in one or more embodiments said status monitoring module and said data packet compiler, responsive to said instruction invoking said active state, create said status data packet on a periodic basis. Setting a periodicity at which the status data packet is created may help to methodically monitor the status of the monitoring module.

In one or more embodiments, a status data packet is created and transmitted at a specific time period from creation and transmission of a previous status data packet, thereby creating a process in which the interval between status data packets being created and transmitted is sought to be consistent.

Optionally or additionally, in one or more embodiments a status data packet is created and transmitted at a specific time period from creation and transmission of a previous status data packet, unless a transmission comprising impact data has been created and transmitted responsive to measurement of an impact event during the specific period following the transmission of the previous status data packet, in which case said status data packet is created and transmitted at a specific time period from creation and transmission of said transmission comprising impact data. Thus, unnecessary repetition of the transmission of data is avoided.

Typically, said specific time period from creation and transmission of a previous status data packet and said specific time period from creation and transmission of said transmission comprising impact data are of a same duration which provides for simplicity and maintains the interval between transmissions substantially constant other than an intermediate impact data transmission. Generally, said duration is ten seconds.

Suitably, in one or more embodiments said historic impact data comprises a number of impact events recorded by the motion monitoring system in a current session. In this way it may be possible to recover impact data even if there has been a significant delay, say up to 600 seconds, optionally up to 400 seconds, further optionally up to 200 seconds, yet further optionally up to 100 seconds, yet even further optionally up to 60 seconds.

Suitably, said historic impact data comprises data representative of a maximum acceleration value reached during at least one previous impact event. Such a reduced amount of data compared to what is usually transmitted as impact data means that a data about a greater number of impacts may be stored and recovered than if the usual impact data were to be stored.

In one or more embodiments, said data representative of said plurality of operating conditions and/or parameters comprises data representative of at least one of: a status of said power source; an identifier unique to the motion monitoring system; and a time period for which the motion monitoring system has been active. Such parameters may be used to determine not only if there is sufficient power in a power source to operate the monitoring module but also the likely period for which such power may be available.

Typically, said data representative of said status of said power source comprises data representative of at least one of: a power output level of said power source; a charge level of said power source; and a state-of-health of said power source.

In one or more embodiments, said incomplete transmission management module is operative to retrieve at least one data packet from a storage device of said motion monitoring system responsive to notification, from a monitoring station, of an incomplete receipt of an impact data transmission.

Viewed from a second perspective, there is provided a monitoring station for receiving a data transmission from a system according to any of the preceding claims, the monitoring station comprising:

a received data packet monitor for determining if a data transmission received from said system is complete and/or comprises non-erroneous data;

an incomplete data notifier operative, responsive to a determination from said received data packet monitor that a received data transmission is incomplete and/or comprises erroneous data, to prepare a message, for transmission to said system, said message containing data identifying missing and/or erroneous data packets and a request for these data packets to be re-sent by the system;

a power source status alert module operative to, from data received in said data transmission, compare a value representative of a power source status of a power source of said system to a threshold value and, if said value is less than, or equal to, said threshold value, to initiate issue of an alert indicative of a sub-optimal status of said power source.

Such a monitoring station may further comprise a remaining charge assessment module operative to receive an indication from said power source status alert module that, in said comparison, said value is greater than said threshold value, and responsive thereto operative to determine a period of time for which the value is likely to exceed the threshold value.

In the monitoring station said determination is based upon a comparison with a charge versus voltage graph or table, such as available from the battery manufacturer or by calibration of one or more battery units, in order to provide an indication of charge and hence time for which battery may be capable of delivering sufficient charge to operate the system for monitoring acceleration. Such an indication may be the display of the charge value obtained from the graph or table.

In one or more embodiments of the monitoring station said remaining charge assessment module may be further operative to compare a value representative of said determined period of time to a value representative of a threshold period of time.

In one or more embodiments the monitoring station may be responsive to a determination that said value representative of said determined period of time is less than, or equal to, said value representative of a threshold period of time, said remaining charge assessment module operates to initiate issue of an alert indicative of impending low charge of said power source of said system.

Viewed from a third perspective, there is provided an impact assessment system, comprising:
a system for monitoring acceleration of an intra oral appliance such as set out in the foregoing; and
a monitoring station as set out in the foregoing.

BRIEF DESCRIPTION OF THE DRAWINGS

One or more specific embodiments in accordance with aspects of the present disclosure will be described, by way of example only, and with reference to the following drawings in which:

FIG. 11. is a process control flow diagram for an H3LIS accelerometer in accordance with a second embodiment of the present disclosure.

FIG. 12 is a process control flow diagram for an H3LIS control circuitry configured as a processor in accordance with a second embodiment of the present disclosure.

DETAILED DESCRIPTION OF CERTAIN EMBODIMENTS

A mouth-guard (or gum-shield) is a piece of protective equipment worn by participants in sports, particularly contact sports. A mouth-guard is typically worn in an upper part of the mouth of the participant and is generally configured to cover at least a portion of the upper teeth of the participant. Most typically, a mouth-guard is configured to cover at least a portion of a vestibular (outer) surface of upper teeth of the wearer, at least a portion of a palatal (inner) surface of upper teeth of the wearer, and at least a portion of incisal and occlusal surfaces (i.e. "biting" and "chewing" surfaces) of upper teeth of the wearer.

In general outline, a mouth-guard according to one or more embodiments of the present disclosure can form a part of a system for the detection, measurement, characterisation, transmission, and/or reporting of impact events causing acceleration to be experienced by participants. Sensor components and/or monitoring element components located in the mouth-guard are used to monitor accelerations experienced by participants and data representative of such accelerations can be conveyed to a monitoring station for review by a technician, for example, a trained medical professional. This can allow the technician to make a decision regarding whether or not a participant in a sports match is fit to continue playing (e.g. following a particularly heavy head impact event) or should be removed from play and referred for further testing with a medical professional.

In the present description, the phrase "head impact event" relates to both direct impacts to the head and indirect impacts. That is, where the head receives a blow directly, or when a blow is sustained to some other body part and the force of the blow causes, amongst other things, an acceleration of the head. Further, reference is made to a participant sustaining an impact and their head experiencing an acceleration because of the impact. The acceleration of the head may be as a result of an impact directly to the head (i.e. a force is exerted on the head directly), or as result of an impact to another part of the body, but the result of which is that force is transmitted to the head from the point-of-impact through the body and neck. Such an acceleration may be termed an impact acceleration.

The sensor and/or monitoring element components are embedded and/or encapsulated in material from which the mouth-guard is formed.

Figure 1:
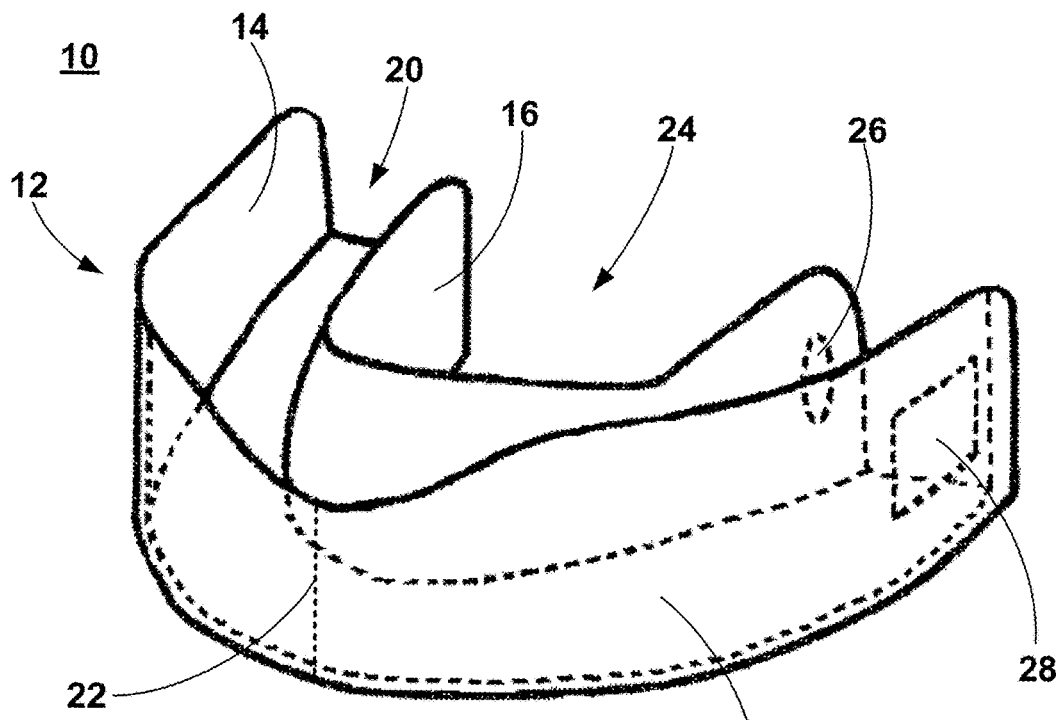
FIG. 1 illustrates a mouth-guard according to one or more embodiments of the present disclosure in which embedded and/or encapsulated components are arranged in a first arrangement.
Figure 2:
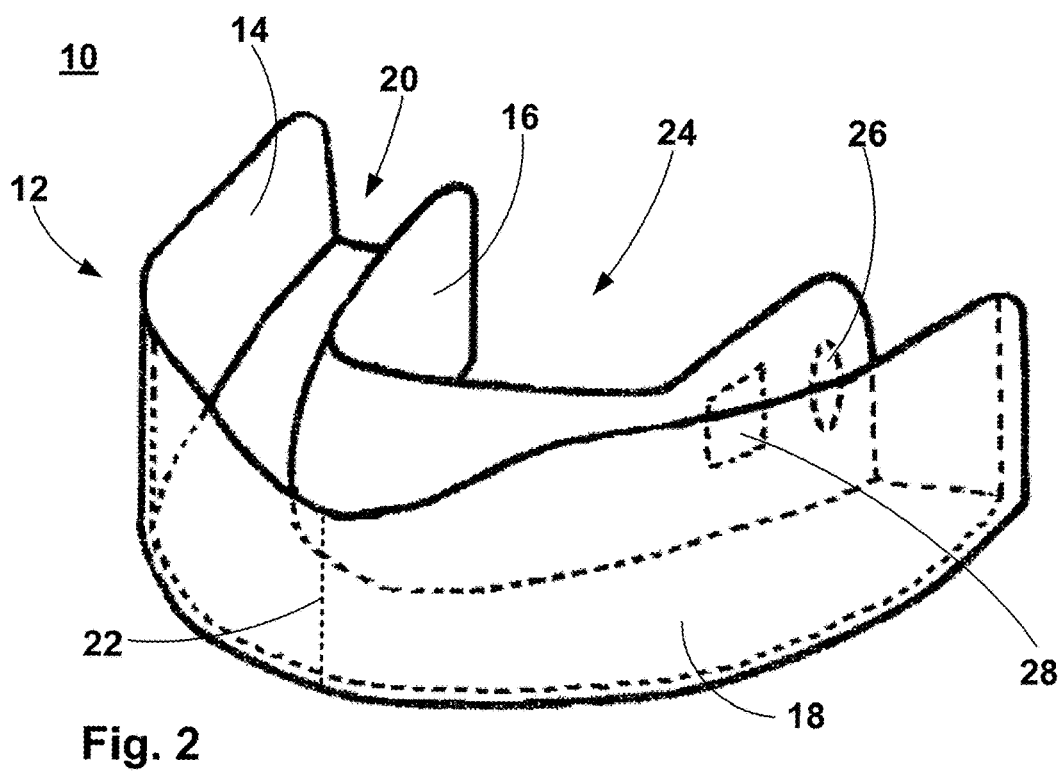
FIG. 2 illustrates a mouth-guard according to one or more embodiments of the present disclosure in which embedded and/or encapsulated components are arranged in a second arrangement.

FIG. 1 illustrates a mouth-guard 10 according to one or more embodiments of the present disclosure in which embedded and/or encapsulated components are arranged in a first arrangement. FIG. 2 illustrates a mouth-guard 10 according to one or more embodiments of the present disclosure in which embedded and/or encapsulated components are arranged in a second arrangement.

In the illustrated mouth-guard 10 of FIGS. 1 and 2, components are shown positioned in walls of the mouth-guard that are locatable at the rear of a mouth of a wearer when the mouth-guard is located correctly in the mouth.

The components are connected electronically by means of wires or circuit board (which may be flexible) and are communicatively coupled to a transceiver for transmitting data received from the components to a monitoring station in real-time. These components operate to collect and process impact event data, which can then be transmitted to the monitoring station via the transceiver.

Various terms used in dentistry are used in describing the mouth-guard 10 of one or more embodiments of the present disclosure. The terms used in this disclosure are listed below:

Anterior—The direction towards the front of the head or the lips, as opposed to posterior, which refers to the directions towards the back of an individual's head. The term anterior teeth refers to incisors and canines, as opposed to premolars and molars, which are posterior teeth;

Distal—The direction towards the gums beyond the tooth furthest from the midline (i.e. the 'most posterior tooth' or last tooth) in each quadrant of a dental arch, as opposed to mesial, which refers to the direction towards the midline;

Incisal—The direction towards the biting edge of front teeth. This is a related term to occlusal, which relates to the analogous location on rear teeth;

Mandibular—Relating to the mandible, or lower jaw;

Maxillary—Relating to the maxilla, or upper jaw;

Mesial—The direction towards the midline in a dental arch, as opposed to distal, which refers to the direction towards the gums beyond the tooth furthest from the anterior midline (the 'most posterior tooth' or last tooth) in each quadrant;

Midline—Roughly, an imaginary vertical line dividing the left and right sides of the mouth at the teeth;

Occlusal—The direction towards the biting surface of rear teeth. This is a related term to incisal, which relates to the analogous location on anterior teeth;

Palatal—The side of a tooth adjacent to (or the direction towards) the palate, as opposed to vestibular, which refers to the side of a tooth adjacent to (or the direction towards) the inside of the cheek or lips of the mouth respectively;

Posterior—The direction towards the back of an individual's head, as opposed to anterior, which refers to the directions towards an individual's lips. The term posterior teeth refers to premolars and molars, as opposed to incisors and canines, which are anterior teeth;

Quadrant—The arrangement of teeth in a mouth is divided into four quarters. Upper and lower sets of teeth form an oval, which is divided into quadrants:
Upper right quadrant: upper right first incisor to upper right wisdom tooth;
Upper left quadrant: upper left first incisor to upper left wisdom tooth;
Lower right quadrant: lower right first incisor to lower right wisdom tooth;
Lower left quadrant: lower left first incisor to lower left wisdom tooth; and Vestibular—The side of a tooth that is adjacent to (or the direction towards) the inside of the cheeks and lips, as opposed palatal, which refers to the side of a tooth adjacent to the palate.

Additionally, reference is made to monitoring acceleration. In at least some implementations, a device used to measure acceleration is termed an "accelerometer". The terms "acceleration measurement", "acceleration monitoring" and the like include use of devices known as "accelerometers". The terms may be used interchangeably depending on context.

As illustrated in FIGS. 1 and 2, the mouth-guard 10 comprises a body 12 that defines a formation to be located around at least a portion of maxillary teeth of a wearer (i.e. teeth in the upper jaw of the wearer—hereinafter "upper teeth"), to cover, surround, and/or envelope the upper teeth of the wearer.

The body 12, formed from a plastics, resin, and/or rubber material, comprises a first wall 14 configured to cover at least a portion of an outer surface of the upper teeth of the wearer (i.e. the surface of the upper teeth that faces the inside of the upper lip and the cheek). In dentistry terminology this surface is known as a vestibular surface.

The body 12 comprises a second wall 16 configured to cover at least a portion of an inner surface of the upper teeth of the wearer (i.e. the surface of the upper teeth that faces the palate). In dentistry terminology this surface is known as a palatal surface.

The body 12 comprises a third wall 18 connecting the first and second walls 14, 16 and configured to cover at least a portion of biting edges and chewing surfaces of the upper teeth of the wearer (i.e. the edges and surfaces of the upper teeth that are opposed to the lower teeth). In dentistry terminology, these surfaces are known as incisal and occlusal surfaces.

The first, second and third walls 14, 16, 18 of body 12 define a channel 20 for receiving a plurality of teeth of a wearer. In the illustrated examples of FIGS. 1 and 2, the channel 20 is structured such that, when worn, it covers teeth that include the incisors of a wearer when the mouth-guard 10 is inserted.

In plan view, the body 12 of the mouth-guard 10 presents a generally symmetrical U-shaped configuration with "arms" extending away from a mid-line (denoted by dashed line 22 in FIGS. 1 and 2). The first, second and third walls 14, 16, 18 in one arm define a portion of the channel 20 that can receive teeth of an upper left quadrant. The first, second and third walls 14, 16, 18 in the other arm define a portion of the channel 20 that can receive teeth of an upper right quadrant.

The mouth-guard 10 also defines an open area 24, located between the two arms, which can allow a tongue of the wearer to touch their upper palate when the mouth-guard 10 is being worn. This may allow the user to maintain verbal communication with other participants (e.g. teammates) without requiring removal of the mouth-guard.

The mouth-guard 10 includes a power source 26 (e.g. an electrical power battery) that is electrically connected to a system for monitoring acceleration 28. Typically, the power source 26 is of a type compatible with a wireless charger to allow recharging of the power source, i.e. the power source 26 may be wirelessly rechargeable, which allows the power source 26 to be charged/recharged without requiring removal from the mouth-guard 10.

In the illustrated example of FIG. 1, the power source 26 and system for monitoring acceleration 28 are located in a portion of the same arm of the mouth-guard. The portion in which they are located is in a distal direction from the mid-line 22. The power source 26 is located in the second wall 16 and the system for monitoring acceleration 28 is located in the first wall 14. The power source 26 and system for monitoring acceleration 28 are electrically connected using a suitable connection (not shown) that runs from the power source 26, through the third wall 18 to the system for monitoring acceleration 28.

Locating the power source 26 and system for monitoring acceleration 28 in a distal direction away from the mid-line 22 (i.e. so that these components are located in a portion of the mouth-guard 10 that is located in a rear part of the mouth of the wearer, when worn) may reduce the likelihood of damage to the power source 26, system for monitoring acceleration 28 and/or teeth when the wearer sustains an impact. For instance, if the wearer undergoes a collision where a point of impact is at the front of the face of the wearer (e.g. at, or around, the mid-line of the upper teeth of the wearer), then damage to the power source 26 and/or system for monitoring acceleration 28 may be inhibited, because these components are located at positions away from the point of impact. Locating the power source 26 and/or system for monitoring acceleration 28 away from points of likely impact may reduce the likelihood of damage to teeth, because the "hard" bodies making up the housings of the power source 26 and/or system for monitoring acceleration 28 are in positions where they are less likely to be forced into the teeth.

Optionally, the power source 26 and/or system for monitoring acceleration 28 may be located in a different area of the mouth-guard 10 in one or more embodiments. FIG. 2 illustrates another example, in which the power source 26 and system for monitoring acceleration 28 are, again, located in a portion of the same arm of the mouth-guard. The portion in which they are located is in a distal direction from the mid-line 22. However, in the example illustrated in FIG. 2, both the power source 26 and the system for monitoring acceleration 28 are located in the second wall 18.

In a mouth-guard 10 of the type illustrated in FIG. 2, likelihood of damage to the power source 26 and/or system for monitoring acceleration 28 when the wearer sustains an impact to the head may be reduced not only because the power source 26 and system for monitoring acceleration 28 are located in the mouth-guard 10 in a distal direction away from the mid-line 22 (i.e. so that these components are located in a portion of the mouth-guard 10 that is located in a rear part of the mouth of the wearer, when worn), but also because the power source 26 and system for monitoring acceleration 28 are located in a portion of the mouth-guard 10 that is locatable inside (i.e. on a palatal side of) the upper teeth. The teeth themselves can serve as a barrier to offer a level of protection to the components. In addition to the potential to inhibit damage during frontal impacts, the location of the components in the example of FIG. 2 may, in an instance where the wearer undergoes a collision where a point of impact is at the side of the face, inhibit damage to the power source 26 and/or system for monitoring acceleration 28, because these components are located at positions in which they are shielded, at least in part, by the teeth of the wearer.

In the illustrated examples of FIGS. 1 and 2, the components of the mouth-guard 10, described above, are encapsulated (i.e. wholly embedded) within material forming the mouth-guard 10.

Figure 3:
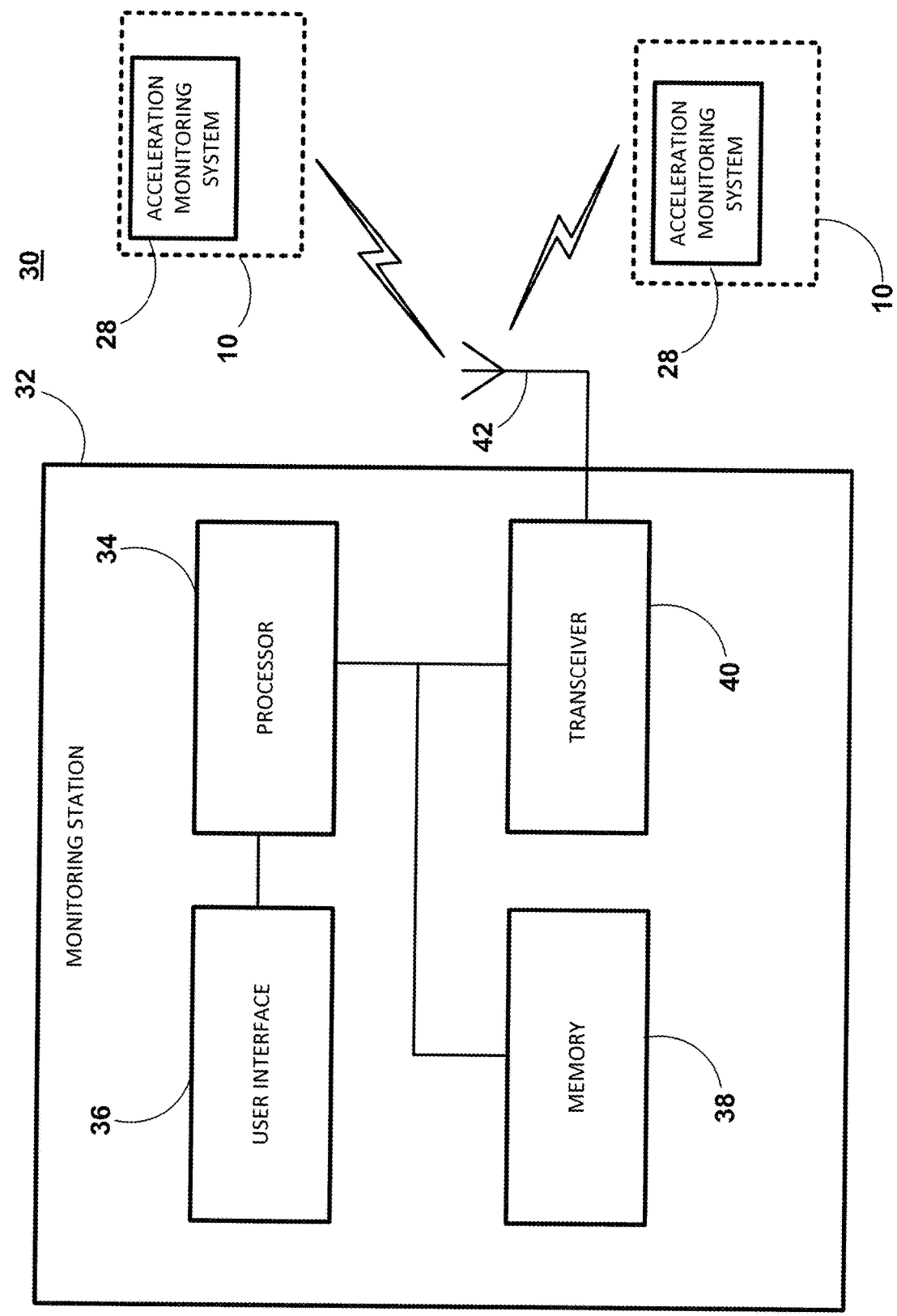
FIG. 3 illustrates a system for providing a monitoring environment for monitoring acceleration sustained by participants in a sporting event.

FIG. 3 illustrates a system 30 for providing a monitoring environment for monitoring acceleration sustained by participants in a sporting event.

The system 30 operates to aggregate data representative of acceleration that occurs during impact events, the data being received from systems for monitoring acceleration 28 in mouth-guards 10 worn by game participants. The data can be conveyed to technicians, via the system, for assessing the seriousness of one or more impact events.

The system 30 comprises a monitoring station 32 that is in wireless communication with one or more systems for monitoring acceleration 28. The monitoring station 32 can communicate data received from the one or more systems for monitoring acceleration 28 to one or more devices (not shown in FIG. 3—see FIG. 5) either wirelessly or by wired communication link.

The monitoring station 32 includes a processor 34, a user interface 36, memory 38, and a transceiver 40. The monitoring station 32 wirelessly receives data representative of accelerations experienced by participants from each of the systems for monitoring acceleration 28. Signals from each of the systems for monitoring acceleration 28 are received at an antenna 42 coupled to the transceiver 40. The received signals are passed to the processor 34, which operates to process the data. Processed data is communicated to memory 38 for storage and can also be communicated to user interface 36, which is configured for communicating the data to a display device (e.g. via a communications network).

Figure 4:
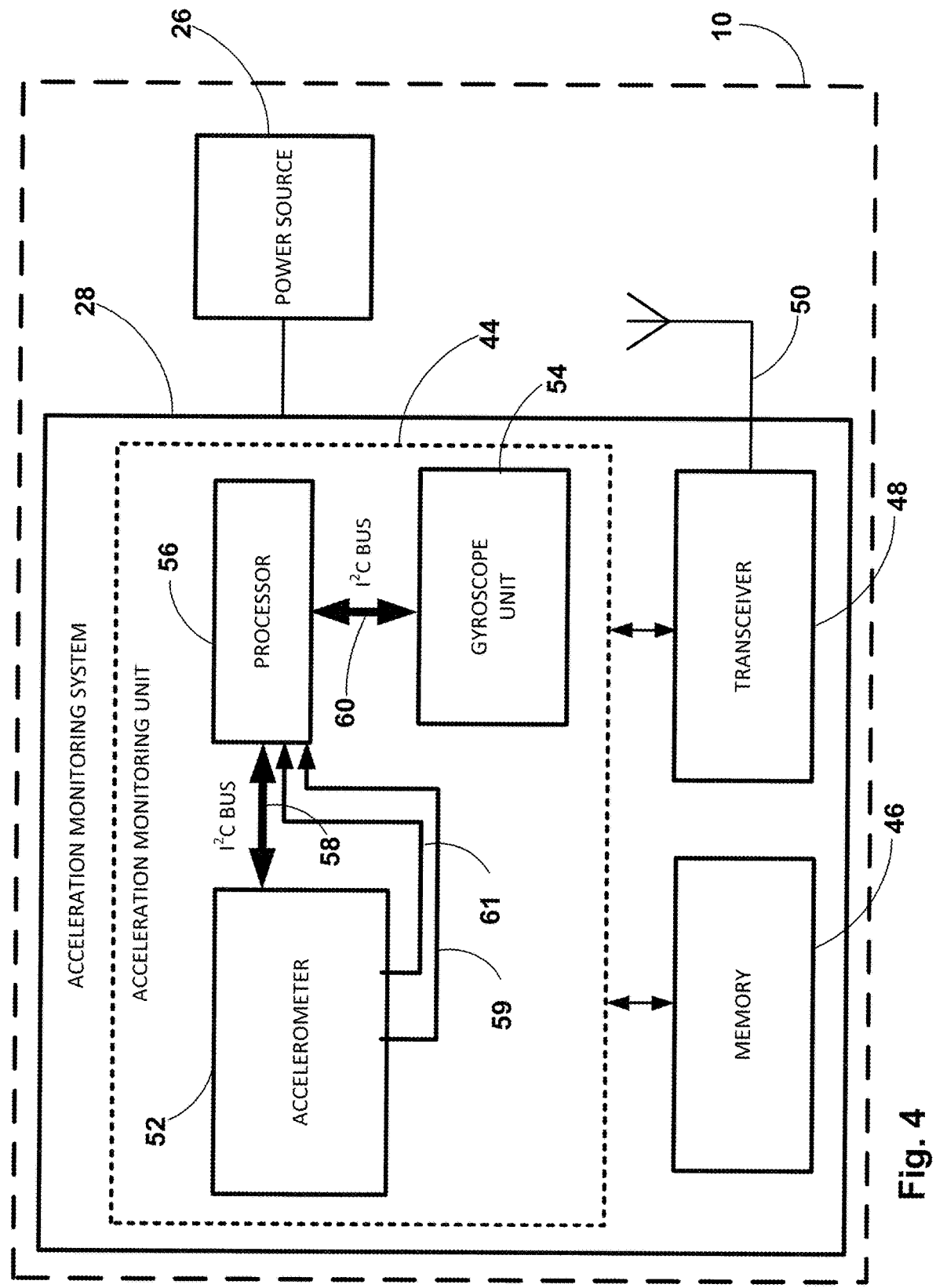
FIG. 4 illustrates components of a mouth-guard according to one or more embodiments of the present disclosure.

FIG. 4 illustrates components of the mouth-guard 10 (e.g. the power source 26 and the system for monitoring acceleration 28) in more detail.

The system for monitoring acceleration 28 comprises an acceleration monitoring unit 44, a memory 46 and a transceiver 48. The acceleration monitoring unit 44 is operative to monitor acceleration experienced by a wearer of the mouth-guard 10, and is electrically coupled to the memory 46, which serves to store data representative of acceleration monitored by the acceleration monitoring unit 44. The acceleration monitoring unit 44 is also electrically coupled to the transceiver 48, which is operative to communicate a data signal containing data representative of acceleration monitored by the system for monitoring acceleration to the monitoring station 32 via antenna 50. Data can also be received by the system for monitoring acceleration 28 from an external source via the antenna 50 and transceiver 48. Received data may comprise, for example, a negative-acknowledgement signal (e.g. to indicate an error in data previously sent from the system for monitoring acceleration 28 and to request that the data be re-sent), software updates, etc.

The acceleration monitoring unit 44 comprises a three axis linear accelerometer 52, an gyroscope unit 54 and a processor 56. Each of the acceleration monitoring unit 44 and the gyroscope unit 54 are communicatively coupled to the processor 56 by way of Inter-Integrated Circuit ($I^2C$) buses 58, 60 respectively.

The accelerometer 52 is operative to monitor linear accelerations of the mouth-guard 10. The accelerometer 52 is operative to measure a linear acceleration in each orthogonal direction (x, y, z), e.g. of a Cartesian coordinate reference frame. A combination of respective acceleration values may be used to derive a linear acceleration vector.

The gyroscope unit 54 is operative to measure angular velocity to provide data representative of angular rotation. The gyroscope unit 54 is operative to measure angular velocity with respect to each orthogonal direction (x, y, z), e.g. of a Cartesian coordinate reference frame. A combination of respective angular velocity values may be used to derive an angular velocity vector.

The accelerometer 52 and gyroscope unit 54 are operative to monitor attributes of the environment of the mouth-guard 10 over time to determine a linear acceleration of the system for monitoring acceleration 28 and an angular velocity of the system for monitoring acceleration 28. Using data indicative of linear acceleration and angular velocity, which is communicated to the processor 56, the processor 56 is able to determine the fact of an event causing acceleration of a particular magnitude and a rotation. This data can be used in the system for monitoring acceleration 28 and/or the monitoring station 32, to calculate a vector representative of a magnitude of the linear acceleration and a vector representative of an angular velocity experienced by the system for monitoring acceleration 28.

Figure 5:
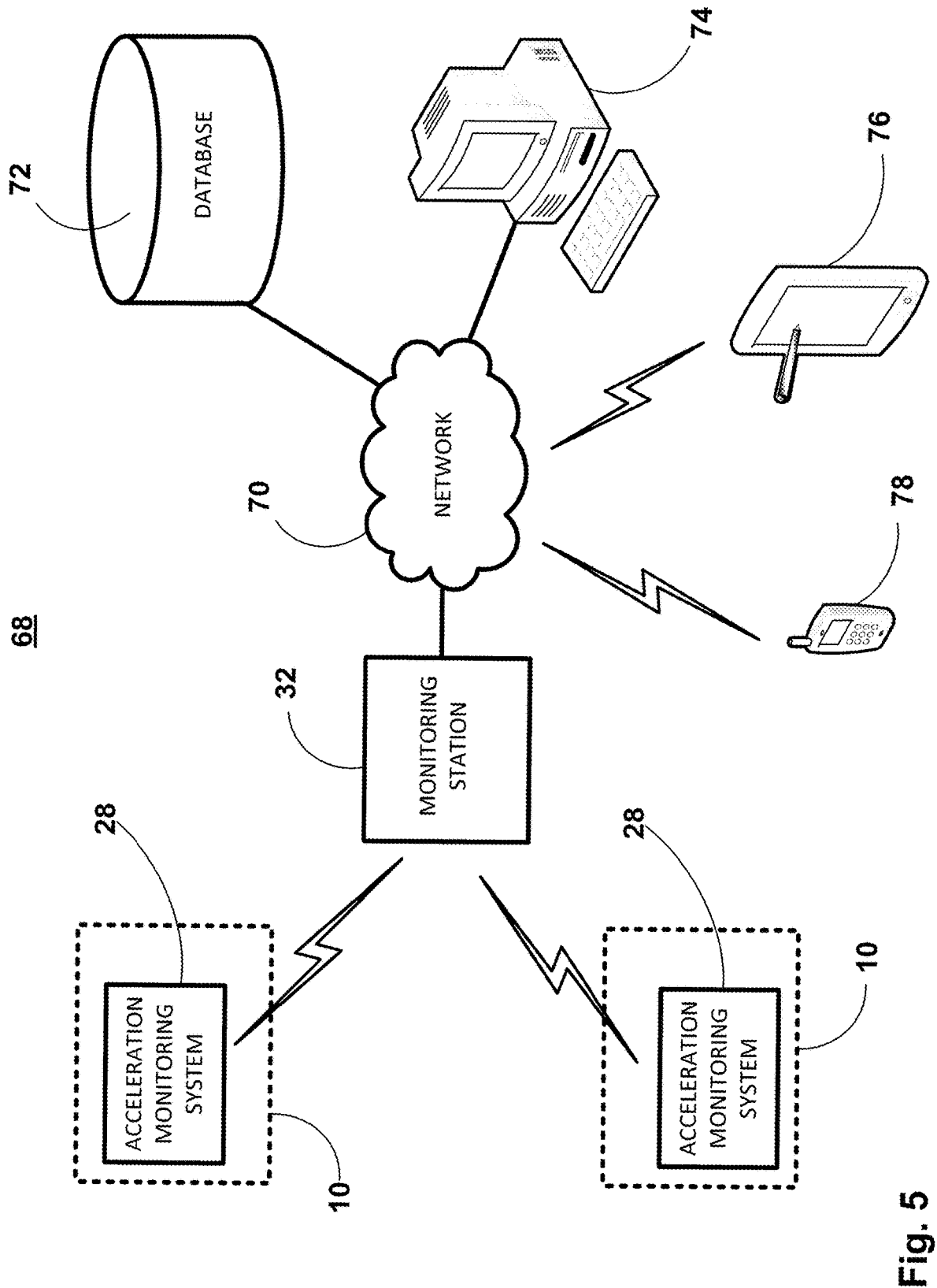
FIG. 5 illustrates an impact assessment system comprising one or more mouth-guards according to one or more embodiments of the present disclosure.
Figure 6:
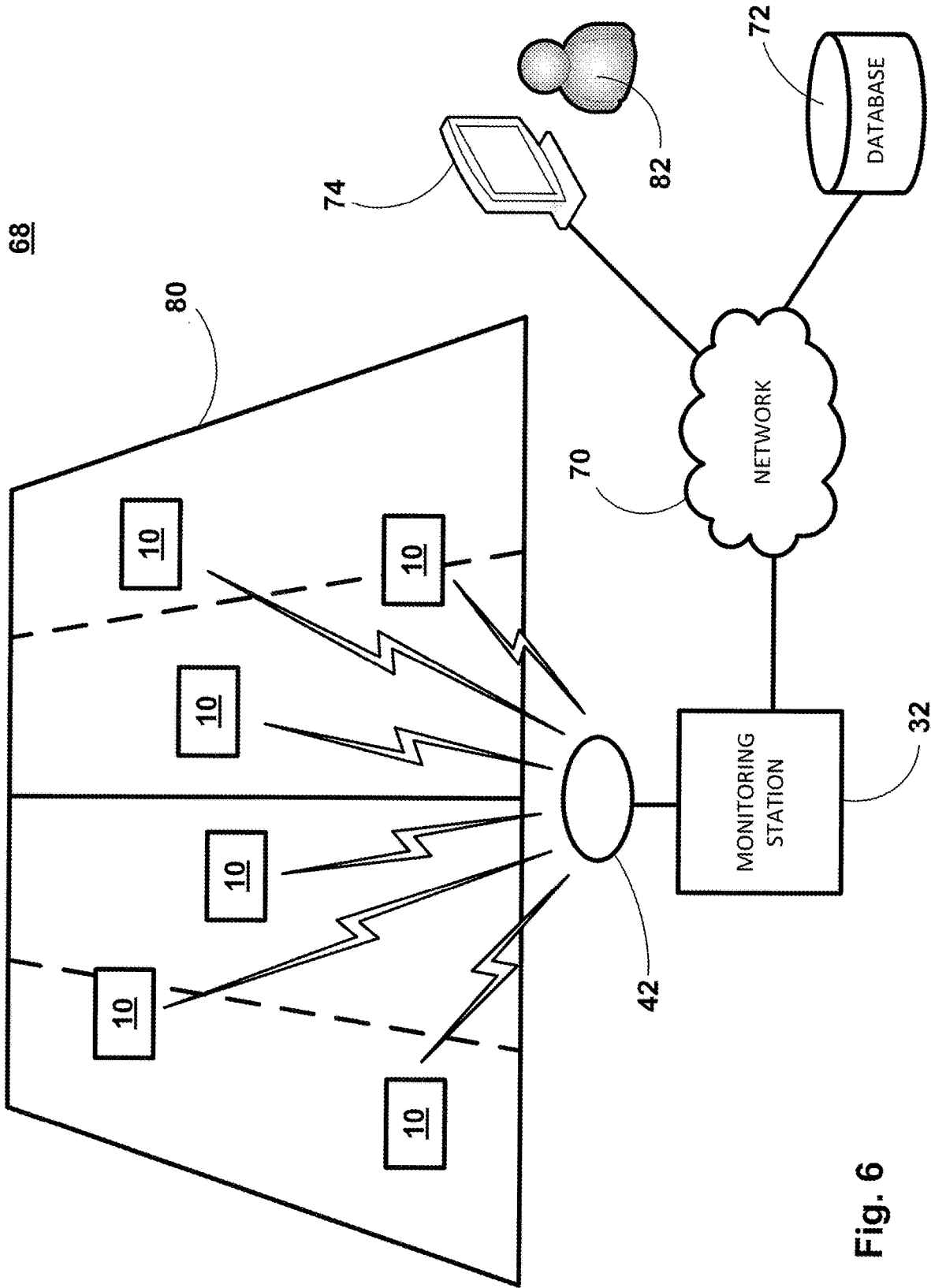
FIG. 6 illustrates an example environment where an impact assessment system comprising one or more mouth-guards according to one or more embodiments of the present disclosure may be employed.

FIG. 5 illustrates an impact assessment system 68 where impacts sustained by participants may be detected, recorded, analyzed, and reviewed, and FIG. 6 illustrates an example environment where the impact assessment system of FIG. 5 may be employed.

The impact assessment system 68 is operative to aggregate data representative of acceleration experienced by participants, i.e. the data received from the systems for monitoring acceleration 28 in mouth-guards 10 worn by participants, and can make the data available to relevant parties.

One or more participants are fitted with a mouth-guard 10 comprising a system for monitoring acceleration 28 as described above. A monitoring station 32 (as described above) is located near to a field-of play so as to be within communication range of each system for monitoring acceleration 28. The monitoring station 32 is operative to receive data signals from each system for monitoring acceleration 28, with such data signals comprising data representative of acceleration experienced by each participant fitted with the mouth-guard 10.

The monitoring station 32 is in wireless communication with the one or more systems for monitoring acceleration 28 in the mouth-guards 10.

The monitoring station 32 is optionally in wired or wireless communication with a network 70 (e.g. a public or private data network). The network 70 is communicatively coupled (wired and/or wirelessly) to a database 72 and/or one or more user devices (such as, for example, a computer 74, a tablet device 76 and/or a smartphone 78).

Data received by the monitoring station 32 is analyzed and converted to a format that is suitable for presentation via a display of the one or more user devices. Data presented in this manner can be analyzed by a technician 82 (see FIG. 6) to assess participant well-being and, based upon the data, to make a determination whether or not a participant should be removed from the field-of-play 80 (see FIG. 6) following an impact event, or may continue to participate.

Also, data received by the monitoring station is communicated to the database 72 for storage. Data stored in this manner may be retrievable at a later time for review by a technician.

The antenna 42 (see FIG. 6) of the monitoring station 32 is located in proximity to a field-of-play 80 so as to receive data signals from systems for monitoring acceleration within mouth-guards 10 worn by participants on the field-of-play 80.

The antenna 42 of the monitoring station 32, in an example, comprises a directional dual-polarized antenna positioned such that it is configured for the reception of data signals from the systems for monitoring acceleration within mouth-guards 10, regardless of their physical orientation.

Typically, the directional dual-polarized antenna is configured to favour receipt of signals from systems for monitoring acceleration within mouth-guards 10 on the field-of-play 80 rather than from systems off the field-of-play, such as, for example, those worn and/or carried by potential participants (e.g. substitutes, or reserves), coaches, and/or other team staff located on the side-line of the field-of-play 80.

The antenna 42 typically comprises an omni-directional antenna capable of receiving signals so as to provide coverage of an entire field-of-play 80.

The system for monitoring acceleration 28 is typically formed from components mounted on a printed circuit board. The dimensions of the system for monitoring acceleration are optimized to achieve as small a foot-print as possible. This is to improve the integrity of a portion of the mouth-guard 10 where the system for monitoring acceleration 28 is located.

As will be appreciated, the system for monitoring acceleration 28, when encapsulated within material of the mouth-guard 10, is effectively sandwiched between material extending inwardly from a first surface of a wall in which the system for monitoring acceleration 28 is encapsulated and material extending inwardly from a second, opposed surface of the wall in which the system for monitoring acceleration 28 is encapsulated. A larger surface area of the system for monitoring acceleration 28 decreases the amount of material in contact between the opposed first and second surfaces. Therefore, by optimizing the dimensions of the system for monitoring acceleration 28, so as to decrease the foot-print, there will be an increase in the amount of material in contact between the opposed first and second surfaces. As a result, a weakness of the portion of the mouth-guard 10 where the system for monitoring acceleration 28 is encapsulated may be reduced (includes reduced air pockets and delamination). Thus, instances of failure of this portion during an impact (e.g. when a wearer may clench together the teeth of the upper and lower jaws, thereby increasing pressure on the mouth-guard 10) may be reduced.

Minimising the footprint of electronic components of the system for monitoring acceleration and boards carrying them may improve the integrity of the mouth-guard 10, because the volume of the mouth-guard 10 that is not occupied by material from which the mouth-guard 10 is formed is minimized. In particular, the space between external surfaces (i.e. first and second surfaces) of the wall of the mouth-guard 10 in which the system for monitoring acceleration 28 is encapsulated may be lessened, if the circuit board is smaller. This may improve the creation of a vacuum in the vacuum forming process and thus improve integrity of the mouth-guard 10. Specific implementations may include splitting the circuit board up to have smaller circuit board elements. Thus, although the system for monitoring acceleration 28 is represented by a single unit in the figures, it may, in optional arrangements, comprise multiple units, which are electrically coupled.

Also, minimizing the footprint of electronic components of the system for monitoring force and boards carrying them may provide for a more comfortable mouth-guard, because there are smaller deformities (from the electronic components) compared with known types of mouth-guards.

In the above described one or more embodiments data representative of impact events is transmitted to the monitoring station in real-time. However, optionally the data may be stored in memory on-board the mouth-guard for transmission at particular intervals, or may be stored for download at a later time.

In the above described one or more embodiments, the acceleration monitoring unit 44 comprises a gyroscope unit 54. However, optionally the gyroscope 54 may be replaced by an inertial measurement unit comprising a gyroscope, a magnetometer, and an accelerometer. An inertial measurement unit of this nature may be available in a single package and may comprise an LSM9DS1 microelectromechanical system (MEMS) from an iNEMO inertial module range, produced by STMicroelectronics of 39, Chemin du Champ des Filles Plan-Les-Ouates, Geneva, CH 1228, Switzerland.

Optionally, the accelerometer 52 of acceleration monitoring unit 44 comprises a H3LIS331DL MEMS motion sensor produced by STMicroelectronics of 39, Chemin du Champ des Filles Plan-Les-Ouates, Geneva, CH 1228, Switzerland.

In the above described one or more embodiments, the first, second and third walls 14, 16, 18 of body 12 define a channel 20 for receiving a plurality of teeth of a wearer, with the channel 20 structured so as to cover teeth that include the incisors of a wearer when the mouth-guard 10 is inserted. Optionally, it may be desirable to cover only parts of at least one of vestibular, palatal, incisal and occlusal surfaces in other arrangements, and so the mouth-guard may be configured to provide appropriate levels of surface cover as required.

In the above described one or more embodiments, the mouth-guard 10 comprises a body 12 that defines a formation to be located around at least a portion of maxillary teeth of a wearer (i.e. teeth in the upper jaw of the wearer), to cover, surround, and/or envelope the upper teeth of the wearer. Optionally, the mouth-guard 10 may comprise a body that defines a formation to be located around at least a portion of mandibular teeth of a wearer (i.e. teeth in the lower jaw of the wearer), to cover, surround, and/or envelope the lower teeth of the wearer. Further optionally, the mouth-guard 10 may be locatable around at least a portion of both maxillary and mandibular teeth of a wearer.

In the above described one or more embodiments, the mouth-guard 10 comprises an open area 24. Optionally, the space between the two arms may comprise a solid portion that covers the upper palate.

In the above described one or more embodiments, the memory 46 and transceiver 48 are shown as separate units from the acceleration monitoring unit 44. Optionally, the memory 46 and transceiver 48 may form part of a same device as the acceleration monitoring unit 44, e.g. a single unit comprising the acceleration monitoring unit 44, the memory 46 and the transceiver 48. Further optionally, the accelerometer 52, gyroscope unit 54, processor 56, memory 46 and transceiver 48 may be combined on multiple units in any combination. Yet further optionally, the accelerometer 52, gyroscope unit 54, processor 56, memory 46 and transceiver 48 may comprise individual, discrete units.

In the above described one or more embodiments, each of the acceleration monitoring unit 44 and the gyroscope unit 54 are communicatively coupled to the processor 56 by way of Inter-Integrated Circuit (I2C) buses 58, 60 respectively. Optionally, communicative coupling of the acceleration monitoring unit 44 and the gyroscope unit 54 to the processor 56 may be by any other suitable communication interface, e.g. Serial Peripheral Interface bus.

In the above described one or more embodiments, system for monitoring acceleration 28 is typically formed from components mounted on a printed circuit board. The printed circuit board may optionally comprise a flex-printed circuit and/or a rigid circuit board. In an optional arrangement, the printed circuit board may comprise both flexible portions and rigid portions, e.g. components of the system mounted on rigid portions with rigid portions connected to one another by flexible portions (i.e. a flex-rigid arrangement). In another optional arrangement, the printed circuit board may comprise both rigid portions on which components of the system are mounted, with the rigid portions connected to one another by flexible electrical wire.

Optionally, the memory 46 may comprise flash memory and/or RAM and/or ROM.

In the above described one or more embodiments, the power source 26 and system for monitoring acceleration 28 are located in a portion of the same arm of the mouth-guard. Optionally, they may be located in different arms of the mouth-guard. Further optionally, there may be a plurality of power sources and/or systems for monitoring acceleration located in the mouth-guard in the same arm, different arms, or both arms. Yet further optionally, the power source 26 and system for monitoring acceleration 28 may be located in the same wall in the same arm, different walls in the same arm, the same wall in different arms, or different walls in different arms.

In the above described one or more embodiments, the components of the mouth-guard are encapsulated (i.e. wholly embedded) within material forming the mouth-guard 10. Optionally, one or more of the components may be embedded, or partially encapsulated in the material forming the mouth-guard 10. Further optionally, the one or more components may be encapsulated within a second material, optionally a medically inert material (e.g. parylene C). The one or more components encapsulated with the second material may be partially embedded, or wholly embedded, within the material forming the mouth-guard 10.

Although the acceleration monitoring unit 44 includes a three axis accelerometer 52 and a three axis gyroscope unit 54 in the one or more embodiments described above, optionally other acceleration monitoring components may be used in other embodiments. For example, a two axis gyroscope in combination with a single axis gyroscope may be used instead of a three axis gyroscope. Also, a two axis accelerometer in combination with a single axis accelerometer may be used instead of a three axis accelerometer. Further, additional linear accelerometers may be used instead of a gyroscope.

In the above described one or more embodiments, the system for monitoring acceleration 28 and power source 26 may comprise separate elements, which are electrically connected by a connection lead. Optionally, the connection lead may comprise the antenna 50 of the system for monitoring acceleration 28, there being a high frequency/radio frequency coupling to the connection lead.

In the above described one or more embodiments, the antenna 42 comprises an omni-directional antenna so as to provide coverage of an entire field-of-play. Optionally, other antennas may be used e.g. with a narrower range of receiving angles. For example, multiple antennas with directionalities that individually do not allow for reception of signals from the entire field-of-play, but in combination receive signals from the entire field-of play may be used. For example, four antennas located at each corner of the field-of-play may be used to cover the entire field. This arrangement may also provide redundancy in the system so that, if a signal fails to be received by a closest antenna, it could, potentially, be received by another one of the four antennas.

All references made herein to orientation (e.g. front, rear, upper, lower, anterior and posterior) are made for the purposes of describing relative spatial arrangements of features, and are not intended to be limiting in any sense.

It will be understood by those skilled in the art that the drawings are merely diagrammatic and that further items of equipment may be required in a commercial apparatus. The position of such ancillary items of equipment forms no part of the present disclosure and is in accordance with conventional practice in the art.

Insofar as embodiments of the disclosure described above are implementable, at least in part, using a software-controlled programmable processing device such as a general purpose processor or special-purposes processor, digital signal processor, microprocessor, or other processing device, data processing apparatus or computer system it will be appreciated that a computer program for configuring a programmable device, apparatus or system to implement methods and apparatus is envisaged as an aspect of the present disclosure. The computer program may be embodied as any suitable type of code, such as source code, object code, compiled code, interpreted code, executable code, static code, dynamic code, and the like. The instructions may be implemented using any suitable high-level, low-level, object-oriented, visual, compiled and/or interpreted programming language, such as, Liberate, OCAP, MHP, Flash, HTML and associated languages, JavaScript, PHP, C, C++, Python, Nodejs, Java, BASIC, Perl, Matlab, Pascal, Visual BASIC, ActiveX, assembly language, machine code, and so forth. A skilled person would readily understand that term "computer" in its most general sense encompasses programmable devices such as referred to above, and data processing apparatus and computer systems.

Suitably, the computer program is stored on a carrier medium in machine readable form, for example the carrier medium may comprise memory, removable or non-removable media, erasable or non-erasable media, writeable or re-writeable media, digital or analog media, hard disk, floppy disk, Compact Disk Read Only Memory (CD-ROM), Company Disk Recordable (CD-R), Compact Disk Rewriteable (CD-RW), optical disk, magnetic media, magneto-optical media, removable memory cards or disks, various types of Digital Versatile Disk (DVD) subscriber identity module, tape, cassette solid-state memory.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the disclosure. This is done merely for convenience and to give a general sense of the disclosure. This description should be read to include one or at least one and the singular also includes the plural unless it is obvious that it is meant otherwise.

In view of the foregoing description it will be evident to a person skilled in the art that various modifications may be made within the scope of the disclosure.

For example, although embodiments have been described in which impact event data may be transmitted to a monitoring station in real-time, impact event data may be stored and downloaded wirelessly, or by wired coupling, at breaks in a match, e.g. half-time, or at the end of the match. This may be particularly suitable for non-professional environments and download may be to a device such as a smartphone or other mobile communication device running a suitable application.

One or more embodiments have been described in the context of acceleration monitoring. Optionally, monitoring circuitry, power sources and transmitter and/or receiver circuitry may be included for monitoring other factors such as, for example, physiological data, for example, hydration, temperature, electrolyte levels, amongst other things.

The scope of the present disclosure includes any novel feature or combination of features disclosed therein either explicitly or implicitly or any generalisation thereof irrespective of whether or not it relates to the claimed disclosure or mitigate against any or all of the problems addressed by the present disclosure. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

Concerning another aspect of the present disclosure, a mouth-guard (or gum-shield) is a piece of protective equipment worn by participants in sports, particularly contact sports. A mouth-guard is typically worn in an upper part of the mouth of the participant and is generally configured to cover at least a portion of the upper teeth of the participant. Most typically, a mouth-guard is configured to cover at least a portion of a vestibular (outer) surface of upper teeth of the wearer, at least a portion of a palatal (inner) surface of upper teeth of the wearer, and at least a portion of incisal and occlusal surfaces (i.e. "biting" and "chewing" surfaces) of upper teeth of the wearer.

In general outline, a mouth-guard according to one or more embodiments of the present disclosure can form a part of a system for the detection, measurement, characterisation, transmission, and/or reporting of impact events causing acceleration to be experienced by participants. Sensor components and/or monitoring element components located in the mouth-guard are used to monitor accelerations experienced by participants and data representative of such accelerations can be conveyed to a monitoring station for review by a technician, for example, a trained medical professional. This can allow the technician to make a decision regarding whether or not a participant in a sports match is fit to continue playing (e.g. following a particularly heavy head impact event) or should be removed from play and referred for further testing with a medical professional.

In the present description, the phrase "head impact event" relates to both direct impacts to the head and indirect impacts. That is, where the head receives a blow directly, or when a blow is sustained to some other body part and the force of the blow causes, amongst other things, an acceleration of the head. Further, reference is made to a participant sustaining an impact and their head experiencing an acceleration because of the impact. The acceleration of the head may be as a result of an impact directly to the head (i.e. a force is exerted on the head directly), or as result of an impact to another part of the body, but the result of which is that force is transmitted to the head from the point-of-impact through the body and neck. Such an acceleration may be termed an impact acceleration.

The sensor and/or monitoring element components are embedded and/or encapsulated in material from which the mouth-guard is formed.

FIG. 1 illustrates a mouth-guard 10 according to one or more embodiments of the present disclosure in which embedded and/or encapsulated components are arranged in a first arrangement. FIG. 2 illustrates a mouth-guard 10 according to one or more embodiments of the present disclosure in which embedded and/or encapsulated components are arranged in a second arrangement.

In the illustrated mouth-guard 10 of FIGS. 1 and 2, components are shown positioned in walls of the mouth-guard that are locatable at the rear of a mouth of a wearer when the mouth-guard is located correctly in the mouth.

The components are connected electronically by means of wires or circuit board (which may be flexible) and are communicatively coupled to a transceiver for transmitting data received from the components to a monitoring station in real-time. These components operate to collect and process impact event data, which can then be transmitted to the monitoring station via the transceiver.

Various terms used in dentistry are used in describing the mouth-guard 10 of one or more embodiments of the present disclosure. The terms used in this disclosure are listed below:

Anterior—The direction towards the front of the head or the lips, as opposed to posterior, which refers to the directions towards the back of an individual's head. The term anterior teeth refers to incisors and canines, as opposed to premolars and molars, which are posterior teeth;

Distal—The direction towards the gums beyond the tooth furthest from the midline (i.e. the 'most posterior tooth' or last tooth) in each quadrant of a dental arch, as opposed to mesial, which refers to the direction towards the midline;

Incisal—The direction towards the biting edge of front teeth. This is a related term to occlusal, which relates to the analogous location on rear teeth;

Mandibular—Relating to the mandible, or lower jaw;

Maxillary—Relating to the maxilla, or upper jaw;

Mesial—The direction towards the midline in a dental arch, as opposed to distal, which refers to the direction towards the gums beyond the tooth furthest from the anterior midline (the 'most posterior tooth' or last tooth) in each quadrant;

Midline—Roughly, an imaginary vertical line dividing the left and right sides of the mouth at the teeth;

Occlusal—The direction towards the biting surface of rear teeth. This is a related term to incisal, which relates to the analogous location on anterior teeth;

Palatal—The side of a tooth adjacent to (or the direction towards) the palate, as opposed to vestibular, which refers to the side of a tooth adjacent to (or the direction towards) the inside of the cheek or lips of the mouth respectively;

Posterior—The direction towards the back of an individual's head, as opposed to anterior, which refers to the directions towards an individual's lips. The term posterior teeth refers to premolars and molars, as opposed to incisors and canines, which are anterior teeth;

Quadrant—The arrangement of teeth in a mouth is divided into four quarters. Upper and lower sets of teeth form an oval, which is divided into quadrants:
Upper right quadrant: upper right first incisor to upper right wisdom tooth;
Upper left quadrant: upper left first incisor to upper left wisdom tooth;
Lower right quadrant: lower right first incisor to lower right wisdom tooth;
Lower left quadrant: lower left first incisor to lower left wisdom tooth; and Vestibular—The side of a tooth that is adjacent to (or the direction towards) the inside of the cheeks and lips, as opposed palatal, which refers to the side of a tooth adjacent to the palate.

Additionally, reference is made to monitoring acceleration. In at least some implementations, a device used to measure acceleration is termed an "accelerometer". The terms "acceleration measurement", "acceleration monitoring" and the like include use of devices known as "accelerometers". The terms may be used interchangeably depending on context.

As illustrated in FIGS. 1 and 2, the mouth-guard 10 comprises a body 12 that defines a formation to be located around at least a portion of maxillary teeth of a wearer (i.e. teeth in the upper jaw of the wearer—hereinafter "upper teeth"), to cover, surround, and/or envelope the upper teeth of the wearer.

The body 12, formed from a plastics, resin, and/or rubber material, comprises a first wall 14 configured to cover at least a portion of an outer surface of the upper teeth of the wearer (i.e. the surface of the upper teeth that faces the inside of the upper lip and the cheek). In dentistry terminology this surface is known as a vestibular surface.

The body 12 comprises a second wall 16 configured to cover at least a portion of an inner surface of the upper teeth of the wearer (i.e. the surface of the upper teeth that faces the palate). In dentistry terminology this surface is known as a palatal surface. The body 12 comprises a third wall 18 connecting the first and second walls 14, 16 and configured to cover at least a portion of biting edges and chewing surfaces of the upper teeth of the wearer (i.e. the edges and surfaces of the upper teeth that are opposed to the lower teeth). In dentistry terminology, these surfaces are known as incisal and occlusal surfaces.

The first, second and third walls 14, 16, 18 of body 12 define a channel 20 for receiving a plurality of teeth of a wearer. In the illustrated examples of FIGS. 1 and 2, the channel 20 is structured such that, when worn, it covers teeth that include the incisors of a wearer when the mouth-guard 10 is inserted.

In plan view, the body 12 of the mouth-guard 10 presents a generally symmetrical U-shaped configuration with "arms" extending away from a mid-line (denoted by dashed line 22 in FIGS. 1 and 2). The first, second and third walls 14, 16, 18 in one arm define a portion of the channel 20 that can receive teeth of an upper left quadrant. The first, second and third walls 14, 16, 18 in the other arm define a portion of the channel 20 that can receive teeth of an upper right quadrant.

The mouth-guard 10 also defines an open area 24, located between the two arms, which can allow a tongue of the wearer to touch their upper palate when the mouth-guard 10 is being worn. This may allow the user to maintain verbal communication with other participants (e.g. teammates) without requiring removal of the mouth-guard.

The mouth-guard 10 includes a power source 26 (e.g. an electrical power battery) that is electrically connected to a system for monitoring acceleration 28. Typically, the power source 26 is of a type compatible with a wireless charger to allow recharging of the power source, i.e. the power source 26 may be wirelessly rechargeable, which allows the power source 26 to be charged/recharged without requiring removal from the mouth-guard 10.

In the illustrated example of FIG. 1, the power source 26 and system for monitoring acceleration 28 are located in a portion of the same arm of the mouth-guard. The portion in which they are located is in a distal direction from the mid-line 22. The power source 26 is located in the second wall 16 and the system for monitoring acceleration 28 is located in the first wall 14. The power source 26 and system for monitoring acceleration 28 are electrically connected using a suitable connection (not shown) that runs from the power source 26, through the third wall 18 to the system for monitoring acceleration 28.

Locating the power source 26 and system for monitoring acceleration 28 in a distal direction away from the mid-line 22 (i.e. so that these components are located in a portion of the mouth-guard 10 that is located in a rear part of the mouth of the wearer, when worn) may reduce the likelihood of damage to the power source 26, system for monitoring acceleration 28 and/or teeth when the wearer sustains an impact. For instance, if the wearer undergoes a collision where a point of impact is at the front of the face of the wearer (e.g. at, or around, the mid-line of the upper teeth of the wearer), then damage to the power source 26 and/or system for monitoring acceleration 28 may be inhibited, because these components are located at positions away from the point of impact. Locating the power source 26 and/or system for monitoring acceleration 28 away from points of likely impact may reduce the likelihood of damage to teeth, because the "hard" bodies making up the housings of the power source 26 and/or system for monitoring acceleration 28 are in positions where they are less likely to be forced into the teeth.

Optionally, the power source 26 and/or system for monitoring acceleration 28 may be located in a different area of the mouth-guard 10 in one or more embodiments. FIG. 2 illustrates another example, in which the power source 26 and system for monitoring acceleration 28 are, again, located in a portion of the same arm of the mouth-guard. The portion in which they are located is in a distal direction from the mid-line 22. However, in the example illustrated in FIG. 2, both the power source 26 and the system for monitoring acceleration 28 are located in the second wall 18.

In a mouth-guard 10 of the type illustrated in FIG. 2, likelihood of damage to the power source 26 and/or system for monitoring acceleration 28 when the wearer sustains an impact to the head may be reduced not only because the power source 26 and system for monitoring acceleration 28 are located in the mouth-guard 10 in a distal direction away from the mid-line 22 (i.e. so that these components are located in a portion of the mouth-guard 10 that is located in a rear part of the mouth of the wearer, when worn), but also because the power source 26 and system for monitoring acceleration 28 are located in a portion of the mouth-guard 10 that is locatable inside (i.e. on a palatal side of) the upper teeth. The teeth themselves can serve as a barrier to offer a level of protection to the components. In addition to the potential to inhibit damage during frontal impacts, the location of the components in the example of FIG. 2 may, in an instance where the wearer undergoes a collision where a point of impact is at the side of the face, inhibit damage to the power source 26 and/or system for monitoring acceleration 28, because these components are located at positions in which they are shielded, at least in part, by the teeth of the wearer.

In the illustrated examples of FIGS. 1 and 2, the components of the mouth-guard 10, described above, are encapsulated (i.e. wholly embedded) within material forming the mouth-guard 10.

FIG. 3 illustrates a system 30 for providing a monitoring environment for monitoring acceleration sustained by participants in a sporting event.

The system 30 operates to aggregate data representative of acceleration that occurs during impact events, the data being received from systems for monitoring acceleration 28 in mouth-guards 10 worn by game participants. The data can be conveyed to technicians, via the system, for assessing the seriousness of one or more impact events.

The system 30 comprises a monitoring station 32 that is in wireless communication with one or more systems for monitoring acceleration 28. The monitoring station 32 can communicate data received from the one or more systems for monitoring acceleration 28 to one or more devices (not shown in FIG. 3—see FIG. 5) either wirelessly or by wired communication link.

The monitoring station 32 includes a processor 34, a user interface 36, memory 38, and a transceiver 40. The monitoring station 32 wirelessly receives data representative of accelerations experienced by participants from each of the systems for monitoring acceleration 28. Signals from each of the systems for monitoring acceleration 28 are received at an antenna 42 coupled to the transceiver 40. The received signals are passed to the processor 34, which operates to process the data. Processed data is communicated to memory 38 for storage and can also be communicated to user interface 36, which is configured for communicating the data to a display device (e.g. via a communications network).

FIG. 4 illustrates components of the mouth-guard 10 (e.g. the power source 26 and the system for monitoring acceleration 28) in more detail.

The system for monitoring acceleration 28 comprises an acceleration monitoring unit 44, a memory 46 and a transceiver 48. The acceleration monitoring unit 44 is operative to monitor acceleration experienced by a wearer of the mouth-guard 10, and is electrically coupled to the memory 46, which serves to store data representative of acceleration monitored by the acceleration monitoring unit 44. The acceleration monitoring unit 44 is also electrically coupled to the transceiver 48, which is operative to communicate a data signal containing data representative of acceleration monitored by the system for monitoring acceleration to the monitoring station 32 via antenna 50. Data can also be received by the system for monitoring acceleration 28 from an external source via the antenna 50 and transceiver 48. Received data may comprise, for example, a negative-acknowledgement signal (e.g. to indicate an error in data previously sent from the system for monitoring acceleration 28 and to request that the data be re-sent), software updates, etc.

The acceleration monitoring unit 44 comprises a three axis linear accelerometer 52, an gyroscope unit 54 and a processor 56. Each of the acceleration monitoring unit 44 and the gyroscope unit 54 are communicatively coupled to the processor 56 by way of Inter-Integrated Circuit (I²C) buses 58, 60 respectively.

The accelerometer 52 is operative to monitor linear accelerations of the mouth-guard 10. The accelerometer 52 is operative to measure a linear acceleration in each orthogonal direction (x, y, z), e.g. of a Cartesian coordinate reference frame. A combination of respective acceleration values may be used to derive a linear acceleration vector.

The gyroscope unit 54 is operative to measure angular velocity to provide data representative of angular rotation. The gyroscope unit 54 is operative to measure angular velocity with respect to each orthogonal direction (x, y, z), e.g. of a Cartesian coordinate reference frame. A combination of respective angular velocity values may be used to derive an angular velocity vector.

The accelerometer 52 and gyroscope unit 54 are operative to monitor attributes of the environment of the mouth-guard 10 over time to determine a linear acceleration of the system for monitoring acceleration 28 and an angular velocity of the system for monitoring acceleration 28. Using data indicative of linear acceleration and angular velocity, which is communicated to the processor 56, the processor 56 is able to determine the fact of an event causing acceleration of a particular magnitude and a rotation. This data can be used in the system for monitoring acceleration 28 and/or the monitoring station 32, to calculate a vector representative of a magnitude of the linear acceleration and a vector representative of an angular velocity experienced by the system for monitoring acceleration 28.

FIG. 5 illustrates an impact assessment system 68 where impacts sustained by participants may be detected, recorded, analyzed, and reviewed, and FIG. 6 illustrates an example environment where the impact assessment system of FIG. 5 may be employed.

The impact assessment system 68 is operative to aggregate data representative of acceleration experienced by participants, i.e. the data received from the systems for monitoring acceleration 28 in mouth-guards 10 worn by participants, and can make the data available to relevant parties.

One or more participants are fitted with a mouth-guard 10 comprising a system for monitoring acceleration 28 as described above. A monitoring station 32 (as described above) is located near to a field-of play so as to be within communication range of each system for monitoring acceleration 28. The monitoring station 32 is operative to receive data signals from each system for monitoring acceleration 28, with such data signals comprising data representative of acceleration experienced by each participant fitted with the mouth-guard 10.

The monitoring station 32 is in wireless communication with the one or more systems for monitoring acceleration 28 in the mouth-guards 10.

The monitoring station 32 is optionally in wired or wireless communication with a network 70 (e.g. a public or private data network). The network 70 is communicatively coupled (wired and/or wirelessly) to a database 72 and/or one or more user devices (such as, for example, a computer 74, a tablet device 76 and/or a smartphone 78).

Data received by the monitoring station 32 is analyzed and converted to a format that is suitable for presentation via a display of the one or more user devices. Data presented in this manner can be analyzed by a technician 82 (see FIG. 6) to assess participant well-being and, based upon the data, to make a determination whether or not a participant should be removed from the field-of-play 80 (see FIG. 6) following an impact event, or may continue to participate.

Also, data received by the monitoring station is communicated to the database 72 for storage. Data stored in this manner may be retrievable at a later time for review by a technician.

The antenna 42 (see FIG. 6) of the monitoring station 32 is located in proximity to a field-of-play 80 so as to receive data signals from systems for monitoring acceleration within mouth-guards 10 worn by participants on the field-of-play 80.

The antenna 42 of the monitoring station 32, in an example, comprises a directional dual-polarized antenna positioned such that it is configured for the reception of data signals from the systems for monitoring acceleration within mouth-guards 10, regardless of their physical orientation.

Typically, the directional dual-polarized antenna is configured to favour receipt of signals from systems for monitoring acceleration within mouth-guards 10 on the field-of-play 80 rather than from systems off the field-of-play, such as, for example, those worn and/or carried by potential participants (e.g. substitutes, or reserves), coaches, and/or other team staff located on the side-line of the field-of-play 80.

The antenna 42 typically comprises an omni-directional antenna capable of receiving signals so as to provide coverage of an entire field-of-play 80.

The system for monitoring acceleration 28 is typically formed from components mounted on a printed circuit board. The dimensions of the system for monitoring acceleration are optimized to achieve as small a foot-print as possible. This is to improve the integrity of a portion of the mouth-guard 10 where the system for monitoring acceleration 28 is located.

As will be appreciated, the system for monitoring acceleration 28, when encapsulated within material of the mouth-guard 10, is effectively sandwiched between material extending inwardly from a first surface of a wall in which the system for monitoring acceleration 28 is encapsulated and material extending inwardly from a second, opposed surface of the wall in which the system for monitoring acceleration 28 is encapsulated. A larger surface area of the system for monitoring acceleration 28 decreases the amount of material in contact between the opposed first and second surfaces. Therefore, by optimizing the dimensions of the system for monitoring acceleration 28, so as to decrease the foot-print, there will be an increase in the amount of material in contact between the opposed first and second surfaces. As a result, a weakness of the portion of the mouth-guard 10 where the system for monitoring acceleration 28 is encapsulated may be reduced (includes reduced air pockets and delamination). Thus, instances of failure of this portion during an impact (e.g. when a wearer may clench together the teeth of the upper and lower jaws, thereby increasing pressure on the mouth-guard 10) may be reduced.

Minimising the footprint of electronic components of the system for monitoring acceleration and boards carrying them may improve the integrity of the mouth-guard 10, because the volume of the mouth-guard 10 that is not occupied by material from which the mouth-guard 10 is formed is minimized. In particular, the space between external surfaces (i.e. first and second surfaces) of the wall of the mouth-guard 10 in which the system for monitoring acceleration 28 is encapsulated may be lessened, if the circuit board is smaller. This may improve the creation of a vacuum in the vacuum forming process and thus improve integrity of the mouth-guard 10. Specific implementations may include splitting the circuit board up to have smaller circuit board elements. Thus, although the system for monitoring acceleration 28 is represented by a single unit in the figures, it may, in optional arrangements, comprise multiple units, which are electrically coupled.

Also, minimizing the footprint of electronic components of the system for monitoring force and boards carrying them may provide for a more comfortable mouth-guard, because there are smaller deformities (from the electronic components) compared with known types of mouth-guards.

In the above described one or more embodiments data representative of impact events is transmitted to the monitoring station in real-time. However, optionally the data may be stored in memory on-board the mouth-guard for transmission at particular intervals, or may be stored for download at a later time.

In the above described one or more embodiments, the acceleration monitoring unit 44 comprises a gyroscope unit 54. However, optionally the gyroscope 54 may be replaced by an inertial measurement unit comprising a gyroscope, a magnetometer, and an accelerometer. An inertial measurement unit of this nature may be available in a single package and may comprise an LSM9DS1 (hereinafter "LSM" gyroscope") microelectromechanical system (MEMS) from an iNEMO inertial module range, produced by STMicroelectronics of 39, Chemin du Champ des Filles Plan-Les-Ouates, Geneva, CH 1228, Switzerland.

Optionally, the accelerometer 52 of acceleration monitoring unit 44 comprises a H3LIS331DL MEMS motion sensor (hereinafter "H3LIS accelerometer") produced by STMicroelectronics of 39, Chemin du Champ des Filles Plan-Les-Ouates, Geneva, CH 1228, Switzerland. In the above described one or more embodiments, the first, second and third walls 14, 16, 18 of body 12 define a channel 20 for receiving a plurality of teeth of a wearer, with the channel 20 structured so as to cover teeth that include the incisors of a wearer when the mouth-guard 10 is inserted. Optionally, it may be desirable to cover only parts of at least one of vestibular, palatal, incisal and occlusal surfaces in other arrangements, and so the mouth-guard may be configured to provide appropriate levels of surface cover as required.

In the above described one or more embodiments, the mouth-guard 10 comprises a body 12 that defines a formation to be located around at least a portion of maxillary teeth of a wearer (i.e. teeth in the upper jaw of the wearer), to cover, surround, and/or envelope the upper teeth of the wearer. Optionally, the mouth-guard 10 may comprise a body that defines a formation to be located around at least a portion of mandibular teeth of a wearer (i.e. teeth in the lower jaw of the wearer), to cover, surround, and/or envelope the lower teeth of the wearer. Further optionally, the mouth-guard 10 may be locatable around at least a portion of both maxillary and mandibular teeth of a wearer.

In the above described one or more embodiments, the mouth-guard 10 comprises an open area 24. Optionally, the space between the two arms may comprise a solid portion that covers the upper palate.

In the above described one or more embodiments, the memory 46 and transceiver 48 are shown as separate units from the acceleration monitoring unit 44. Optionally, the memory 46 and transceiver 48 may form part of a same device as the acceleration monitoring unit 44, e.g. a single unit comprising the acceleration monitoring unit 44, the memory 46 and the transceiver 48. Further optionally, the accelerometer 52, gyroscope unit 54, processor 56, memory 46 and transceiver 48 may be combined on multiple units in any combination. Yet further optionally, the accelerometer 52, gyroscope unit 54, processor 56, memory 46 and transceiver 48 may comprise individual, discrete units.

In the above described one or more embodiments, each of the acceleration monitoring unit 44 and the gyroscope unit 54 are communicatively coupled to the processor 56 by way of Inter-Integrated Circuit (I2C) buses 58, 60 respectively. Optionally, communicative coupling of the acceleration monitoring unit 44 and the gyroscope unit 54 to the processor 56 may be by any other suitable communication interface, e.g. Serial Peripheral Interface bus.

In the above described one or more embodiments, system for monitoring acceleration 28 is typically formed from components mounted on a printed circuit board. The printed circuit board may optionally comprise a flex-printed circuit and/or a rigid circuit board. In an optional arrangement, the printed circuit board may comprise both flexible portions and rigid portions, e.g. components of the system mounted on rigid portions with rigid portions connected to one another by flexible portions (i.e. a flex-rigid arrangement). In another optional arrangement, the printed circuit board may comprise both rigid portions on which components of the system are mounted, with the rigid portions connected to one another by flexible electrical wire.

Optionally, the memory 46 may comprise flash memory and/or RAM and/or ROM.

In the above described one or more embodiments, the power source 26 and system for monitoring acceleration 28 are located in a portion of the same arm of the mouth-guard. Optionally, they may be located in different arms of the mouth-guard. Further optionally, there may be a plurality of power sources and/or systems for monitoring acceleration located in the mouth-guard in the same arm, different arms, or both arms. Yet further optionally, the power source 26 and system for monitoring acceleration 28 may be located in the same wall in the same arm, different walls in the same arm, the same wall in different arms, or different walls in different arms.

In the above described one or more embodiments, the components of the mouth-guard are encapsulated (i.e. wholly embedded) within material forming the mouth-guard 10. Optionally, one or more of the components may be embedded, or partially encapsulated in the material forming the mouth-guard 10. Further optionally, the one or more components may be encapsulated within a second material, optionally a medically inert material (e.g. parylene C). The one or more components encapsulated with the second material may be partially embedded, or wholly embedded, within the material forming the mouth-guard 10.

Although the acceleration monitoring unit 44 includes a three axis accelerometer 52 and a three axis gyroscope unit 54 in the one or more embodiments described above, optionally other acceleration monitoring components may be used in other embodiments. For example, a two axis gyroscope in combination with a single axis gyroscope may be used instead of a three axis gyroscope. Also, a two axis accelerometer in combination with a single axis accelerometer may be used instead of a three axis accelerometer. Further, additional linear accelerometers may be used instead of a gyroscope.

In the above described one or more embodiments, the system for monitoring acceleration 28 and power source 26 may comprise separate elements, which are electrically connected by a connection lead. Optionally, the connection lead may comprise the antenna 50 of the system for monitoring acceleration 28, there being a high frequency/radio frequency coupling to the connection lead.

In the above described one or more embodiments, the antenna 42 comprises an omni-directional antenna so as to provide coverage of an entire field-of-play. Optionally, other antennas may be used e.g. with a narrower range of receiving angles. For example, multiple antennas with directionalities that individually do not allow for reception of signals from the entire field-of-play, but in combination receive signals from the entire field-of play may be used. For example, four antennas located at each corner of the field-of-play may be used to cover the entire field. This arrangement may also provide redundancy in the system so that, if a signal fails to be received by a closest antenna, it could, potentially, be received by another one of the four antennas.

In a first embodiment accelerometer 52 comprises a H3LIS accelerometer which may be operated at low power as well as a normal power mode and provides 3 axis linear acceleration detection. The H3LIS accelerometer also has sleep and wake up functionality which the described embodiment utilises with synergistic effect with other components of acceleration monitoring system 28. The H3LIS accelerometer is dynamically user configurable for measuring acceleration over scales+/−100 g, +/−200 g and +/−400 g and to provide acceleration values with output (sample) data rates from 0.5 Hz to 1 kHz. The H3LIS accelerometer does not comprise a crystal oscillator clock and therefore the output data rates may not be precise and may drift or vary during its operation.

In the first embodiment the gyroscope unit 54 comprises an LSM gyroscope and utilizes only the gyroscopic function to measure angular velocity. The LSM is a commercially available device incorporating a gyroscope but not does not have the range of measurement of acceleration provided by the H3LIS accelerometer, hence it is used in the first embodiment primarily for its gyroscopic properties. Processor 56 is implemented by way of a "System on Chip" device CC430F5137 produced by Texas Instruments Incorporated of 12500 IT Boulevard, Dallas, Texas, 75243 USA configurable to provide control circuitry for the acceleration monitoring system 28.

Turning to FIG. 4, interrupt lines 59 and 61 are coupled from between the accelerometer 52 to the processor 56 and in the first embodiment are interrupt INT 1 output from pin 11 of the H3LIS accelerometer to in 1 of processor 56 and INT 2 output from pin 9 of the H3LIS accelerometer to pin 2 of processor 56.

Figure 7:
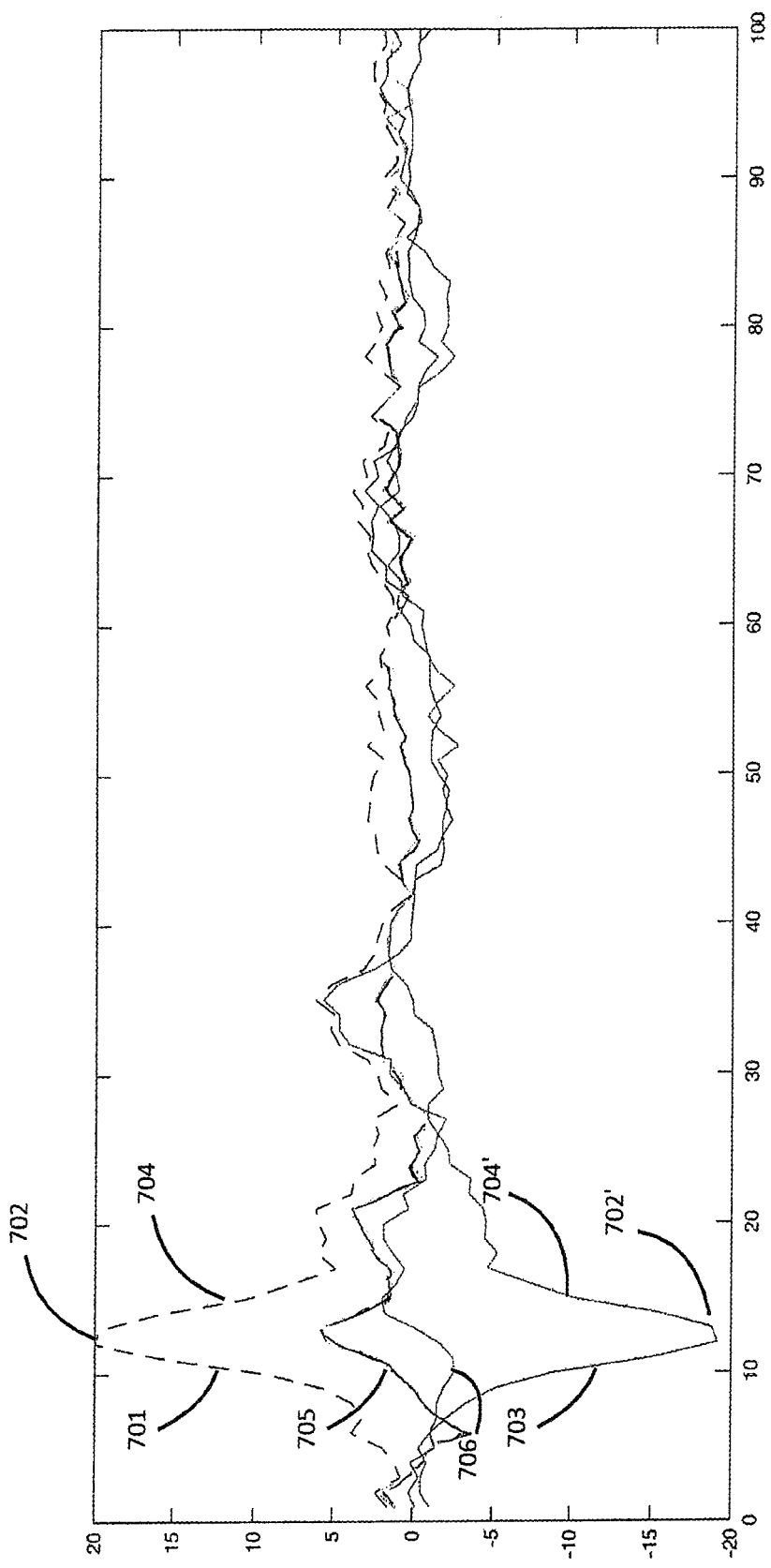
FIG. 7 is a graph of the magnitude of the vector sum of respective axial vectors and of individual axial vectors for linear acceleration against time for a head impact event.
Figure 8:
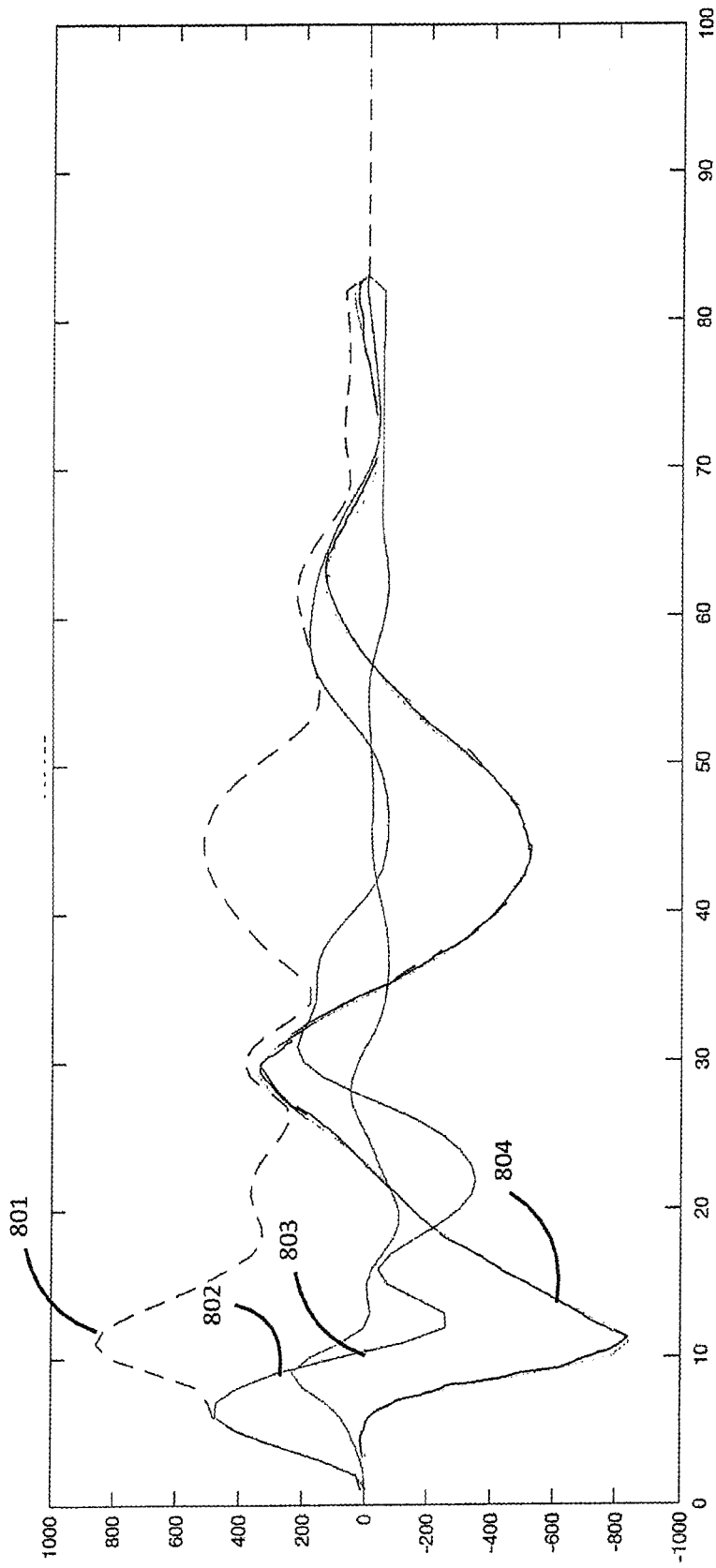
FIG. 8 is a graph of the magnitude of the vector sum of respective axial vectors and of individual axial vectors for angular acceleration against time for the head impact event illustrated in the FIG. 7.

FIG. 7 illustrates a graph of the variation in linear acceleration for an impact event such as may be experienced in a contact sport such as rugby union, and FIG. 8 illustrates a graph of the variation in angular acceleration for the same impact event. The graph in FIG. 7 has an x-axis scaled in milliseconds and a y-axis having acceleration scaled in "g" (metres per second per second), while FIG. 8 has an x-axis scaled in milliseconds and a y-axis scaled in degrees per second per second (i.e. angular acceleration). In the described embodiment the angular acceleration is derived from the angular velocity values in the processor 34 of the monitoring station 32. Lines 701 and 801 are plots of the magnitude of the vector sum of the linear acceleration and angular acceleration along respective axes measured by the accelerometer 52 and gyroscopic unit 54. Plots for respective axes are 703, 705 and 706 for linear acceleration and 802, 803 and 804 for angular acceleration. As can be seen from the graphs illustrated in FIG. 7 and FIG. 8 the magnitude of the vector sum for linear acceleration, 701, comprises an initial fast changing (large gradient) peak, 702 having a 3 dB width 704 of about 5 ms making linear acceleration suitable as a trigger signal. Additionally or optionally, gyroscopic unit 54 in the first embodiment, i.e. implemented as LSM gyroscope, measures and outputs angular velocity the corresponding angular acceleration being calculated by processor 56. Thus, the gyroscopic unit 54 of the first embodiment is not able to provide a trigger signal based on the angular acceleration meeting a threshold criterion or criteria as it does not measure angular acceleration but angular velocity. An inspection of the plots also indicates the output rate suitable for obtaining a meaningful set of acceleration data points. If the trigger threshold was set at 5 g for example the vector sum would cause a trigger signal later than if the threshold was 3 g and so collect less data on the impact event. The angular velocity graph of FIG. 8 comprises a more even variation without the fast rising peak characteristic of linear acceleration. The variation in both linear acceleration and angular velocity tends to subside over a period of 80 ms such that a measurement period of about 80 ms may be sufficient to collect enough data to analyze the impact event.

In the described embodiments, including the first embodiment, power source 26 comprises a battery pack which will typically be capable of powering the acceleration monitoring system 28 for around three hours or so. In order to reduce the size of the battery pack, which will have consequence of reducing the power capacity, acceleration monitoring unit 44 is configured to conserve power to the extent possible while maintaining adequate monitoring of acceleration. Typically a battery pack having a capacity of 40 mAhours will provide about three hours operational time for the acceleration monitoring system configured in accordance with one or more of the described embodiments.

As can be seen from the graphs illustrated in FIGS. 7 and 8, providing illustrative examples, monitoring a head impact event lasting 100 ms would encompass the majority of the variations in both linear and angular acceleration caused by the head impact event. The applicant has discovered that an output rate of 800 Hz is a lower threshold that can be implemented while still having sufficient number of output values to conduct an analysis of the head impact event. That said, output rates lower than 800 Hz, for example 700 Hz or even 600 Hz may still provide sufficient data for an analysis of the head impact event although it may not be as good as would be the case with a greater number of output values.

An upper threshold has been identified by the inventors as around 3 kHz output rate, typically lying in a range between 2.7 kHz and 3.3 kHz. The upper threshold represents a limit at which the consumption of power from a battery pack having a size suitable for inclusion in a mouthguard or the like or some other body embedded device is too great to provide a useful operational life of the acceleration monitoring system 28. For example, at such output rates the acceleration monitoring system 28 may not last the period of a typical rugby union match. In the first embodiment, a output rate of 1 kHz is adopted which provide sufficient output values for analysis of the head impact event while at the same time consuming power at a rate that would provide activation of the acceleration monitoring system 28 for the period of a typical rugby union match including stoppages of play, half-time breaks as well as preparation before the match. Additionally or otherwise, memory space will be used up around three times as quickly for a rate of 3 kHz compared to a rate of 1 kHz. For the same channel bandwidth, a rate of 3 kHz would also occupy the channel for three times longer than for a 1 kHz rate thereby limiting data throughput and hence possibly losing impact data because an acceleration monitoring system may be unable to transmit data on a previous impact before receiving a next impact.

In order to minimize the capacity of the power source 26, i.e. keeping it to a size providing 40 mAhours suitable for powering the acceleration monitoring system 28 for the necessary time period, one or more embodiments in accordance with the present disclosure operate the acceleration monitoring unit 44 at two different output rates. The accelerometer 52 is configured to operate in a low power mode having a low output rate until an output exceeds a threshold acceleration, for example 3 g or 5 g. Subsequent to the threshold being exceeded the accelerometer 52 enters a mode of operation having a higher output rate for a period of about 100 ms. After the high output rate period has expired operation of accelerometer 52 returns to the low power mode. In this way, power may be conserved since power is only consumed at a higher rate during a head impact event i.e. when it is needed.

In the first embodiment, features and functions of the H3LIS accelerometer may be utilized in an unconventional configuration within the I2C bus architecture to achieve operation of this acceleration monitoring unit 44.

The H3LIS accelerometer is configurable in a "sleep-to-wake" mode utilizing control register 5 (CTR L_REG5). The two lowest order bits of CTRL_REG5 comprise the turn-on bits "TurnOn1" and "TurnOn0" and when both turn-on bits are set "high" the sleep-to-wake status is active. In the sleep-to-wake active mode, the H3LIS accelerometer is responsive to an interrupt event to activate its normal mode.

For the first embodiment, the H3LIS accelerometer of acceleration monitoring unit 44 is initialized responsive to being powered on in the "sleep-to-wake" mode, i.e. turn-on bits "TurnOn1" and "TurnOn0" are set "high" in CTRL_REG5. Additionally, the threshold acceleration for waking accelerometer H3LIS from its sleep mode is set. During the initialization setup routine the normal mode output data rate is configured and for the first embodiment is configured to be 1000 Hz by setting bits "DR1" and "DR0" of control register 1 (CTRL_REG1) high. Also, the power mode selection bits, "PM2", "PM1" and PM0" of CTRL_REG1 are set high in a combination to select the output data rate during the low power mode, i.e. the acceleration output rate during the sleep state of the "sleep-to-wake" mode. The low power output data) rates are selectable from the following frequencies, 0.5 Hz, 1 Hz, 2 Hz, 5 Hz and 10 Hz. In the first embodiment the output frequency for sleep mode is set to be 10 Hz, i.e. the highest output frequency available for the sleep mode of the H3LIS accelerometer, in order to maximize the likelihood of sensing an impact event sufficiently early in the acceleration profile for the impact event to be able to capture a sufficient number of samples for meaningful analysis of the impact event. Other initialization configurations are implemented for the H3LIS accelerometer as well as the other modules of acceleration monitoring unit 44 together with other modules of acceleration monitoring system 28. The instructions, settings and parameters for initialization are stored in a non-volatile part of memory 46. Additionally, processor implementable instructions and parameters are stored in memory 46 and which may be accessed by processor 56 for execution in controlling and operating the acceleration monitoring unit 44 and other modules of the acceleration monitoring system 28, for example transceiver 48. Processor 56 and instructions stored in memory 46, and the implementation by processor 56 of those instructions, may be considered control circuitry (or at least a part thereof) of the acceleration monitoring system 28.

Operation of acceleration monitoring system 28 when in use will now be described with reference to the process flow control diagrams illustrated in FIGS. 9 and 10. Process flow control will be illustrated in diagrams for respective modules, processor 56, accelerometer 52 and gyroscope 54 because each unit has a level of autonomy but may also exchange data and instructions between one or more of each other.

Figure 9:
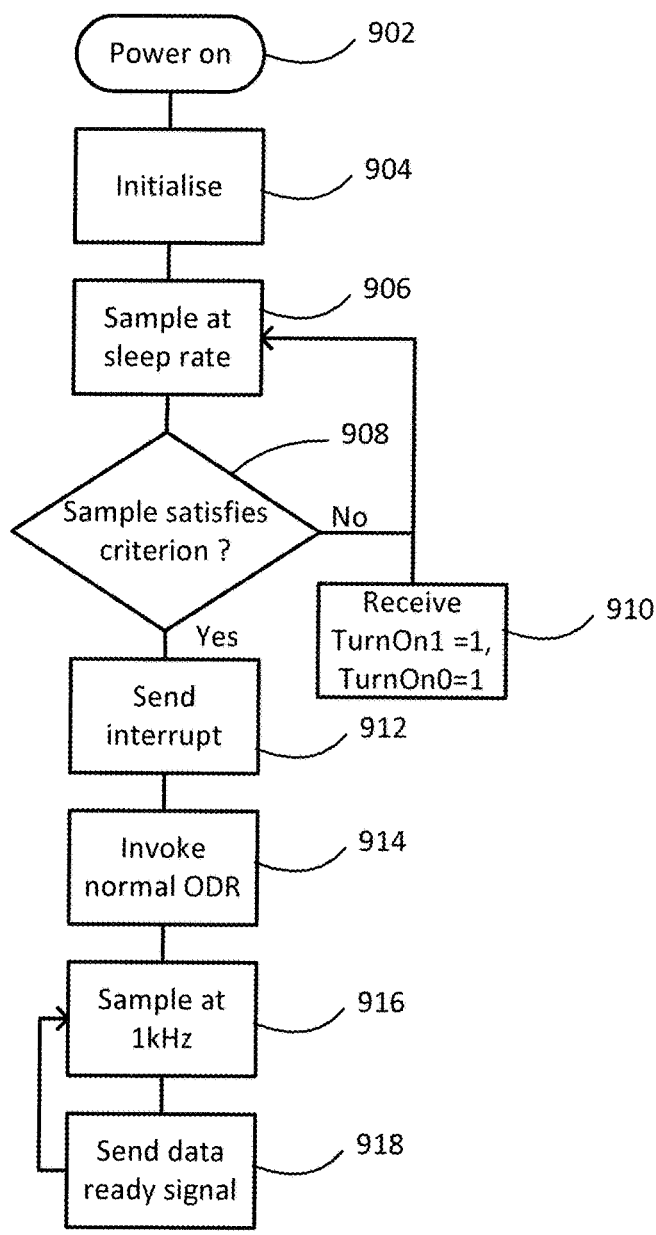
FIG. 9 is a process control flow diagram for an H3LIS accelerometer in accordance with an embodiment of the present disclosure.
Figure 10:
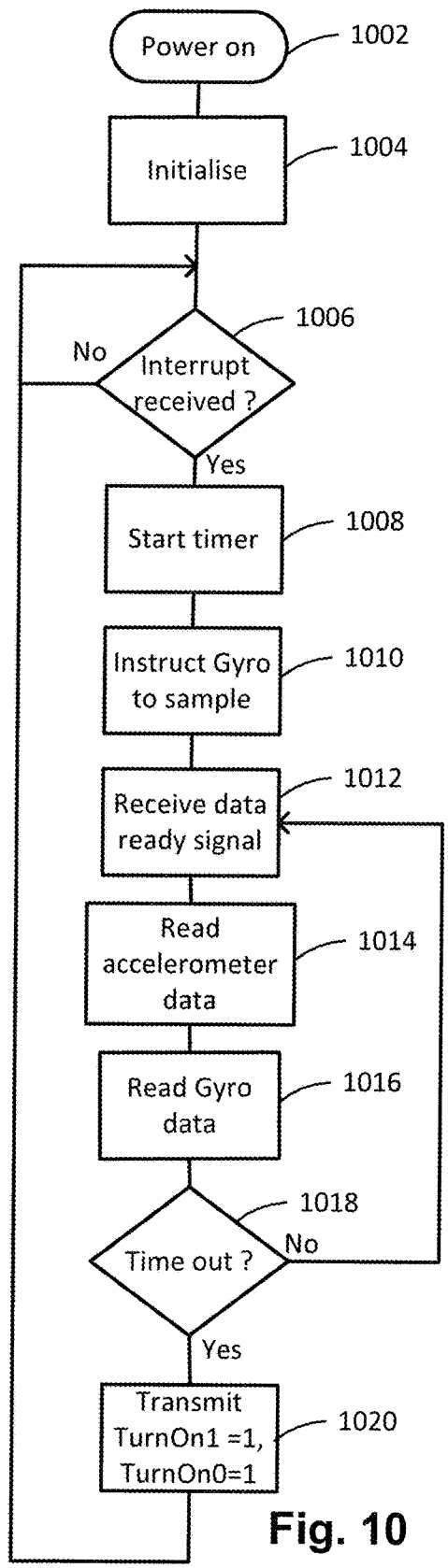
FIG. 10 is a process control flow diagram for an H3LIS control circuitry configured as a processor in accordance with an embodiment of the present disclosure.

The process control flow diagram 900 for the accelerometer H3LIS is illustrated in FIG. 9 and after power on, 902, the accelerometer 52 is initialized, 904, with the appropriate settings and parameters in the relevant registers. At step 904 the gyrometer unit 54 may also be initialized. The accelerometer is initialized such that it operates in its "sleep-to-wakeup" mode and starts to provide acceleration values at the output rate set up for the sleep mode, 906. The output rate, also known as the output data rate (ODR) is initialized to be 10 Hz. The value (square of the respective vector magnitude values) is tested against the acceleration threshold criterion at step 908. The squared value is used for the check as that is the significant parameter related to the measurement of possible damage caused by the impact, the particular direction not being so relevant and because currently established measures for severity of acceleration are based only on magnitude of acceleration. That is to say, the square of the magnitude of acceleration in each of the three axes is calculated so that it may be determined if the acceleration exceeds the threshold in any one of the axes. However, the vector may be recorded for further analysis. In particular, all motion data, i.e. vectors, may be transmitted to the monitoring station 32. If the value criterion or criteria are not satisfied then process control flows back to step 906.

If the acceleration value criterion or criteria is or are satisfied, typically if acceleration exceeds the threshold in any one of the axes, then process control flows to step 912 at which the H3LIS accelerometer 52 sends an interrupt signal to the processor 56. Processor 56 has previously been powered on, 1002, initialized 1004 and while attending to various other processor functions and activities within the acceleration monitoring system 28 also waits for an interrupt. If no interrupt is received process control continues to wait for an interrupt, step 1006.

If an interrupt is received process control flows to step 1008 at which the processor 56 starts a timer, which in the first embodiment is set for 100 ms. processor 56 also instructs, step 1010, the gyroscope to begin sampling angular velocities, the gyroscope having previously been in a quiescent or low-power state.

Turning back now to the process flow control diagram 900 of FIG. 9, following the sending of the interrupt at step 912, H3LIS accelerometer 52 invokes its normal mode output data rate as configured in the initialization step 904, at step 914. For the first embodiment, the output data rate is 1 kHz and acceleration values are output at 1 kHz, step 916. Once a value for all three axes has been established a data ready signal is transmitted across the I²C bus 58 to processor 56, step 918.

Processor 56 receives the data ready signal, step 1012 and in response thereto executes a read across the I²C bus 58 to read the accelerometer data 1014. After reading the accelerometer data processor 56 reads angular velocity data, step 1016, from gyroscope unit 54. Gyroscopic unit 54 is configured to provide data output at a rate of just below 1 kHz, typically in the range 900 Hz to 990 Hz. Reading values from the H3LIS accelerometer 52 at a frequency of 1 kHz is convenient since it provides a time window in which to perform a read of the accelerometer data as well as the read of the gyroscope unit data before the next sample is ready from the H3LIS accelerometer 52 as the process control flow loops around steps 916 and 918.

Following reading of the angular velocity from the gyroscopic unit 54, process control flows to step 1018 where it is determined whether or not the acceleration and angular velocity read window has expired, i.e. for the first embodiment whether or not the timer has reached 100 ms, step 1018. If the process has not timed out then process control flows back to step 1012 to receive a data ready signal from the H3LIS accelerometer 52. If the process has timed out at step 1018 process control flows to step 1020 at which the processor 52 transmits data to set turn on bits TurnOn1 and TurnOn0 of H3LIS control register CTRL_REG5 high (i.e. set to "1") to invoke the "sleep-to-wakeup" mode and put the H3LIS accelerometer 52 into a low power mode, step 910. H3LIS accelerometer 52 is now in "sleep-to-wakeup" mode and at step 906 of its procedure flow as illustrated in the process control flow diagram 900 of FIG. 9.

Depending upon the output rate during the "sleep" mode there is the possibility that the start of an impact event, or even the whole of an impact event, could be missed. While this may be acceptable in certain scenarios or applications it may be desirable to configure the system in such a way that it is unlikely an impact event would be missed and to substantially increase the likelihood that the start of an impact event is identified so that appropriate sampling can take place.

In particular, in accordance with a second embodiment, the system is configured in a manner to increase the likelihood that the start of an impact event is identified. The second embodiment utilizes a system architecture and circuitry as illustrated in and described with reference to FIGS. 3 and 4, operative in a network such as illustrated in and described with reference to FIGS. 5 and 6.

The operation of the acceleration monitoring system, specifically the H3LIS accelerometer 52 and processor 56 in accordance with the second embodiment will now be described with reference to the process flow control diagrams 1100 and 1200 respectively illustrated in FIGS. 11 and 12. In the second embodiment described herein, the trigger acceleration and calculation and storage of acceleration and angular velocity values are the same as for those described with respect to the first embodiment. Turning now to the process flow control diagram 1100 the H3LIS accelerometer 52 is powered on and initialized at step 1104. Initialization of the H3LIS accelerometer 52 includes amongst other things receiving register settings from processor 56 over the I²C bus 58 for setting the internal clock, an output rate of 1 kHz and the threshold acceleration initiating setting of interrupt 1, established on reference 59 in FIG. 4. Additionally, the conditions for setting interrupt 1 and the signal shape for interrupt signal.

In particular, the initialization at step 1104 involves the following setup procedures with reference to respective registers and pins of the H3LIS accelerometer 52 and LMS Gyroscopic unit 54. The setup procedures are driven by processor 56

1. Configure Pins—Set the pins for input and output as appropriate with the test points set as outputs.
2. Check battery—This steps it to check if battery is too low so can remain turned off to charge more efficiently.
3. Initialize H3LIS variables—Set internal initial values responsive to receiving values from processor 56.
4. Power up Gyro—power up signal written by processor 56 to the LSM gyroscopic unit 54 across the I2C bus to start up the gyroscopic unit 54.
5. Configure Gyro—the gyroscopic unit 54 is setup by writing to control registers:
   a. GYRO_CTRL_REG3, write 0x80 to enable Low power mode;
   b. GYRO_CTRL_REG5_XL, write 0x0—to disable axes output of accelerometer of LSM gyroscopic unit 54.
6. Configure H3LIS Accelerometer—processor 56 writes to the control registers of the H3LIS Sensor to set the following values:
   a. H3LIS_CTRL1, set to 0x3F

| PM2 | PM1 | PM0 | DR1 | DR0 | Zen | Yen | Xen |
|-----|-----|-----|-----|-----|-----|-----|-----|
| 0   | 0   | 1   | 1   | 1   | 1   | 1   | 1   | which enables normal power mode and fast data rate of 1 kHz, for all axes;
   b. H3LIS_CTRL3, set to 0x04—Configure Interrupt data structure to latch an interrupt request on the INT_1 SRC register, with the INT_1 SRC register being cleared by reading of the INT_1 SRC register.

| IHL | PP_OD | LIR2 | I2_CFC1 | I2CFC0 | LIR1 | I1_CFC1 | I1_CFC0 |
|-----|-------|------|---------|--------|------|---------|---------|
| 0   | 0     | 0    | 0       | 0      | 1    | 0       | 0       | c. H3LIS_ADDR, H3LIS_CTRL4, set to 0x90—which provides for block data updating there being no continuous update of registers. It also sets the full scale deflection for the accelerometer to be ∓200 g.

| BDU | PP_BLE | FS1 | I2_FS0 | 0 | 0 | 0 | SIM |
|-----|--------|-----|--------|---|---|---|-----|
| 0   | 0      | 0   | 0      | 1 | 0 | 0 | 1   | d. H3LIS_CTRL5, set to 0x03—Enables the 'sleep to wake' function so that responsive to an interrupt the normal mode is invoked and the Output Data Rate (ODR) is increased to the value defined in CTRL-_REG1, i.e. the fast data rate of 1 kHz.

| 0 | 0 | 0 | 0 | 0 | 0 | TurnOn1 | TurnOn0 |
|---|---|---|---|---|---|---------|---------|
| 0 | 0 | 0 | 0 | 0 | 0 | 1       | 1       | e. H3LIS_INT1_CFG, set to 0x2a—enables an interrupt request on INT1 if acceleration on any one or more of respective mutually orthogonal axes X, Y, Z exceeds a preset acceleration threshold.

| AOI | 0 | ZHIE | ZLIE | YHIE | YLIE | XHIE | XLIE |
|-----|---|------|------|------|------|------|------|
| 0   | 0 | 1    | 0    | 1    | 0    | 1    | 0    | f. H3LIS_INT1_THRESHOLD—this register is set to the threshold of the acceleration to trigger the read for respective axes of impact.
g. H3LIS_INT1_DUR, 0x01—This is set to establish the duration of an impact in order to trigger interrupt and sampling at the preset ODR. So, this is a first step of the accelerometer in that one reading at 1 kHz (0.001 seconds) above threshold triggers the sampling mode at the ODR.
7. Attach MCU Interrupt—LIS_INT1_PIN—RISING—setting this bit prepares processor 56 for interrupt from accelerometer 52 in which the interrupt is established by a "rising edge".
8. Flush H3LIS values—this clears out any initial values in accelerometer 52.

Following initialization, H3LIS accelerometer 52 outputs acceleration in each of the three axes at a rate of 1 kHz, step 1106 and at step 1108 the vector sum of the linear acceleration measured in each of the three axes is calculated and tested against the threshold criterion set during the initialization step 1104. In the described embodiment the threshold criterion is merely that the linear acceleration exceeds a threshold value in at least one axis. If the vector sum does not exceed a threshold value then process control flows back to step 1106 at which outputting acceleration values at 1 kHz continues and the vector sum is then tested against the threshold at step 1108.

If the magnitude for at least one of respective axis acceleration values exceeds the threshold at step 1108 process control flows to step 1110 where interrupt 1 is sent to processor 56. H3LIS accelerator 52 continues to output acceleration values at 1 kHz, step 1112 and also sends interrupt 1 to processor 56 at a frequency of 1 kHz, step 1114, where it is treated as a data ready signal as described below. Process control then flows to step 1116 where it is determined whether or not a count expiry signal has been received from the processor 56. If a count expiry signal has not been received then process control flows back to step 1112. If a count expiry signal has been received process control flows back to step 1106.

Turning now to the process control flow diagram 1200 illustrated in FIG. 12 processor 56 is powered on and initialized at step 1204. As part of the initializing process accelerometer 52 is powered on and initialized at least in part by processor 56 sending signals to H3LIS accelerometer 52 over the I²C bus to configure H3LIS accelerometer 52 to output at 1 kHz, to set the acceleration threshold for initiating interrupt 1 and for providing interrupt 1 as a 1 kHz signal, amongst other things as described above in relation to the initialization of the H3LIS. Gyroscopic unit 54 is powered on also. At step 1206 processor 56 determines whether or not an interrupt has been established on interrupt line 1. If interrupt 1 has not been received process control flows back to the start of step 1206 to continue waiting for an interrupt 1 signal.

If an interrupt 1 signal has been received at step 1206 process control flows to step 1208 where the counter is initiated to 1 and the maximum acceleration and maximum gyrometer values are set to zero.

Additionally, the interrupt signal from the accelerometer to the processor 52 is detached from the processor 56 (LIS_INT1_PIN—RISING) and switched to a data ready signal so as to use interrupt 1 as a data ready signal (H3LIS_CTRL3)—0x06.

| IHL | PP_OD | LIR2 | I2_CFC1 | I2CFC0 | LIR1 | I1_CFC1 | I1_CFC0 |
|-----|-------|------|---------|--------|------|---------|---------|
| 0   | 0     | 0    | 0       | 0      | 1    | 1       | 0       |

Interrupt 1 may be considered as a "data ready" signal for the processor 56 and be output at step 1110 of process flow control diagram 1100 to trigger an interrupt at processor 56 to cause processor 56 to initiate an impact event data read data procedure, such as initializing the data count, step 1208. Interrupt 1 is signaled at a frequency of 1 kHz so that processor 56 may read the accelerometer and gyroscopic unit output before the next output is established at the accelerometer 52 and gyroscopic unit 54. Optionally, interrupt 1 signal may also be "polled", i.e. interrupt 1 input to processor 56 is interrogated to determine its status. If the interrupt 1 signal is "high" (i.e. "set") processor 56 may be configured to read samples from respective accelerometer 52 and gyroscopic unit 54. A read of interrupt 1 signal causes interrupt 1 to go "low". Such an optional implementation may avoid a rising edge of interrupt signal 1 being missed by processor 56 due to the processor 56 still being in the interrupt service routine of the previous interrupt.

Process control then flows to step 1210 at which the processor 52 is configured to wait 1210 for a data ready signal. If a data ready signal is received, i.e. interrupt 1 from H3LIS accelerometer 52 received as a data ready signal, process control flows to step 1212 and processor 56 begins reading the sampled angular velocities.

As described with reference to FIG. 11, following the sending of interrupt 1 to processor 56 the H3LIS accelerometer 52 continues to output interrupt 1 to processor 56 at the 1 kHz cycle rate. Thus, interrupt 1 signal is present at the processor 56 and is received at processor 56, step 1212. Interrupt 1 signal may now be considered to be utilized by the processor 56 as a clock signal against which processor 56 will perform its various functions. Responsive to each rising edge of the interrupt 1 signal, or optionally each time the interrupt 1 signal is determined to be "high" and samples read, the counter is incremented by the value 1, step 1214. Responsive to receiving the interrupt 1 signal rising edge cycle processor 56 reads the gyrometer unit 54 sensor data, step 1216. Once the data from the gyrometer unit 54 has been read, processor 56 then reads the respective linear acceleration data for each of the three axes from the H3LIS accelerometer 52, step 1218. The cycle rate, i.e. frequency, established for the interrupt 1 signal is such so as to provide sufficient time for the H3LIS accelerometer 52 to have its velocity data read by processor 56 within one cycle of the interrupt 1 signal in addition to the data read from the gyrometer unit 54.

To process data for an impact the processor 56 checks to determine if sufficient device storage is available in memory 46 to hold the samples to be taken for an impact event, step 1220, and if not the data sampling process merely calculates and stores the squared magnitudes of the maxima acceleration values through the impact event, step 1224 for transmission after the impact and typically with a status packet transmission. If there is sufficient memory, the gyroscopic and acceleration sensor data samples are stored in memory 46 and transmitted to the transceiver 41 of the monitoring station 32 after the impact has ended as well as the squared magnitudes of the maxima acceleration values. Optionally, processor 56 then calculates the squares of the respective vector magnitudes and stores them for transmission to the monitoring station 32 for each output cycle following an impact, step 1222. The square root of the squares of the respective maxima acceleration vector magnitudes are calculated in the central unit 32, which saves on processing resources and power and leaves the calculation to when it needs to be done, i.e. at the monitoring station. The magnitude could be calculated in the acceleration monitoring system 44 if processing resources and/or power were not an issue. Process flow control flows to step 1226 from both step 1224 and step 1226.

Processor 56 control the flow to step 1226 to determine if the count value has reached it maximum value. If not process control flows back to step 1212 where the reading of the H3LIS accelerometer 52 and gyroscopic unit 54 takes place again. If the maximum count value has been reached and the count expired, process control flows to step 1228 where a signal indicative of the count having expired is transmitted to the H3LIS accelerometer 52 which ceases sending interrupt 1 and returns to step 1106 at which sampling continues and the vector sum acceleration is tested at step 1108 to determine if it exceeds the threshold for activating interrupt 1 to signal processor 56 to read the acceleration data from the H3LIS accelerometer 52 and gyroscopic unit 54. Additionally, in general outline, if the impact is complete (for the described embodiment when the count reaches 104), the following impact completion activities are performed:

a. Add max values to last impact array; and
 b. Reattach Interrupt (H3LIS_INT1_PIN—RISING).

Impacts are transmitted on the main loop at step 1228 in which processor 56 initiates transmitting the acceleration data to the acceleration monitoring system 28.

The maximum values of the acceleration data and the gyroscopic data for the last five impact events are stored in an array having five data bins so that the oldest pair of values are overwritten by the most recent pair of values. Then, the Interrupt H3LIS_INT1_PIN is reattached to processor 56 ready to initiate a new impact data collection routine if the vector sum acceleration threshold is exceeded and process flow finishes and returns to step 1206 where it waits until the next interrupt 1 signal.

The maximum count value 104 is set at a value sufficient to capture acceleration due to a head impact event. As can be seen from FIGS. 7 and 8 significant acceleration variation due to a head impact events continues for up to around 80 ms thereafter it gradually decays to a relatively low level. Thus, for the clock to be incremented at each cycle of interrupt 1 signal, e.g. by a falling edge of the signal, having a frequency of 1 kHz the maximum count value will typically be set at 80 around that value. If interrupt 1 signal were to be at a different frequency, for example 3 kHz then the maximum count value will typically be around 240, whereas if the frequency of interrupt 1 signal was 800 Hz maximum count value will typically be around 64. If a shorter or longer period for collecting acceleration data is desired then the maximum count value may be reduced or increased accordingly.

In accordance with a third embodiment, the system is configured in a manner to reduce power consumption further. The third embodiment utilizes a system architecture and circuitry as illustrated in and described with reference to FIGS. 3 and 4, operative in a network such as illustrated in and described with reference to FIGS. 5 and 6.

The operation of the acceleration monitoring system, specifically the H3LIS accelerometer 52, gyroscopic module (in the described embodiments a LSM9DS1 device) 54 and processor 56, in accordance with the third embodiment will now be described with reference to the process flow control diagrams 1100, 1300 and 1400 respectively illustrated in FIGS. 11, 13 and 14. In the third embodiment described herein, the trigger acceleration and calculation and storage of acceleration and angular velocity values are the same as for those described with respect to the first embodiment. Turning now to the process flow control diagram 1100 of FIG. 11, operation of the H3LIS accelerometer 52 is the same for the third embodiment as for the second embodiment. The following steps, undertaken by processor 56, initialize and set up gyroscopic unit 54.

4. Power up Gyro—power up signal written by processor 56 to the LSM gyroscopic unit 54 across the I2C bus to start up the gyroscopic unit 54.
 5. Configure Gyro—the gyroscopic unit 54 is setup by writing to control registers:
   a. GYRO_CTRL_REG3, write 0x80 to enable Low power mode which sets the LP_mode bit in the registyer to "1";
   b. GYRO_CTRL_REG5_XL, write 0x0—to disable axes output of accelerometer of LSM gyroscopic unit 54.

Turning now to the process control flow diagram 1300 illustrated in FIG. 13, operation of processor 56 in accordance with the third embodiment will now be described. Steps having similar function to those illustrated in FIG. 12 have the same number as those steps in FIG. 12 with an additional "'". Processor 56 is powered on and initialized at step 1204'. As part of the initializing process accelerometer 52 is powered on and initialized at least in part by processor 56 sending signals to H3LIS accelerometer 52 over the I²C bus to configure H3LIS accelerometer 52 to output at 1 kHz, to set the acceleration threshold for initiating interrupt 1 and for providing interrupt 1 as a 1 kHz signal, amongst other things as described above in relation to the initialization of the H3LIS. Gyroscopic unit 54 is powered on also in particular with reference to items 4 and 5 of the initialization routine described above. At step 1206' processor 56 determines whether or not an interrupt has been established on interrupt line 1. If interrupt 1 has not been received process control flows back to the start of step 1206' to continue waiting for an interrupt 1 signal.

If an interrupt 1 signal has been received at step 1206' process control flows to step 1207 (a new step compared to the second embodiment) in which processor 56 sends a "wake-up" signal over the I2C bus to gyroscopic module 54. The "wake-up" signal is a write to output data rate (ODR) configuration register CTRL_REG1_G (10 h) to set the data rate to a normal output data rate. The ODR bits (ODR_G [2:0] may be set to 100, 101 and 110 to place the gyroscope module 54 in normal mode of operation with output data rates of 238 Hz, 476 Hz and 952 Hz respectively. In the described, third, embodiment an output data rate of 952 Hz is utilized.

Figures 13, 14:
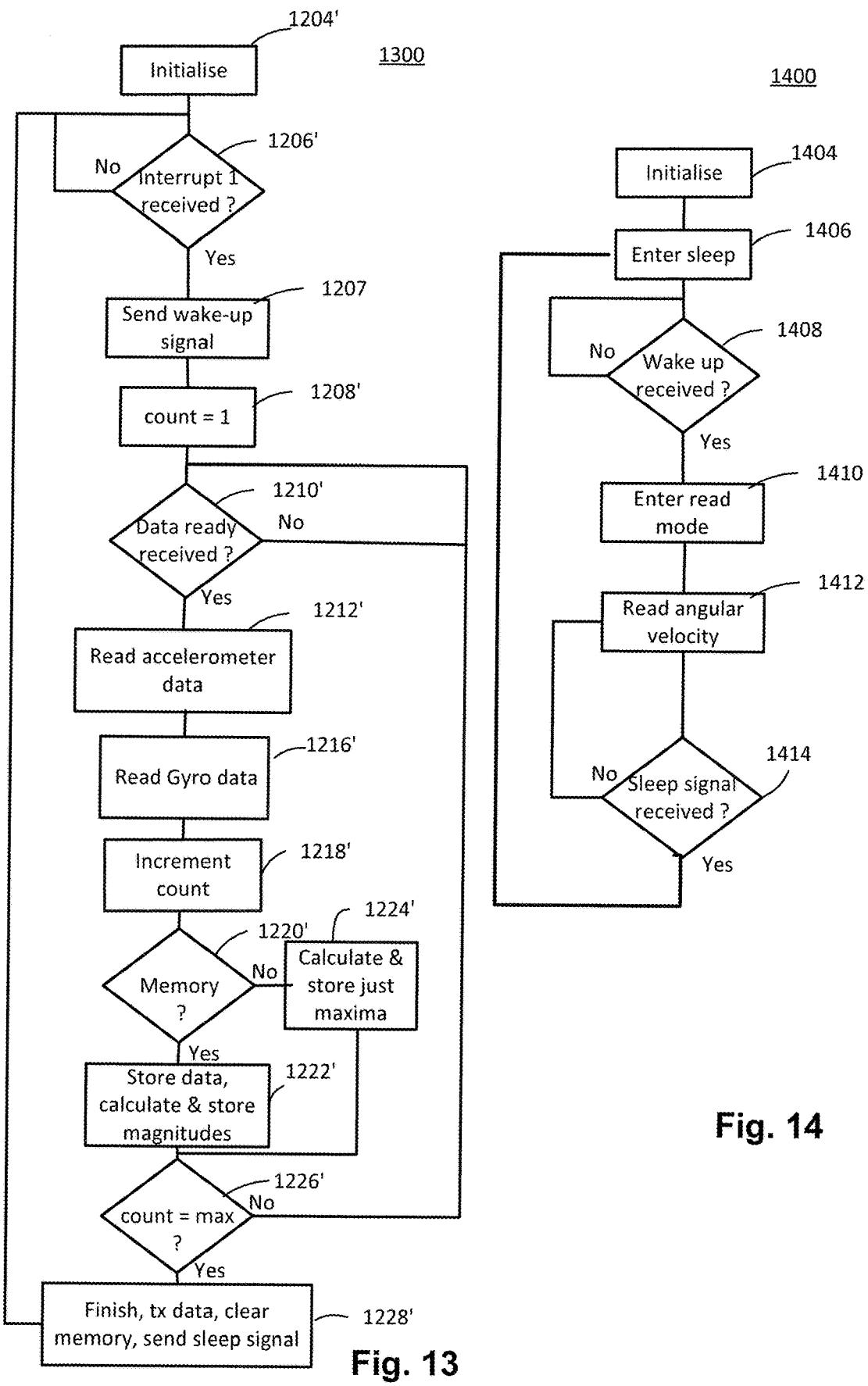
FIG. 13 is a process control flow diagram for a processor in accordance with a third embodiment of the present disclosure.
FIG. 14 is a process control flow diagram for a LSM9DS1 device in accordance with a third embodiment of the present disclosure.

Turning now to FIG. 14, a process flow control diagram 1400 for the LMS gyroscopic module 54 is illustrated in which an initialization step 1404 including power up and low power mode being enabled takes place. The low power (sleep) mode may be set at step 1406 by writing to the appropriate ODR_G[2:0] bits 001, 010 and 011, establishing increasingly greater data rates, depending upon the output data rate desired in the low power mode. In the described, third, embodiment the lowest data rate is utilized since it consumes the least current and therefore utilizes the least power. Process flow control then proceeds to step 1408 where the LMS gyroscopic module 54 determines whether or not a wake-up signal has been received from processor 56. If no wake-up signal has been received process flow control returns to monitoring for wake-up signal. If a wake-up signal has been received, i.e. 110 written to the ODR bits (ODR_G[2:0] of CTRL_REG1_G (10 h, then process flow control proceeds to step 1410 where the LMS gyroscopic module 54 enters a read mode. Process flow control then proceeds to step 1412 at which angular velocity is read and provided at the set output data rate. At step 1414 LMS gyroscopic module 54 determines whether not a sleep signal has been received. If not, process flow control returns to step 1412 where the angular velocities are continued to be read. If a sleep signal has been received, i.e. writing 001 to the ODR_G[2:0] bits of CTRL_REG1_G (10 h), process flow control returns to step 1406 where the LMS gyroscopic module 54 enters the low power (sleep) mode.

Returning to FIG. 13, process flow control proceeds to step 1208' where the counter is initiated to 1 and the maximum acceleration and maximum gyrometer values are set to zero.

Additionally, the interrupt signal from the accelerometer to the processor 52 is detached from the processor 56 (LIS_INT1_PIN—RISING) and switched to a data ready signal so as to use interrupt 1 as a data ready signal (H3LIS_CTRL3)—0x06.

may avoid a rising edge of interrupt signal 1 being missed by processor 56 due to the processor 56 still being in the interrupt service routine of the previous interrupt.

Process control then flows to step 1210' at which the processor 52 is configured to wait 1210' for a data ready signal. If a data ready signal is received, i.e. interrupt 1 from H3LIS accelerometer 52 received as a data ready signal, process control flows to step 1212' and processor 56 begins reading the sampled linear accelerations.

As described with reference to FIG. 11, following the sending of interrupt 1 to processor 56 the H3LIS accelerometer 52 continues to output interrupt 1 to processor 56 at the 1 kHz cycle rate. Thus, interrupt 1 signal is present at the processor 56 and is received at processor 56, step 1212'. Interrupt 1 signal may now be considered to be utilized by the processor 56 as a clock signal against which processor 56 will perform its various functions. Responsive to receiving the interrupt 1 signal rising edge cycle processor 56 reads the respective linear acceleration data for each of the three axes from the H3LIS accelerometer 52, step 1212'. Once the data from the H3LIS accelerometer 52 has been read, processor 56 then reads the gyroscopic unit 54 sensor data, step 1216'. Responsive to each rising edge of the interrupt 1 signal, or optionally each time the interrupt 1 signal is determined to be "high" and samples read, the counter is incremented by the value 1, step 1218'. The cycle rate, i.e. frequency, established for the interrupt 1 signal is such so as to provide sufficient time for the H3LIS accelerometer 52 to have its velocity data read by processor 56 within one cycle of the interrupt 1 signal in as well as data read from the gyrometer unit 54.

To process data for an impact the processor 56 checks to determine if sufficient device storage is available in memory 46 to hold the samples to be taken for an impact event, step 1220', and if not the data sampling process merely calculates and stores the squared magnitudes of the maxima acceleration values through the impact event, step 1224 for transmission after the impact and typically with a status packet transmission. If there is sufficient memory, the gyroscopic and acceleration sensor data samples are stored in memory 46 and transmitted to the transceiver 41 of the monitoring station 32 after the impact has ended as well as the squared magnitudes of the maxima acceleration values. Optionally, processor 56 then calculates the squares of the respective vector magnitudes and stores them for transmission to the monitoring station 32 for each output cycle following an

| IHL | PP_OD | LIR2 | I2_CFC1 | I2CFC0 | LIR1 | I1_CFC1 | I1_CFC0 |
|---|---|---|---|---|---|---|---|
| 0 | 0 | 0 | 0 | 0 | 1 | 1 | 0 |

Interrupt 1 may be considered as a "data ready" signal for the processor 56 and be output at step 1110 of process flow control diagram 1100 to trigger an interrupt at processor 56 to cause processor 56 to initiate an impact event data read data procedure, such as initializing the data count, step 1208'. Interrupt 1 is signaled at a frequency of 1 kHz so that processor 56 may read the accelerometer and gyroscopic unit output before the next output is established at the accelerometer 52 and gyroscopic unit 54. Optionally, interrupt 1 signal may also be "polled", i.e. interrupt 1 input to processor 56 is interrogated to determine its status. If the interrupt 1 signal is "high" (i.e. "set") processor 56 may be configured to read samples from respective accelerometer 52 and gyroscopic unit 54. A read of interrupt 1 signal causes interrupt 1 to go "low". Such an optional implementation impact, step 1222. The square root of the squares of the respective maxima acceleration vector magnitudes are calculated in the central unit 32, which saves on processing resources and power and leaves the calculation to when it needs to be done, i.e. at the monitoring station. The magnitude could be calculated in the acceleration monitoring system 44 if processing resources and/or power were not an issue. Process flow control flows to step 1226' from both step 1224' and step 1226'.

Processor 56 controls the flow to step 1226' to determine if the count value has reached its maximum value. If not, process control flows back to step 1212' where the reading of the H3LIS accelerometer 52 and gyroscopic unit 54 takes place again. If the maximum count value has been reached and the count expired, process control flows to step 1228' where a signal indicative of the count having expired is transmitted to the H3LIS accelerometer 52 which ceases sending interrupt 1 and returns to step 1106 at which sampling continues and the vector sum acceleration is tested at step 1108 to determine if it exceeds the threshold for activating interrupt 1 to signal processor 56 to read the acceleration data from the H3LIS accelerometer 52 and gyroscopic unit 54. Additionally, in general outline, if the impact is complete (for the described embodiment when the count reaches 104), the following impact completion activities are performed:

c. Add max values to last impact array; and d. Reattach Interrupt (H3LIS_INT1_PIN—RISING).

Impacts are transmitted on the main loop at step 1228' in which processor 56 initiates transmitting the acceleration data to the acceleration monitoring system 28.

The maximum values of the acceleration data and the gyroscopic data for the last five impact events are stored in an array having five data bins so that the oldest pair of values are overwritten by the most recent pair of values. Then, the Interrupt H3LIS_INT1_PIN is reattached to processor 56 ready to initiate a new impact data collection routine if the vector sum acceleration threshold is exceeded and process flow finishes and returns to step 1206' where it waits until the next interrupt 1 signal.

The maximum count value 104 is set at a value sufficient to capture acceleration due to a head impact event. As can be seen from the example illustrated in FIGS. 7 and 8 significant acceleration variation due to a head impact events may continue for up to around 80 ms thereafter it gradually decays to a relatively low level. Thus, for the clock to be incremented at each cycle of interrupt 1 signal, e.g. by a falling edge of the signal, having a frequency of 1 kHz the maximum count value will typically be set at 80 around that value. If interrupt 1 signal were to be at a different frequency, for example 3 kHz then the maximum count value will typically be around 240, whereas if the frequency of interrupt 1 signal was 800 Hz maximum count value will typically be around 64. If a shorter or longer period for collecting acceleration data is desired then the maximum count value may be reduced or increased accordingly.

In a fourth embodiment, gyroscopic module 54 may be always turned on and not operated in a low-power mode. In such an embodiment, processor 56 may be operated in a low power mode until receipt of the interrupt signal from accelerometer module 52 responsive to acceleration exceeding the threshold value. Operation of processor 56 in accordance with the fourth embodiment is illustrated in the process flow control diagram of FIG. 15. The operation of processor 56 is much the same as described for the third embodiment and where the process flow control steps are the same or substantially equivalent as those in the process flow control chart of FIG. 13 (and also FIG. 12 to the extent they are consistent with the process flow control described with reference to FIG. 15) they are given the same number and their description is not repeated in the interests of brevity. However, the final part of the initialization step, 1504, is to put the processor 56 into its sleep mode. If interrupt 1 is received at step 1206' then process control flows to step 1507 in which the processor wakes up. Process flow control then follows the same operations as described with reference to FIG. 13 (and also FIG. 12 to the extent they are consistent with the process flow control described with reference to FIG. 15) up to step 1528. At step 1528 process flow finishes and returns to step 1206' where it waits until the next interrupt 1 signal.

In an optional embodiment comprising a variation of the acceleration threshold criterion, the criterion is that the acceleration must increase above a minimum rate. For the described optional embodiment, if the threshold acceleration is 3 g then processor 56 may monitor a pre-set number of acceleration data points following linear acceleration having achieved a threshold value. The rate of increase (positive slope or gradient) of the acceleration may be calculated and if achieving exceeding a preset value may initiate operation of the system. For example, a gradient of at least 45° may have to be measured. Optionally, a steeper gradient such as 60° or even more may be established so as to avoid activating the system for impact succeeding threshold value which are insufficient or unlikely to constitute an impact event.

In a modification applicable to all previously described embodiments, once the acceleration monitoring system 28, or one or more component parts thereof previously in sleep mode such as the accelerometer 52, gyroscopic unit 54 and/or processor 56, is/are awake, the "magnitude squared" of the acceleration (to avoid having to calculate the square root) for each sample (in three axes) is determined. The "magnitude squared" for each axis is compared to a "reported impact" threshold. If any one of the "magnitude squared" exceeds the "reported impact" threshold, a flag is set indicating that the impact is sufficiently large to report, i.e. transmit to the monitoring station 32. If none of the "magnitude squared" exceeds the "reported impact" threshold, the flag is not set, i.e. at "0" value. After a pre-set number of samples, for example 35, the flag is checked and if set the system 28 keeps sampling for the pre-set count maximum (time period), and the impact is transmitted to the receiver. Otherwise, if the flag is not set the system 28 stops sampling and goes back to sleep and any samples taken are effectively discarded.

Figure 15:
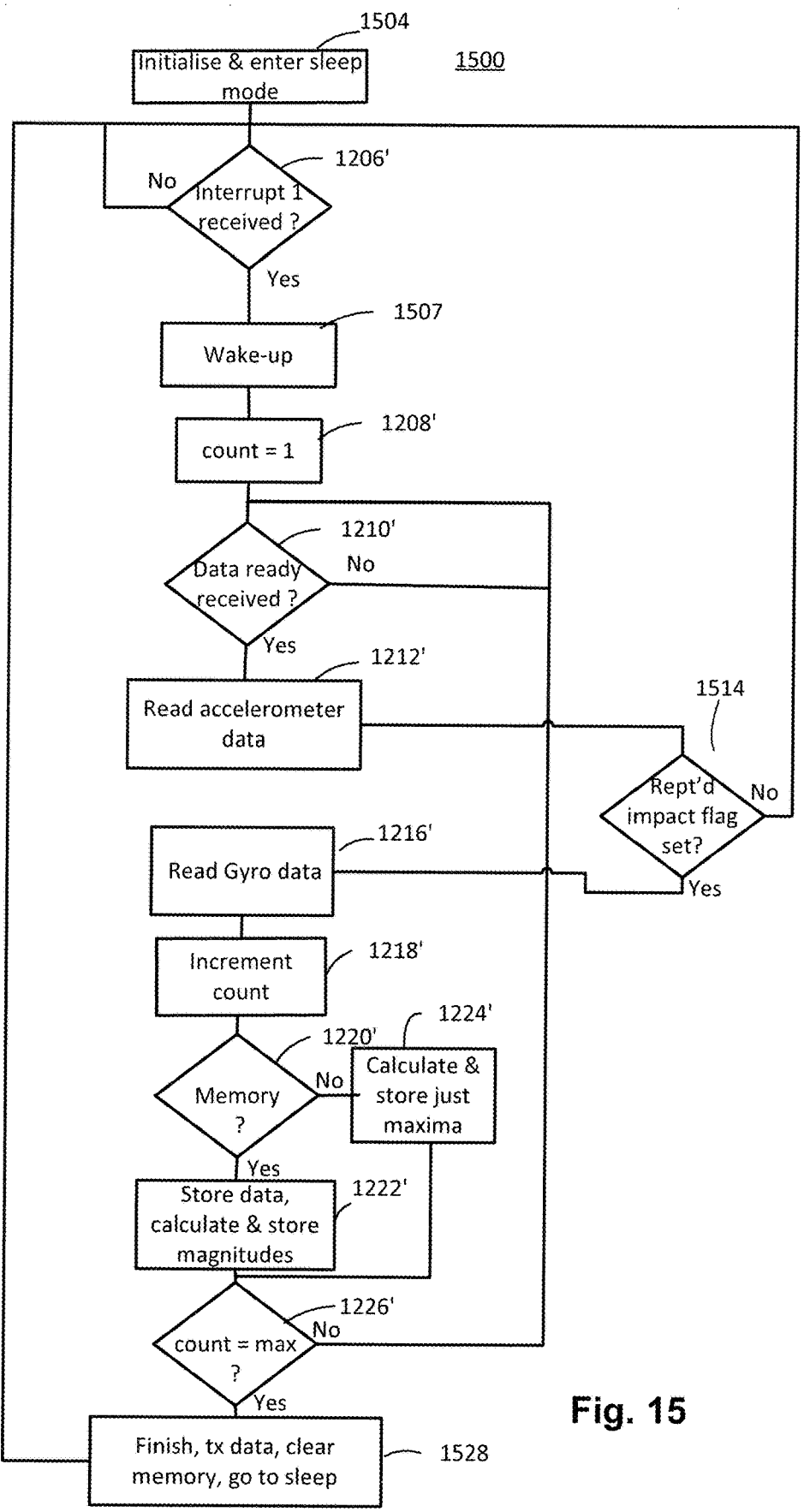
FIG. 15 is a process control flow diagram for a processor device in accordance with a fourth embodiment of the present disclosure.

An example of a decision step, 1514, is illustrated in the process flow control diagram of FIG. 15 where the decision step is placed between reading the accelerometer data, step 1212', and reading the gyro data, step 1216'. Such a decision step may also be implemented in the process flow control diagram illustrated in FIG. 13, and would also fall between steps 1212' and 1216,', and also implemented in the process flow control diagram illustrated in FIG. 12 falling between steps 1212 and 1216.

In the one or more described embodiments where one or more parts of the system are described as "going back to sleep" once the predetermined count or time period for taking samples has elapsed, the system or those parts of the system necessary for transmitting data to the monitoring station 32 remain active. All references made herein to orientation (e.g. front, rear, upper, lower, anterior and posterior) are made for the purposes of describing relative spatial arrangements of features, and are not intended to be limiting in any sense.

It will be understood by those skilled in the art that the drawings are merely diagrammatic and that further items of equipment may be required in a commercial apparatus. The position of such ancillary items of equipment forms no part of the present disclosure and is in accordance with conventional practice in the art.

Insofar as embodiments of the disclosure described above are implementable, at least in part, using a software-controlled programmable processing device such as a general purpose processor or special-purposes processor, digital signal processor, microprocessor, or other processing device, data processing apparatus or computer system it will be appreciated that a computer program for configuring a programmable device, apparatus or system to implement methods and apparatus is envisaged as an aspect of the present disclosure. The computer program may be embodied as any suitable type of code, such as source code, object code, compiled code, interpreted code, executable code, static code, dynamic code, and the like. The instructions may be implemented using any suitable high-level, low-level, object-oriented, visual, compiled and/or interpreted programming language, such as, Liberate, OCAP, MHP, Flash, HTML and associated languages, JavaScript, PHP, C, C++, Python, Nodejs, Java, BASIC, Perl, Matlab, Pascal, Visual BASIC, ActiveX, assembly language, machine code, and so forth. A skilled person would readily understand that term "computer" in its most general sense encompasses programmable devices such as referred to above, and data processing apparatus and computer systems.

Suitably, the computer program is stored on a carrier medium in machine readable form, for example the carrier medium may comprise memory, removable or non-removable media, erasable or non-erasable media, writeable or re-writeable media, digital or analog media, hard disk, floppy disk, Compact Disk Read Only Memory (CD-ROM), Company Disk Recordable (CD-R), Compact Disk Rewriteable (CD-RW), optical disk, magnetic media, magneto-optical media, removable memory cards or disks, various types of Digital Versatile Disk (DVD) subscriber identity module, tape, cassette solid-state memory.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment. Moreover, one or more features of different embodiments may be combined to create further embodiments not specifically described herein, and any one or more features may be combined consistent with their technical and operational compatibility. To the extent that one or more features from respective embodiments may not be combined without being inconsistent with the technical and/or operational compatibility such features from respective embodiments may be selected for combination which do not have such technical and/or operational compatibility. All such embodiments are contemplated within the scope of this disclosure.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the disclosure. This is done merely for convenience and to give a general sense of the disclosure. This description should be read to include one or at least one and the singular also includes the plural unless it is meant otherwise.

In view of the foregoing description it will be evident to a person skilled in the art that various modifications may be made within the scope of the disclosure.

For example, although embodiments have been described in which impact event data may be transmitted to a monitoring station in real-time, impact event data may be stored and downloaded wirelessly, or by wired coupling, at breaks in a match, e.g. half-time, or at the end of the match. This may be particularly suitable for non-professional environments and download may be to a device such as a smartphone or other mobile communication device running a suitable application.

One or more embodiments have been described in the context of acceleration monitoring. Optionally, monitoring circuitry, power sources and transmitter and/or receiver circuitry may be included for monitoring other factors such as, for example, physiological data, for example, hydration, temperature, electrolyte levels, amongst other things. Additionally, angular acceleration may be measure instead of angular velocity. Although a first embodiment has been described utilizing a H3LIS accelerometer, embodiments in accordance with the present disclosure are not limited to use of such an accelerometer. Additionally, control circuitry has been described implemented as a processor but the processor may comprise more than one processing resource and or discrete circuitry and circuit components.

The first embodiment has been described utilizing a timer implemented in processor 56 for determining the acceleration measurement window during which the accelerometer and gyroscopic unit 54 operate in a normal or at least non-sleep or non-low power mode. However, the acceleration measurement window may be implemented by way of a counter configured to count the number of acceleration outputs until it reaches a target count representative of a suitable window length and to reset the accelerometer 52 and gyroscopic unit 54 to sleep mode responsive to the target count being achieved. Optionally, a timer or counter may be implemented in the accelerometer 52.

In one or more embodiments, for example the first embodiment utilising the H3LIS module, the accelerometer 52 may be configured to produce a signal, such as a second interrupt signal, at intervals corresponding to when acceleration samples have been taken and are ready to be read by the processor 56. Processor 56 receives such a second interrupt signal and responsive to such a second interrupt signal initiates a read of the accelerometer 52 and the gyroscopic unit 54.

Examples of linear acceleration and angular acceleration provided herein are for the sport of rugby union football in which an impact event comprises both significant linear and angular acceleration. The angular acceleration causing a turning and twisting of the head which may cause multiple collisions of the brain with the interior of the skull. Other impact sports may have a different impact profile, for example NFL ("American") football tends to have a greater linear acceleration component than angular acceleration in an impact event compared to rugby union football. Studies have shown that impact events in ice hockey have acceleration profiles similar to those observed in rugby union football. Embodiments in accordance with the present disclosure are not limited to rugby union football or sports with similar impact event acceleration profiles but may be utilised in sports with other impact event acceleration profiles.

Although the first embodiment is described using the H3LIS with a maximum output rate of 10 Hz in the sleep mode it may be possible to configure the H3LIS to have a greater output rate when in sleep mode or to utilise a different module to achieve a higher sleep rate. Also, although embodiments have been described utilising the sum of the squares of the acceleration magnitude measured in each of the three axes it may be possible to configure the system to utilise the magnitude of only one or two of the respective axis vectors. In the described embodiments, acceleration is utilised to determine an impact event, either directly or indirectly in the case of the gyroscopic measurement which measures angular velocity the acceleration being determined from the angular velocity measurement. Optionally or additionally, force may be calculated if the mass of a user's head is known. In this way, it may be possible to personalise data collection of an impact event for a specific user utilising the mass of their head. Acceleration is representative of force for a specific mass undergoing acceleration and references to acceleration and indeed velocity when used to derive acceleration are references to values representative or at least proportional to a force.

Although the second, third and fourth embodiments have been described with the interrupt 1 signal acting or being interpreted as a clock signal once the sum of squares of the linear acceleration vector magnitudes exceeds the threshold, one or more embodiments may be implemented such that interrupt 1 signal is used as a clock signal whenever the H3LIS accelerometer 52 is operating. Such continuous operation of the interrupt 1 signal may consume more power than if the interrupt 2 signal was only activated once the threshold been exceeded. However, it may be the case that continuous operation of interrupt 2 signal is desirable in order for the processor 56 to read acceleration data as soon as possible after the threshold acceleration has been exceeded. The output rate may also be the sample rate at which the acceleration and/or angular velocity is measured in respective modules. Optionally, the provision of the values may be at a faster rate than the output rate. In the first embodiment, the rate at which the values are measured in the accelerometer may be slower in in the first mode compared to the second mode.

One or more embodiments have been described utilising angular acceleration (derived from angular velocity) to provide a part of the acceleration data. However, a simplified embodiment may be conceived in which the linear acceleration is all that is measured. It may be particularly suitable to measure linear acceleration in favour of angular acceleration because typically the gradient of the acceleration is greater for linear acceleration than for angular acceleration. Additionally, embodiments in accordance with the present disclosure have been described using a gyroscopic unit 54 which measures angular velocity. Although processor 34 of the monitoring system 32 has been referred to as deriving the angular acceleration from the angular velocity values, processor 56 may be used to calculate angular acceleration from the angular velocity values. However, one or more embodiments in accordance with the present disclosure may utilise circuitry which measures angular acceleration directly.

Specific features such as registers and bit settings have been described with reference to the second embodiment. However, such specific arrangements, or one or more thereof, may be utilised in the first embodiment as appropriate and in any suitable combination with the teaching of the first embodiment.

Although embodiments have been described in which the interrupt 1 signal Interrupt 1—LIS_INT1_PIN—RISING initiates the full data read cycle, one or more embodiments may detach LIS_INT1_PIN—RISING from processor 56 and attach a "sample the impact" interrupt pin rising signal to cause processor to read data output from the gyroscopic module 54. In such an embodiment, interrupt 1 would be reattached to LIS_INT1_PIN—RISING so as to indicate to processor when the next data output is ready for reading.

Although features, elements and steps are set forth in at least some claims in an order and ordinal numbering of signals and other elements do not necessarily prescribe an order but may be by way of labelling only and other orders are contemplated.

The specific embodiments have been described with reference to a mouthguard. However, one or more embodiments may be incorporated in an intra oral appliance that is not a mouthguard or sometimes called "gumshield". Such an intra oral appliance may be removable or maybe more permanently located in the oral cavity. One or more embodiments of an oral appliance may be located adjacent or close to the oral cavity are not necessarily within it.

In one or more embodiments, the angular motion may be measured around respective axes of rotation in mutually orthogonal directions (X', Y', Z'), where the mutually orthogonal axes (X', Y', Z') may be in different directions from those for the first or linear motion (X, Y, Z). Although at least one embodiment has been described in which the squares of the linear acceleration are calculated in on-board processor 56 and then transmitted to the central system, optionally the system may send the linear magnitude acceleration FIGS. (i.e. not their squares) with the squares being calculated in the central processor 34. However, such an embodiment calculates the square of an acceleration along an axis, or squares of linear accelerations along respective axes as appropriate, to decide if acceleration is over the threshold (strictly the sum of the squares of the 3 axes which may be calculated in the on-board processor 56 or a single linear acceleration utilised).

One or more embodiments have been described in which modules such as the accelerometer, processor and/or gyrometer are operative in a sleep mode until woken up into a higher power full data acquisition mode responsive to detection of an acceleration exceeding a threshold acceleration. However, as will be evident to persons of ordinary skill in the art, other modules and devices within the system may also be operative in a sleep mode until woken responsive to detection of the acceleration exceeding a threshold acceleration.

The scope of the present disclosure includes any novel feature or combination of features disclosed therein either explicitly or implicitly or any generalisation thereof irrespective of whether or not it relates to the claimed disclosure or mitigate against any or all of the problems addressed by the present disclosure. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

Concerning yet another aspect of the disclosure, a mouthguard (or gum-shield) is a piece of protective equipment worn by participants in sports, particularly contact sports. A mouth-guard is typically worn in an upper part of the mouth of the participant and is generally configured to cover at least a portion of the upper teeth of the participant. Most typically, a mouth-guard is configured to cover at least a portion of a vestibular (outer) surface of upper teeth of the wearer, at least a portion of a palatal (inner) surface of upper teeth of the wearer, and at least a portion of incisal and occlusal surfaces (i.e. "biting" and "chewing" surfaces) of upper teeth of the wearer.

In general outline, a mouth-guard according to one or more embodiments of the present disclosure can form a part of a system for the detection, measurement, characterisation, transmission, and/or reporting of impact events causing acceleration to be experienced by participants. Sensor components and/or monitoring element components located in the mouth-guard are used to monitor accelerations experienced by participants and data representative of such accelerations can be conveyed to a monitoring station for review by a technician, for example, a trained medical professional. This can allow the technician to make a decision regarding whether or not a participant in a sports match is fit to continue playing (e.g. following a particularly heavy head impact event) or should be removed from play and referred for further testing with a medical professional.

In the present description, the phrase "head impact event" relates to both direct impacts to the head and indirect impacts. That is, where the head receives a blow directly, or when a blow is sustained to some other body part and the force of the blow causes, amongst other things, an acceleration of the head. Further, reference is made to a participant sustaining an impact and their head experiencing an acceleration because of the impact. The acceleration of the head may be as a result of an impact directly to the head (i.e. a force is exerted on the head directly), or as result of an impact to another part of the body, but the result of which is that force is transmitted to the head from the point-of-impact through the body and neck. Such an acceleration may be termed an impact acceleration.

The sensor and/or monitoring element components are embedded and/or encapsulated in material from which the mouth-guard is formed.

FIG. 1 illustrates a mouth-guard 10 according to one or more embodiments of the present disclosure in which embedded and/or encapsulated components are arranged in a first arrangement. FIG. 2 illustrates a mouth-guard 10 according to one or more embodiments of the present disclosure in which embedded and/or encapsulated components are arranged in a second arrangement.

In the illustrated mouth-guard 10 of FIGS. 1 and 2, components are shown positioned in walls of the mouth-guard that are locatable at the rear of a mouth of a wearer when the mouth-guard is located correctly in the mouth.

The components are connected electronically by means of wires or circuit board (which may be flexible) and are communicatively coupled to a transceiver for transmitting data received from the components to a monitoring station in real-time. These components operate to collect and process impact event data, which can then be transmitted to the monitoring station via the transceiver.

Various terms used in dentistry are used in describing the mouth-guard 10 of one or more embodiments of the present disclosure. The terms used in this disclosure are listed below:

- Anterior—The direction towards the front of the head or the lips, as opposed to posterior, which refers to the directions towards the back of an individual's head. The term anterior teeth refers to incisors and canines, as opposed to premolars and molars, which are posterior teeth;
- Distal—The direction towards the gums beyond the tooth furthest from the midline (i.e. the 'most posterior tooth' or last tooth) in each quadrant of a dental arch, as opposed to mesial, which refers to the direction towards the midline;
- Incisal—The direction towards the biting edge of front teeth. This is a related term to occlusal, which relates to the analogous location on rear teeth;
- Mandibular—Relating to the mandible, or lower jaw;
- Maxillary—Relating to the maxilla, or upper jaw;
- Mesial—The direction towards the midline in a dental arch, as opposed to distal, which refers to the direction towards the gums beyond the tooth furthest from the anterior midline (the 'most posterior tooth' or last tooth) in each quadrant;
- Midline—Roughly, an imaginary vertical line dividing the left and right sides of the mouth at the teeth;
- Occlusal—The direction towards the biting surface of rear teeth. This is a related term to incisal, which relates to the analogous location on anterior teeth;
- Palatal—The side of a tooth adjacent to (or the direction towards) the palate, as opposed to vestibular, which refers to the side of a tooth adjacent to (or the direction towards) the inside of the cheek or lips of the mouth respectively;
- Posterior—The direction towards the back of an individual's head, as opposed to anterior, which refers to the directions towards an individual's lips. The term posterior teeth refers to premolars and molars, as opposed to incisors and canines, which are anterior teeth;
- Quadrant—The arrangement of teeth in a mouth is divided into four quarters. Upper and lower sets of teeth form an oval, which is divided into quadrants:
  - Upper right quadrant: upper right first incisor to upper right wisdom tooth;
  - Upper left quadrant: upper left first incisor to upper left wisdom tooth;
  - Lower right quadrant: lower right first incisor to lower right wisdom tooth;
  - Lower left quadrant: lower left first incisor to lower left wisdom tooth; and
- Vestibular—The side of a tooth that is adjacent to (or the direction towards) the inside of the cheeks and lips, as opposed palatal, which refers to the side of a tooth adjacent to the palate.

Additionally, reference is made to monitoring acceleration. In at least some implementations, a device used to measure acceleration is termed an "accelerometer". The terms "acceleration measurement", "acceleration monitoring" and the like include use of devices known as "accelerometers". The terms may be used interchangeably depending on context.

As illustrated in FIGS. 1 and 2, the mouth-guard 10 comprises a body 12 that defines a formation to be located around at least a portion of maxillary teeth of a wearer (i.e. teeth in the upper jaw of the wearer—hereinafter "upper teeth"), to cover, surround, and/or envelope the upper teeth of the wearer.

The body 12, formed from a plastics, resin, and/or rubber material, comprises a first wall 14 configured to cover at least a portion of an outer surface of the upper teeth of the wearer (i.e. the surface of the upper teeth that faces the inside of the upper lip and the cheek). In dentistry terminology this surface is known as a vestibular surface.

The body 12 comprises a second wall 16 configured to cover at least a portion of an inner surface of the upper teeth of the wearer (i.e. the surface of the upper teeth that faces the palate). In dentistry terminology this surface is known as a palatal surface.

The body 12 comprises a third wall 18 connecting the first and second walls 14, 16 and configured to cover at least a portion of biting edges and chewing surfaces of the upper teeth of the wearer (i.e. the edges and surfaces of the upper teeth that are opposed to the lower teeth). In dentistry terminology, these surfaces are known as incisal and occlusal surfaces.

The first, second and third walls 14, 16, 18 of body 12 define a channel 20 for receiving a plurality of teeth of a wearer. In the illustrated examples of FIGS. 1 and 2, the channel 20 is structured such that, when worn, it covers teeth that include the incisors of a wearer when the mouth-guard 10 is inserted.

In plan view, the body 12 of the mouth-guard 10 presents a generally symmetrical U-shaped configuration with "arms" extending away from a mid-line (denoted by dashed line 22 in FIGS. 1 and 2). The first, second and third walls 14, 16, 18 in one arm define a portion of the channel 20 that can receive teeth of an upper left quadrant. The first, second and third walls 14, 16, 18 in the other arm define a portion of the channel 20 that can receive teeth of an upper right quadrant.

The mouth-guard 10 also defines an open area 24, located between the two arms, which can allow a tongue of the wearer to touch their upper palate when the mouth-guard 10 is being worn. This may allow the user to maintain verbal communication with other participants (e.g. teammates) without requiring removal of the mouth-guard.

The mouth-guard 10 comprises a power source 26 (e.g. an electrical power battery) that is electrically connected to a system for monitoring motion 28. Typically, the power source 26 is of a type compatible with a wireless charger to allow recharging of the power source, i.e. the power source 26 may be wirelessly rechargeable, which allows the power source 26 to be charged/recharged without requiring removal from the mouth-guard 10.

In the illustrated example of FIG. 1, the power source 26 and system for monitoring motion 28 are located in a portion of the same arm of the mouth-guard. The portion in which they are located is in a distal direction from the mid-line 22. The power source 26 is located in the second wall 16 and the system for monitoring motion 28 is located in the first wall 14. The system for monitoring motion 28 is electrically connected to the power source 26 using a suitable connection (not shown) that runs: from the power source 26, through the third wall 18 to the system for monitoring motion 28.

Locating the power source 26 and system for monitoring motion 28 in a distal direction away from the mid-line 22 (i.e. so that these components are located in a portion of the mouth-guard 10 that is located in a rear part of the mouth of the wearer, when worn) may reduce the likelihood of damage to the power source 26 and system for monitoring motion 28 and/or teeth when the wearer sustains an impact. For instance, if the wearer undergoes a collision where a point of impact is at the front of the face of the wearer (e.g. at, or around, the mid-line of the upper teeth of the wearer), then damage to the power source 26 and system for monitoring motion 28 may be inhibited, because these components are located at positions away from the point of impact. Locating the power source 26 and system for monitoring motion 28 away from points of likely impact may reduce the likelihood of damage to teeth, because the "hard" bodies making up the housings of the power source 26 and system for monitoring motion 28 are in positions where they are less likely to be forced into the teeth.

Optionally, the power source 26 and system for monitoring motion 28 may be located in a different area of the mouth-guard 10 in one or more embodiments. FIG. 2 illustrates another example, in which the power source 26 and system for monitoring motion 28 are, again, located in a portion of the same arm of the mouth-guard. The portion in which they are located is in a distal direction from the mid-line 22. However, in the example illustrated in FIG. 2, the power source 26 and the system for monitoring motion 28 are located in the second wall 18.

In a mouth-guard 10 of the type illustrated in FIG. 2, likelihood of damage to the power source 26 and system for monitoring motion 28 when the wearer sustains an impact to the head may be reduced not only because the power source 26 and system for monitoring motion 28 are located in the mouth-guard 10 in a distal direction away from the mid-line 22 (i.e. so that these components are located in a portion of the mouth-guard 10 that is located in a rear part of the mouth of the wearer, when worn), but also because the power source 26 and system for monitoring motion 28 are located in a portion of the mouth-guard 10 that is locatable inside (i.e. on a palatal side of) the upper teeth. The teeth themselves can serve as a barrier to offer a level of protection to the components. In addition to the potential to inhibit damage during frontal impacts, the location of the components in the example of FIG. 2 may, in an instance where the wearer undergoes a collision where a point of impact is at the side of the face, inhibit damage to the power source 26 and system for monitoring motion 28, because these components are located at positions in which they are shielded, at least in part, by the teeth of the wearer. In the illustrated examples of FIGS. 1 and 2, the components of the mouth-guard 10, described above, are encapsulated (i.e. wholly embedded) within material forming the mouth-guard 10.

Figure 16:
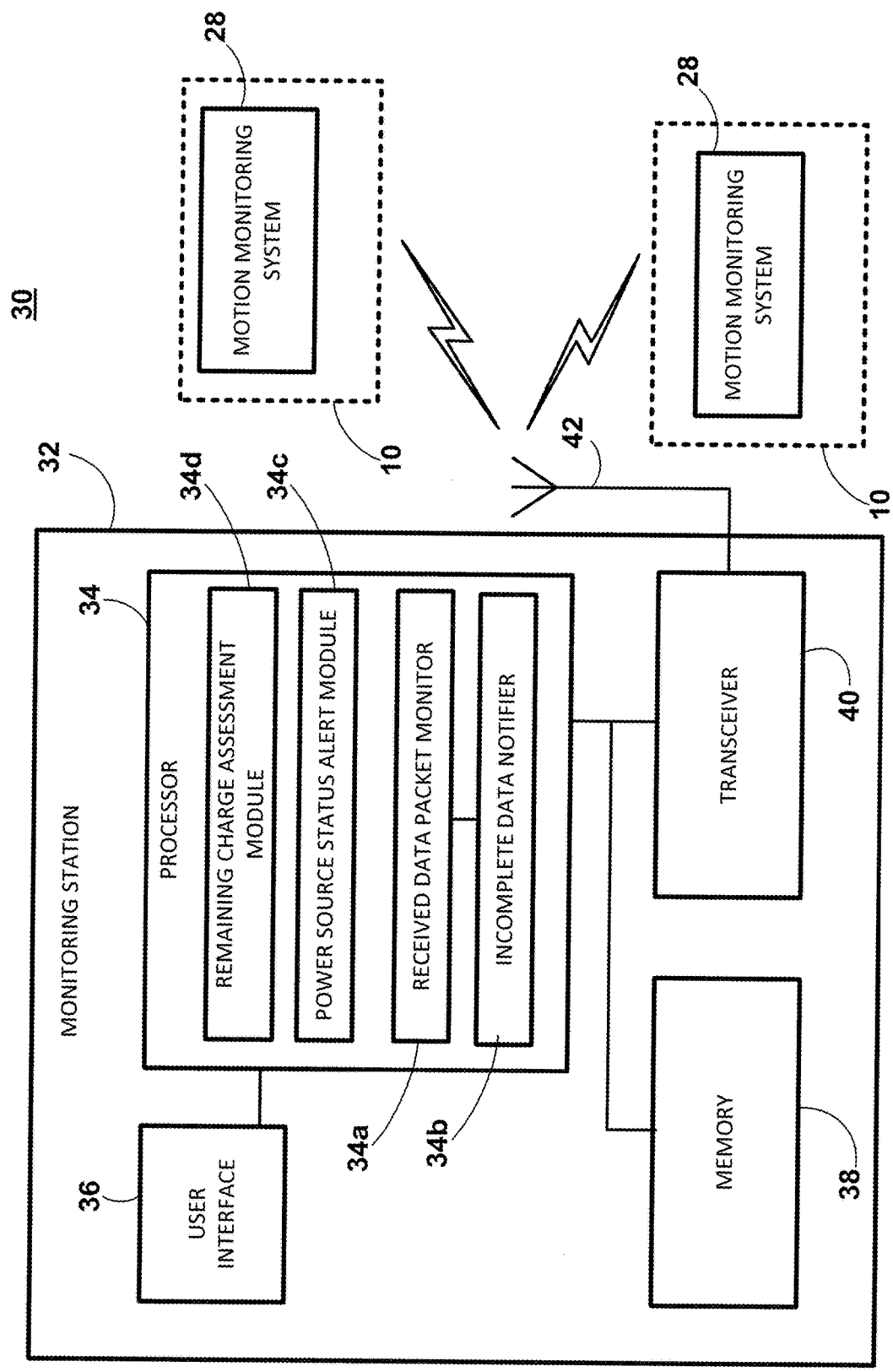
FIG. 16 illustrates a system for providing a monitoring environment for monitoring acceleration sustained by participants in a sporting event.

FIG. 16 illustrates a system 30 (i.e. an impact assessment system) for providing a monitoring environment for monitoring motion (e.g. acceleration) sustained by participants in a sporting event.

The system 30 operates to aggregate data representative of acceleration that occurs during impact events, the data being received from systems for monitoring motion 28 in mouth-guards 10 worn by game participants. The data can be conveyed to technicians, via the system, for assessing the seriousness of one or more impact events.

The system 30 comprises a monitoring station 32 that is in wireless communication with one or more systems for monitoring motion 28. The monitoring station 32 can communicate data received from the one or more systems for monitoring motion 28 to one or more devices (not shown in FIG. 16—see FIG. 5) either wirelessly or by wired communication link.

The monitoring station 32 includes a processor 34, a user interface 136, memory 38, and a transceiver 40. The monitoring station 32 wirelessly receives data representative of accelerations experienced by participants from each of the systems for monitoring motion 28. Signals from each of the systems for monitoring motion 28 are received at an antenna 42 coupled to the transceiver 40. The received signals are passed to the processor 34, which operates to process the data. Processed data is communicated to memory 38 for storage and can also be communicated to user interface 36, which is configured for communicating the data to an output device (e.g. to a display device via a communications network).

The monitoring station 32 is operative to receive acceleration data from the systems for monitoring motion 28. The monitoring station 32 is also operative to receive data representing other operating parameters and/or data of the motion monitoring systems 28 of each of the mouth-guards 10 (e.g. a power source status, such as charge level, device ID, "up-time", etc.), and/or historic impact data (e.g. number of impact events recorded by the motion monitoring system and/or data representative of the maximum acceleration value reached during a previous impact event).

The processor 34 of the monitoring station 32 operates to implement a received data packet monitor 34a, an incomplete data notifier 34b, a power source status alert module 34c, and a remaining charge assessment module 34d.

The received data packet monitor 34a operates to monitor transmissions received from one or more mouth-guards to determine if the transmissions contain a required number of data packets and to determine if data within each data packet is not erroneous.

Figure 18:
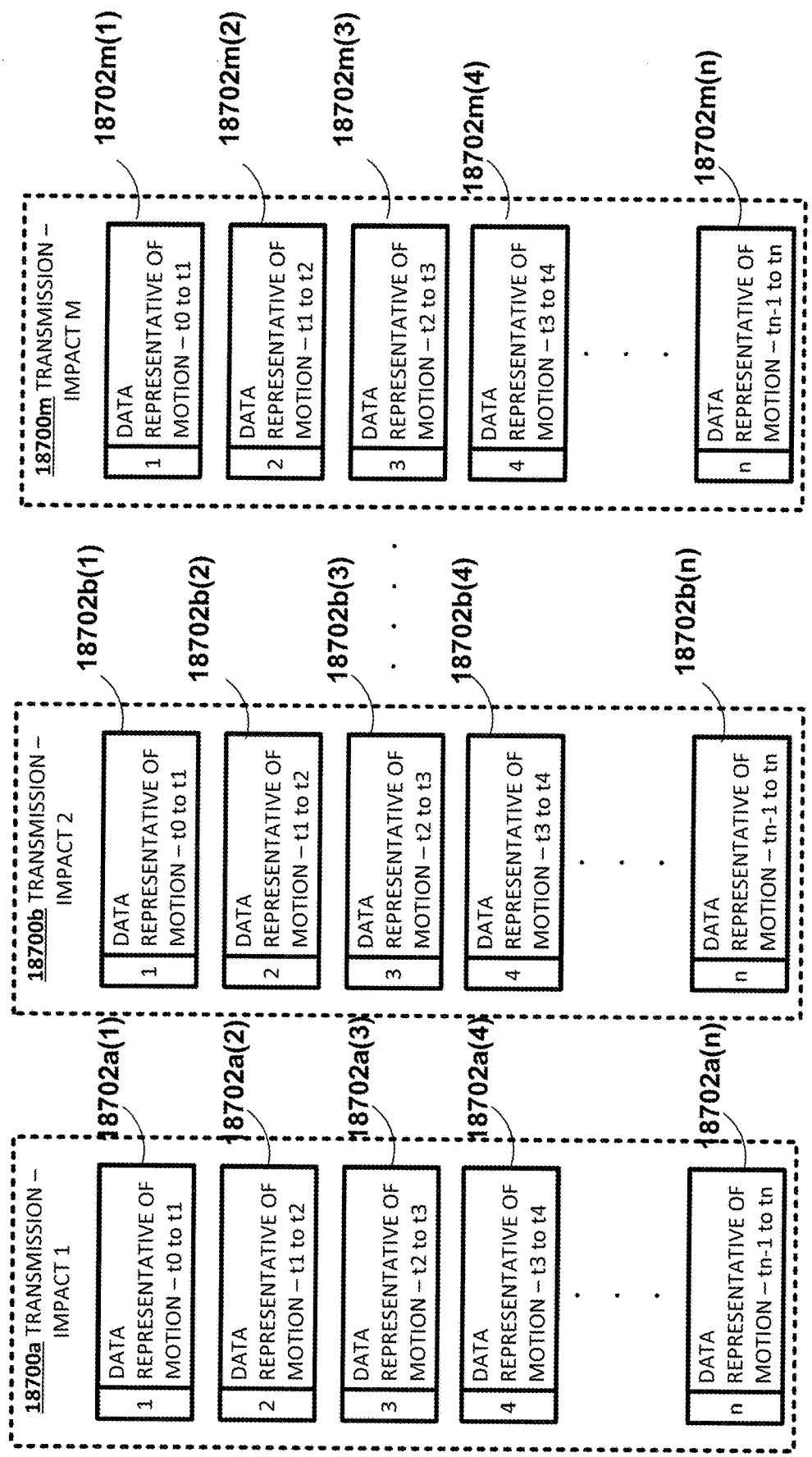
FIG. 18 schematically illustrates a plurality of separate transmissions sent from a motion monitoring system to a monitoring station, each transmission comprising a plurality of impact data packets.

In a particular example, a transmission containing data representative of an impact event may comprise 26 data packets. With reference to FIG. 18, transmissions 18700a, 18700b, . . . 18700m are sent to the monitoring station for each respective impact event (i.e. "a" to "m", where "a" is a first impact event and "m" is a "m$^{th}$" impact event recorded by a mouth-guard on a field of play. Each data packet 18702 of a transmission (e.g. 18700a(1) to 18700a(n) of a first transmission "a", where (1) is a first data packet of n data packets and (n) is a final data packet of n data packets) may contain an identifier (ID), which indicates the number of the data packet in the impact event. For example, a first data packet "1" comprises data obtained during a first period of an impact event, i.e. from t0 to t1, a second data packet "2" comprises data obtained during a second period of an impact event, i.e. from t1 to t2, and a final data packet "n" comprises data obtained during a final period of an impact event, i.e. from tn–1 to tn. Including an ID in each data packet associated with an impact event may allow a processor at a monitoring station to order the data packets correctly. This enables an impact event "profile" to be built, which may be used for the purposes of displaying the profile as a graph of, for example, acceleration vs time.

Each data packet associated with a particular impact event will also comprise data representative of an acceleration value for a respective period of the impact event.

If the received data packet monitor 34a determines that at least one of the data packets is missing from the plurality of data packets in a data packet transmission and/or at least one of the data packets comprises erroneous data, then this is communicated to the incomplete data notifier 34b. The incomplete data notifier 34b prepares a NACK message, which contains data identifying missing and/or erroneous data packets and a request for these data packets to be re-sent by the motion monitoring system 28. The NACK message is forward to the transceiver 40 for onward transmission to the motion monitoring system 28 of the mouth-guard 10 that sent the transmission at issue.

Status messages are received by the monitoring station 32 on a periodic basis from the motion monitoring system 28 of each mouth-guard 10. The data contained in these messages is stored in memory 38. Power source status alert module 34c operates to retrieve status data for a particular mouth-guard 10 from memory 38 and, first of all, extracts power source data from the retrieved status data. The power source status alert module 34c compares a value representative of charge level for the power source to a threshold value. If the value is greater than the threshold value, then the power source status alert module 34c communicates this information to remaining charge assessment module 34d, which operates to determine for how much longer the charge level value is likely to exceed the threshold value. If the value of this determined time period is equal to, or exceeds, a threshold time period, then this is indicative that the charge level of the power source is at least acceptable, and the remaining charge assessment module 34d takes no further action.

Upon comparison of the value representative of charge level for the power source to a threshold value, if the value is equal to, or less than, the threshold, the power source status alert module 34c initiates an alert message, which is communicated to user interface 36. The user interface 36 configures an output device to issue an alert (e.g. display of an alert message on a display). If, upon comparison of the value representative of charge level for the power source to a threshold value by the power source status alert module 34c, the value is greater than the threshold, but, upon comparison of a determined period to a threshold time period by the remaining charge assessment module 34d, the determined period is less than the threshold time period, the remaining charge assessment module 34d initiates a message indicative of impending low charge of the power source. The message is communicated to user interface 36, which configures an output device to issue an alert (e.g. display of an alert message on a display). The above described steps will be discussed further below in relation to FIG. 20b.

Figure 17:
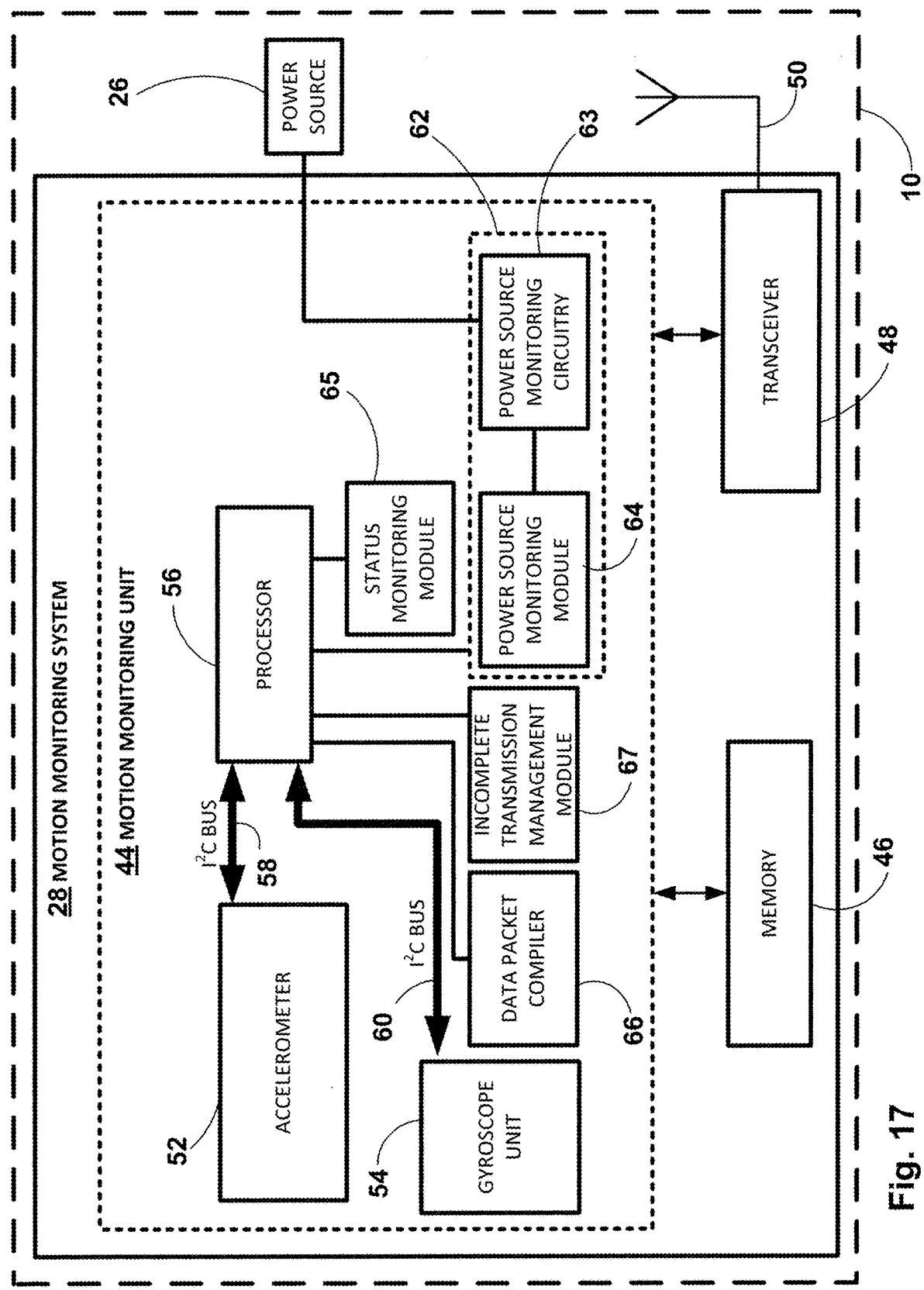
FIG. 17 illustrates components of a mouth-guard according to one or more embodiments of the present disclosure.

FIG. 17 illustrates components of the mouth-guard 10 (i.e. the power source 1726 and the system for monitoring motion 28 and) in more detail.

The system for monitoring motion 28 comprises a motion monitoring unit 44, a memory 46 and a transceiver 48. The motion monitoring unit 44 is operative to monitor acceleration experienced by a wearer of the mouth-guard 10, and is coupled to the memory 46, which serves to store data representative of acceleration monitored by the motion monitoring unit 44. The motion monitoring unit 44 is also coupled to the transceiver 48, which is operative to communicate a data signal containing data representative of acceleration monitored by the motion monitoring unit 44 to the monitoring station 32 via antenna 50. Data can also be received by the system for monitoring motion 28 from an external source via the antenna 50 and transceiver 48. Received data may comprise, for example, a negative-acknowledgement (NACK) signal (e.g. to indicate an error in data previously sent from the system for monitoring motion 28 and to request that the data be re-sent), software updates, etc.

The motion monitoring unit 44 comprises a three axis linear accelerometer 52, a gyroscope unit 54 and a processor 56. Each of the accelerometer 52 and the gyroscope unit 54 are communicatively coupled to the processor 56 by way of Inter-Integrated Circuit (I²C) buses 58, 60 respectively.

The accelerometer 52 is operative to monitor linear accelerations of the mouth-guard 10. The accelerometer 52 is operative to measure a linear acceleration in each orthogonal direction (x, y, z), e.g. of a Cartesian coordinate reference frame. A combination of respective acceleration values may be used to derive a linear acceleration vector.

The gyroscope unit 54 is operative to measure angular velocity to provide data representative of angular rotation. The gyroscope unit 54 is operative to measure angular velocity with respect to each orthogonal direction (x, y, z), e.g. of a Cartesian coordinate reference frame. A combination of respective angular velocity values may be used to derive an angular velocity vector.

The accelerometer 52 and gyroscope unit 54 are operative to monitor attributes of the environment of the mouth-guard 10 over time to determine a linear acceleration of the system for monitoring motion 28 and an angular velocity of the system for monitoring motion 28. Using data indicative of linear acceleration and angular velocity, which is communicated to the processor 56, the processor 56 is able to determine the fact of an event causing acceleration of a particular magnitude and a rotation. This data can be used in the system for monitoring motion 28 and/or the monitoring station 32, to calculate a vector representative of a magnitude of the linear acceleration and a vector representative of an angular velocity experienced by the system for monitoring acceleration 28.

Power source monitoring system 62 comprises power source monitoring circuitry 63, which is electrically coupled to the power source 26, and is configured to determine the voltage of the battery. The power source monitoring system 62 also comprises a power source monitoring module 64, which is implemented by processor 56, and which is configured to receive a signal output from the power source monitoring circuitry 63. Power source monitoring module 64 compares a value of a signal output by power source monitoring circuitry 63 (which comprises a voltage value representative of a charge-level of the power source 26) to a threshold voltage value (which represents a threshold charge level). If the voltage value from power source monitoring circuitry 63 is greater than the threshold voltage value, then power source monitoring module 64 communicates a signal to a status monitoring module 65 indicating that power source status is at least acceptable. However, if the power source monitoring module 64 determines that the voltage value from power source monitoring circuitry 63 is equal to, or less than, the threshold voltage value, (i.e. indicative of a sub-optimal power source operating parameter condition), then power source monitoring module 64 communicates a signal to status monitoring module 65 indicating that power source status is not acceptable.

The motion monitoring unit 44 also comprises status monitoring module 65, which is implemented by processor 56, and which operates to monitor the status of operating conditions and/or parameters of the motion monitoring unit 44 (e.g. a power source status, such as charge level, device ID, "up-time", etc.), and/or historic impact data (e.g. number of impact events recorded by the motion monitoring system and/or data representative of the maximum acceleration value reached during a previous impact event, or events, e.g. previous five maxima). The status monitoring module 65 operates to retrieve historic impact data from memory 46 and collate this data with data representative of operating conditions and/or parameters and forward the collated data to data packet compiler 66.

Figure 19:
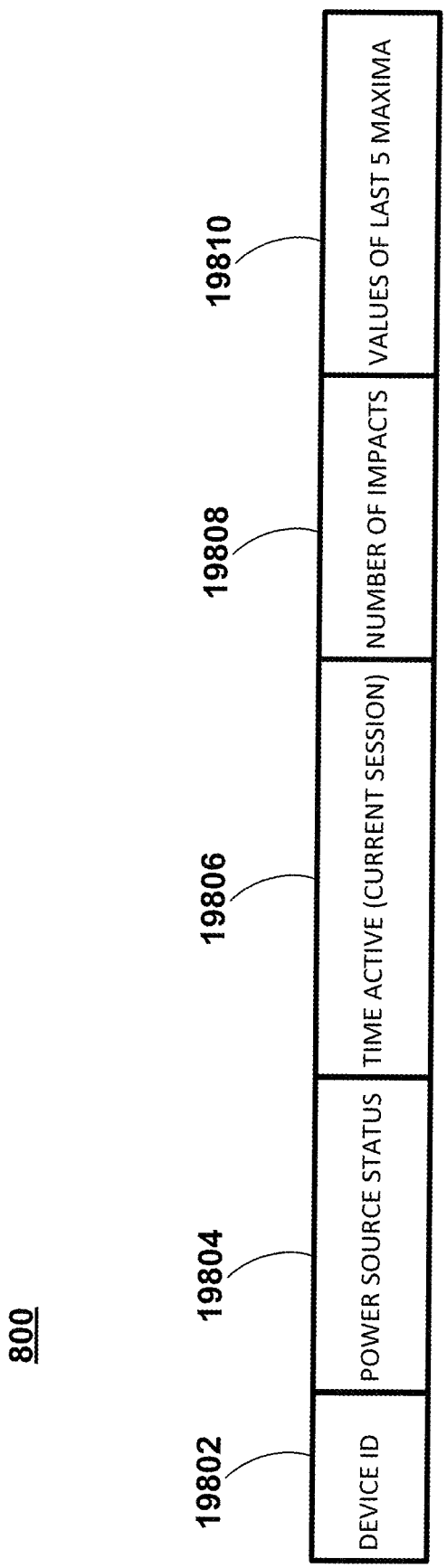
FIG. 19 schematically illustrates a transmission comprising a motion monitoring system status data packet.

The data packet compiler 66 is implemented by processor 56 and operates to create a status data packet for transmission to monitoring station. An example of a status data packet is illustrated in FIG. 19, which shows a data packet 19800 comprising: data 19802 representative of a device ID (e.g. an identification number specific to a particular mouth-guard 10); data 19804 representative of, for example, a charge level of a power source of the mouth-guard 10 ("power source status"); data 19806 representative of the time that the mouth-guard 10 has been in use during a current session; data 19808 representative of the number of impacts that have been recorded by the mouth-guard 10 during a current session; and data 19810 representative of the values of the maximum measured acceleration for a number of past recorded impacts (e.g. past five impacts).

In addition to compiling status data packet transmissions, which may be sent to monitoring station on a periodic basis (e.g. every 10 seconds), data packet compiler 66 also operates to compile impact event data packet transmissions, which may be compiled on a less frequent basis and only after an impact event has occurred.

The motion monitoring unit 44 also comprises incomplete transmission management module 67, which is implemented by processor 56 and which operates to monitor for incoming NACK messages transmitted from the monitoring station. If such a NACK message is received, incomplete transmission management module 67 operates to determine the number of an impact event to which the message relates (from information contained in the message), and also determines one or more specific data packets relating to the impact event (also from information contained in the message). The incomplete transmission module 67 operates to retrieve relevant data from memory 46 and configure the data in a message for transmission to monitoring station via transceiver 48.

FIG. 5 illustrates an impact assessment system 68 where impacts sustained by participants may be detected, recorded, analyzed, and reviewed, and FIG. 6 illustrates an example environment where the impact assessment system of FIG. 5 may be employed. In addition to data relating to impacts being communicated from the mouth-guards 10 to the monitoring station 32, data relating to a motion monitoring system 28 status (e.g. power source operating parameters) is also communicated to the monitoring station 32.

The impact assessment system 68 is operative to aggregate data representative of acceleration experienced by participants, i.e. the data received from the systems for monitoring motion 28 in mouth-guards 10 worn by participants, and can make the data available to relevant parties. The impact assessment system 68 also provides a system to allow review of the power source operating parameter conditions (e.g. to allow an operator to decide if one or more mouth-guards currently in use should be replaced, because, for example, charge level is too low).

One or more participants are fitted with a mouth-guard 10 comprising a system for monitoring motion 28 as described above. A monitoring station 32 (as described above) is located near to a field-of play so as to be within communication range of each system for monitoring motion 28. The monitoring station 32 is operative to receive data signals from each system for monitoring motion 28, with such data signals comprising data representative of acceleration experienced by each participant fitted with the mouth-guard 10 and also data signals comprising data representative of a status of each motion monitoring system 28.

The monitoring station 32 is in wireless communication with the one or more systems for monitoring motion 28 in the mouth-guards 10.

The monitoring station 32 is optionally in wired or wireless communication with a network 70 (e.g. a public or private data network). The network 70 is communicatively coupled (wired and/or wirelessly) to a database 72 and/or one or more user devices (such as, for example, a computer 74, a tablet device 76 and/or a smartphone 78).

Data received by the monitoring station 32 is analyzed and converted to a format that is suitable for presentation via a display of the one or more user devices. Data presented in this manner can be analyzed by a technician 82 (see FIG. 6) to assess participant well-being and, based upon the data, to make a determination whether or not a participant should be removed from the field-of-play 80 (see FIG. 6) following an impact event, or may continue to participate. Also analysis can take place of the power source operating parameter conditions of each mouth-guard 10 on the field-of-play. Dependent upon analysis, a determination may be made that replacement of one or more of the mouth-guards 10 may be necessary in order for monitoring to continue under acceptable power source operating parameter conditions.

Also, data received by the monitoring station is communicated to the database 72 for storage. Data stored in this manner may be retrievable at a later time for review by a technician.

The antenna 42 (see FIG. 6) of the monitoring station 32 is located in proximity to a field-of-play 80 so as to receive data signals from systems for monitoring motion 28 within mouth-guards 10 worn by participants on the field-of-play 80.

The antenna 42 of the monitoring station 32, in an example, comprises an omni-directional antenna positioned such that it is configured for the reception of data signals from the systems for monitoring motion within mouth-guards 10.

Figure 20A:
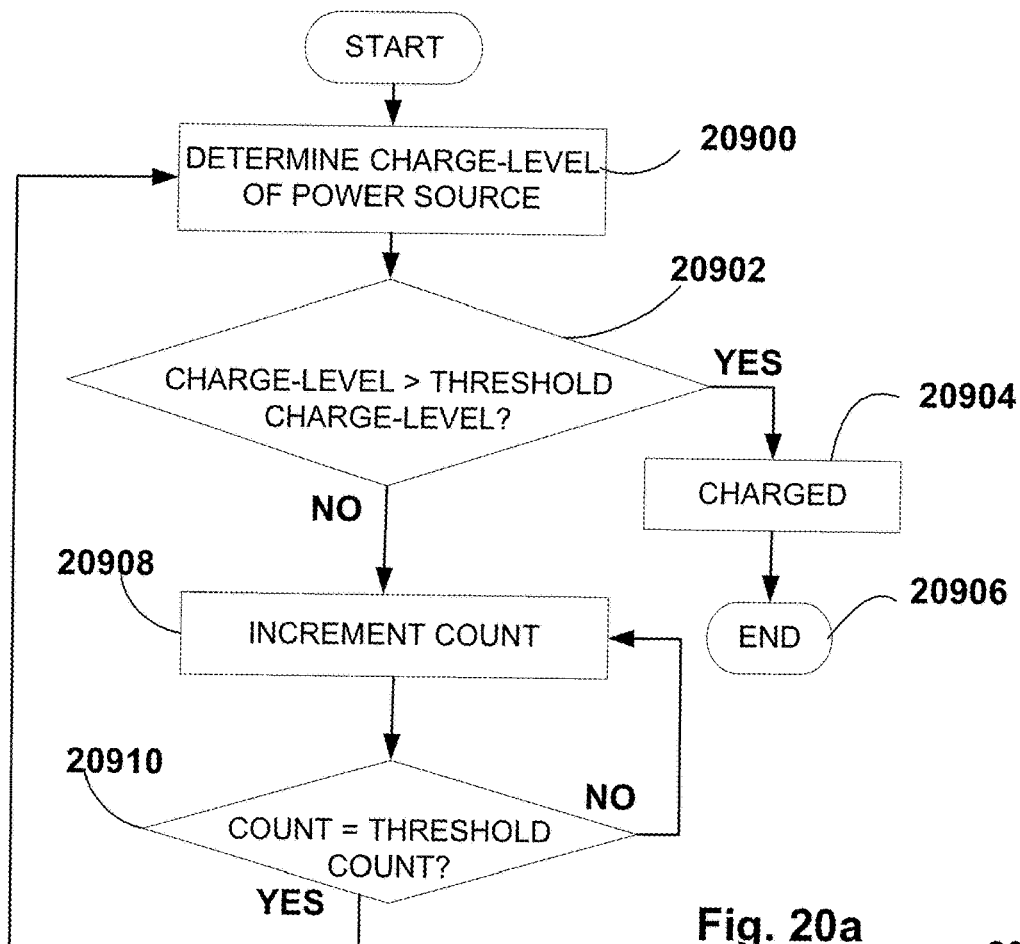
FIG. 20a schematically illustrates a process flow diagram, which illustrates steps implemented by a motion monitoring system to monitor charge status.

FIG. 20*a* schematically illustrates a process flow diagram, which illustrates steps implemented by power source monitoring system 62 and status monitoring module 63 of motion monitoring system 28.

In determining a charge-level of power source (step 20900), power source monitoring module 64 of power source monitoring system 62 receives a signal containing a value representative of a charge-level of the power source from power source monitoring circuitry 63. Power source monitoring module 64 compares the value obtained from the received signal to a threshold charge level (step 20902). If greater than the threshold charge level, the power source monitoring module 64 initiates issue of an instruction invoking an active state of the system, and the process proceeds to step 20904 where the status "CHARGED" is established and the charge routine illustrated in FIG. 20*a* ends, step 20906. For the avoidance of doubt, the status "CHARGED" may indicate a full or nearly full charge or a charge sufficient for the system to start or any charge in between as determined by a designer and/or operator of the system. If the "CHARGED" status is not indicative of a full charge then the process may continue and not proceed to step 20906.

If the value obtained from the received signal is equal to, or less than, the threshold charge level, then the power source monitoring module 64 causes a counter to be incremented (step 20908), which may be in a background process using a timer with the system in a "sleep" mode, and then conducts a comparison to determine if a count is equal to a threshold count (step 20910). If the value of the count is less than the threshold count, the power source monitoring module 64 causes the process to return to step 20908 and the count is incremented again followed by comparison of the count to the threshold count (step 20910). However, if the count equals the threshold count then the power source monitoring module causes the process to return to step 20900 and the charge-level is determined again.

The process "loop" of steps 20908 and 20910 can provide a "wait" or "sleep" period so that power source monitoring module 64 checks the charge-level of the power source at a specific period after a "low" charge-level determination is made.

Figure 20B:
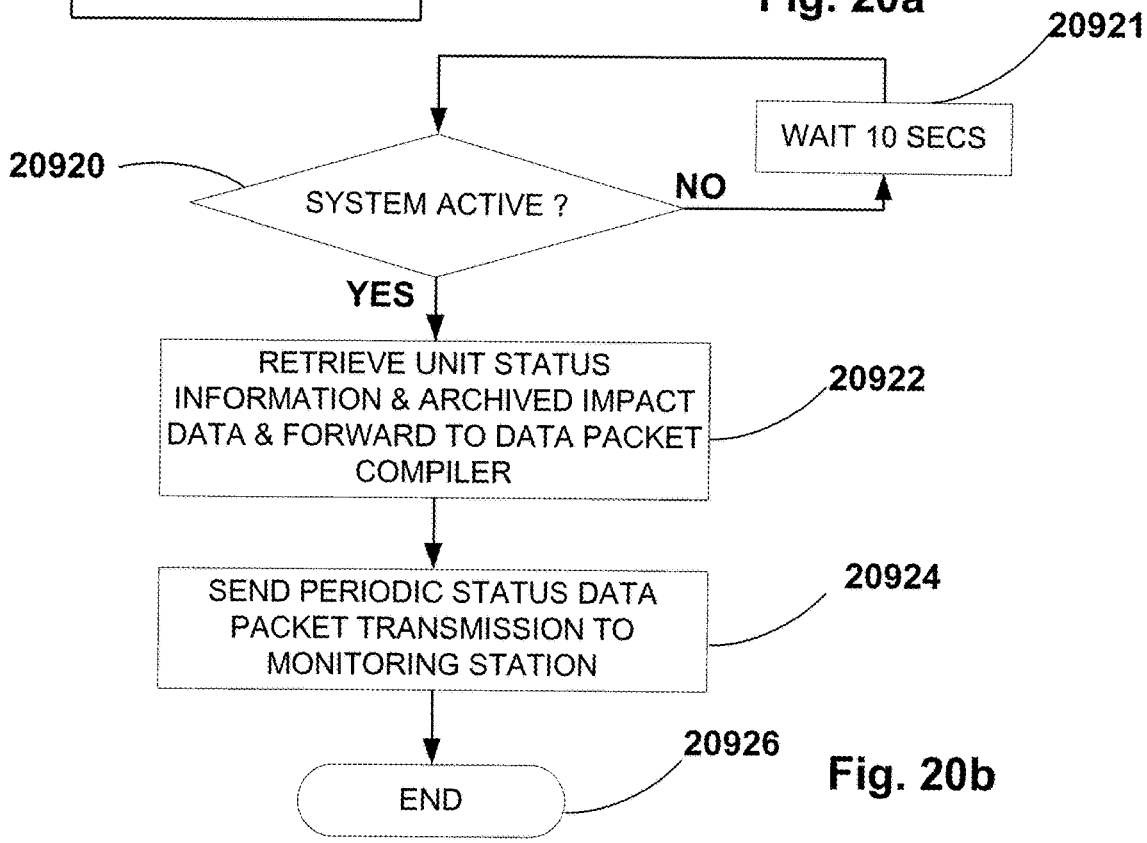
FIG. 20b schematically illustrates a process flow diagram, which illustrates steps implemented by a motion monitoring system to create a status update for transmission to a monitoring station.

Turning now to FIG. 20*b*, in step 20920 the status monitoring module 65, responsive to the instruction invoking the active state, retrieves historic impact data from memory 46 and collates this data with data representative of operating conditions and/or parameters of the system 28 and forwards the collated data to data packet compiler 66, step 20922. If the status monitoring module 65 does not note the system is active it continues to monitor for an active state. The data packet compiler 66 operates to create a status data packet for transmission to monitoring station. A status data packet is created and transmitted to the monitoring station on a periodic basis in this manner (step 20924) while the system is in an active state. The period at which status data packets are sent may, in an example, be every ten seconds, but other time periods may be employed in other arrangements.

Figure 20C:
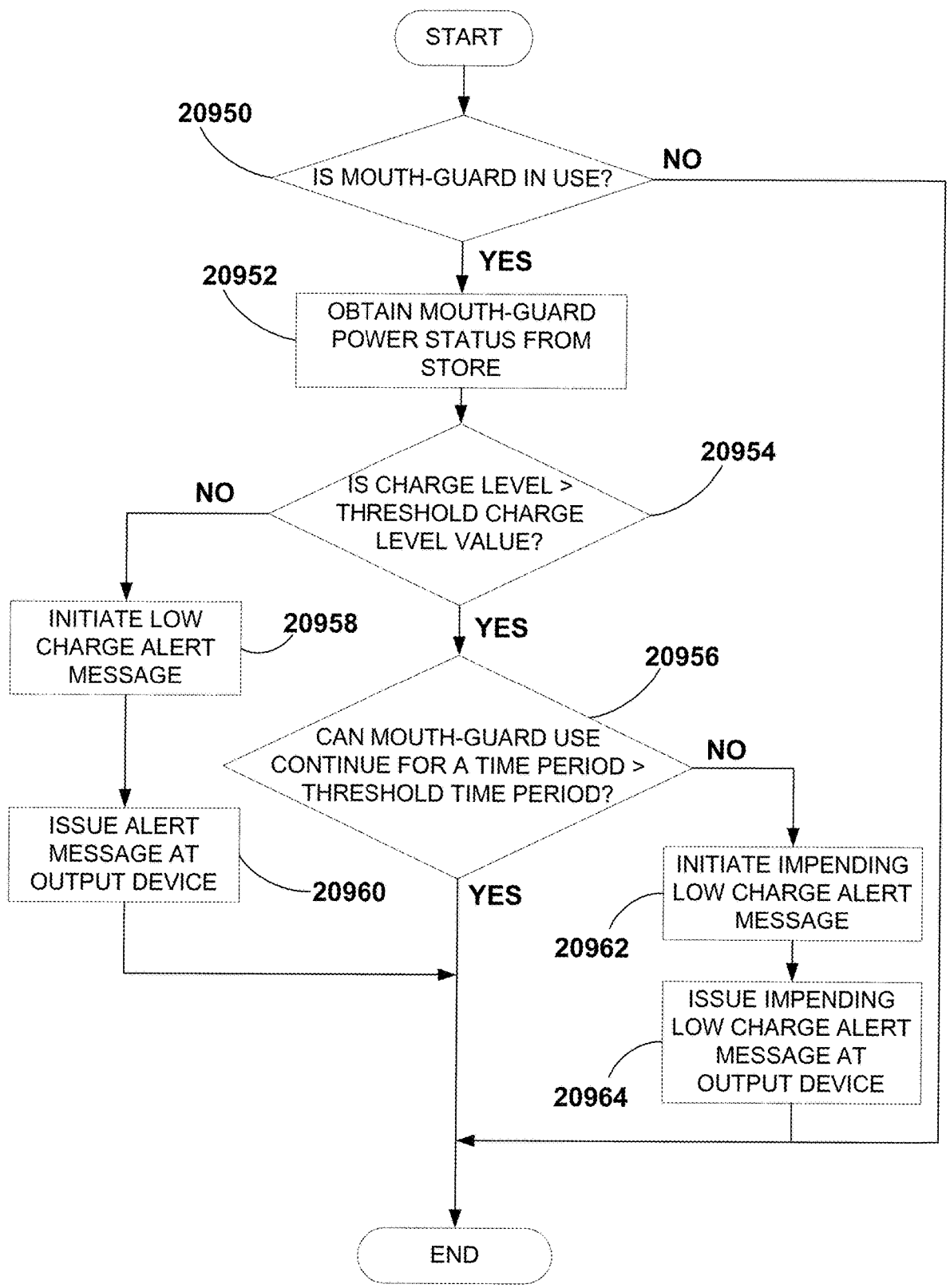
FIG. 20c schematically illustrates a process flow diagram, which illustrates steps implemented by a monitoring station of the impact assessment system.

FIG. 20*c* schematically illustrates a process flow diagram, which illustrates steps implemented by power source status alert module 34*c* and remaining charge assessment module 34*d* of monitoring station 32.

Status messages are received by the monitoring station 32 on a periodic basis from the motion monitoring system 28 of each mouth-guard 10. The data contained in these messages is stored in memory 38 of monitoring station 32.

Power source status alert module 34*c* operates to determine if a mouth-guard is in use, step 20950 and, if in use, retrieves power source data from the status data in the memory 38 (step 20952). The power source status alert module 34*c* compares a value representative of charge level for the power source to a threshold value (step 20954). If the value is greater than the threshold value, then the power source status alert module 34*c* communicates this information to remaining charge assessment module 34*d*, which operates to determine for how much longer the charge level value is likely to exceed the threshold value (step 20956). If the value of this determined time period is greater than a threshold time period, then this is indicative that the charge level of the power source is at least acceptable, and the remaining charge assessment module 34*d* takes no further action.

Upon comparison of the value representative of charge level for the power source to a threshold value, if the value is equal to, or less than, the threshold, the power source status alert module 34*c* initiates issue of an alert message (step 20958), which is communicated to user interface 36. The user interface 36 configures an output device to issue a low charge alert, step 20960 (e.g. display of an alert message on a display). If, upon comparison of the value representative of charge level for the power source to a threshold value by the power source status alert module 34*c* (i.e. step 20954), the value is greater than the threshold, but, upon comparison of a determined period to a threshold time period by the remaining charge assessment module 34*d* (i.e. step 20956), the determined period is equal to, or less than, the threshold time period, the remaining charge assessment module 34*d* initiates issue of a message indicative of impending low charge of the power source (step 20962). The message is communicated to user interface 36, which configures an output device to issue an impending low charge alert, step 20964 (e.g. display of an alert message on a display).

Figure 21:
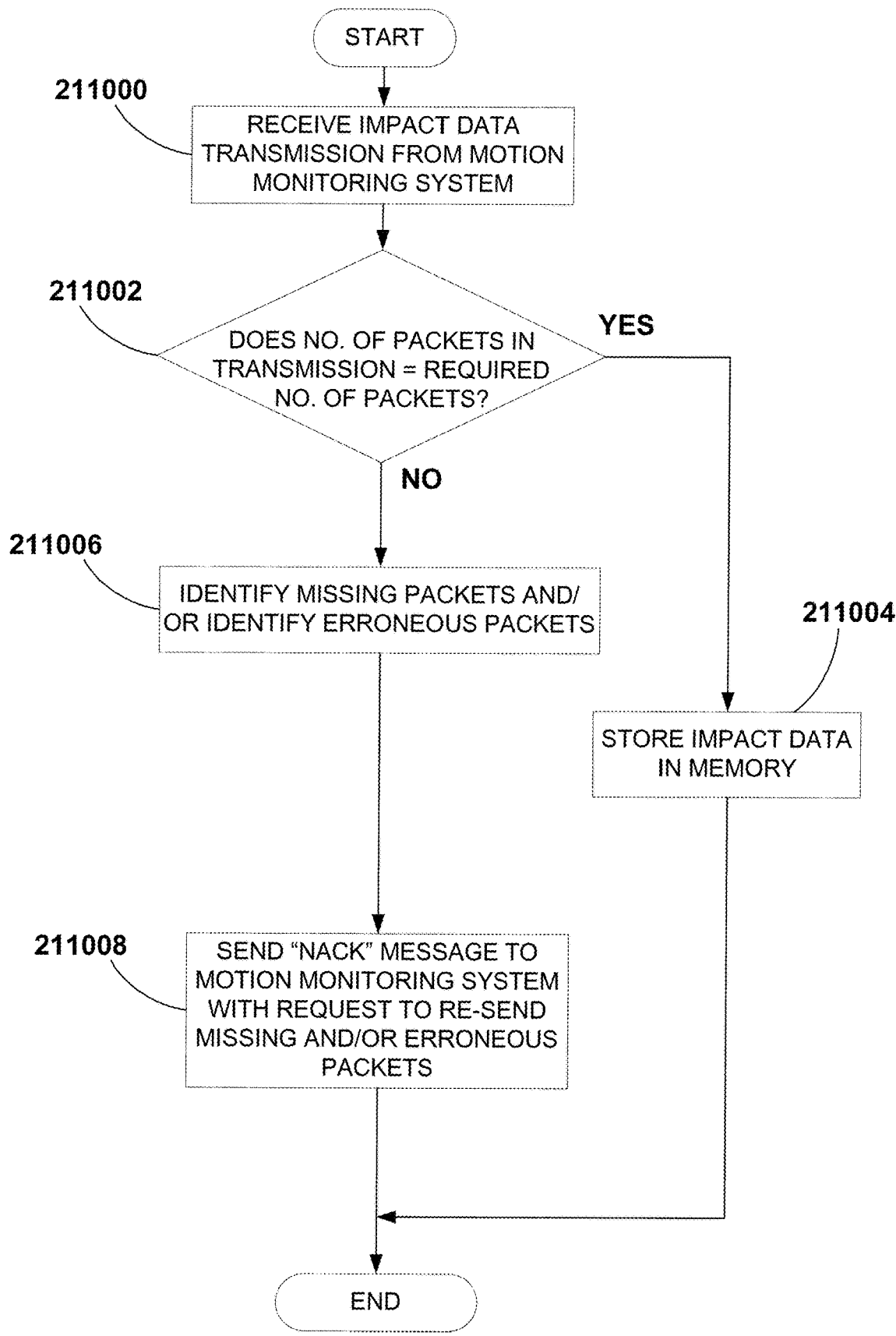
FIG. 21 schematically illustrates a process flow diagram, which illustrates steps implemented by the monitoring station of the impact assessment system to check for completeness of impact data received from the motion monitoring system.

FIG. 21 schematically illustrates a process flow diagram, which illustrates steps implemented by received data packet monitor 34*a* and incomplete data notifier 34*b* of monitoring station 32.

The received data packet monitor 34*a* operates to monitor transmissions received from respective motion monitoring systems of one or more mouth-guards to determine if the transmissions contain a required number of data packets and to determine if data within each data packet is not erroneous.

When an impact data transmission is received from a motion monitoring system (step 211000), received data packet monitor 34*a* determines if the number of data packets in the received transmission equals a required number of data packets (step 211002). If the correct number of data packets are present in the received transmission, the impact data contained in the data packets is stored in memory 38

(step 211004). However, if received data packet monitor 34*a* determines that at least one of the data packets is missing from the plurality of data packets in a data packet transmission and/or at least one of the data packets comprises erroneous data, then the received data packet monitor 34*a* operates to identify the missing packets and/or erroneous packets (step 211006) and communicates identified packet details to the incomplete data notifier 34*b*. The incomplete data notifier 34*b* prepares a NACK message, which contains data identifying missing and/or erroneous data packets and a request for these data packets to be re-sent by the motion monitoring system 28. The NACK message is forwarded to the transceiver 40 for transmission (step 211008) to the motion monitoring system 28 of the mouth-guard 10 that sent the transmission at issue.

Sending a message to a mouth-guard only when partial and/or erroneous transmissions are received may reduce a number of communications within the impact assessment system 68. This may reduce a burden on a bandwidth of the system, which may be limited. Also, by requiring mouth-guards to re-send data only when requested to do so, and only the missing and/or incorrect parts, this may reduce a drain on charge levels of the power sources of such mouth-guards, because the mouth-guards may be required to send fewer and/or smaller transmissions. Further, sending a portion of impact data for previous impact events in a status update may reduce the likelihood of the impact event data being missed. For example, if an impact data transmission is not received by the monitoring station, or a part of an impact data transmission is not received, despite repeated requests for the missing part to be re-sent, then the impact data contained in the status update should at least partially complete a missing data set and may ensure that at least maximum acceleration value data is received by the monitoring station. The system for monitoring motion 28 is typically formed from components mounted on a printed circuit board. The dimensions of the system for monitoring acceleration are optimized to achieve as small a foot-print as possible. This is to improve the integrity of a portion of the mouth-guard 10 where the system for monitoring acceleration 28 is located.

As will be appreciated, the system for monitoring motion 28, when encapsulated within material of the mouth-guard 10, is effectively sandwiched between material extending inwardly from a first surface of a wall in which the system for monitoring motion 28 is encapsulated and material extending inwardly from a second, opposed surface of the wall in which the system for monitoring motion 28 is encapsulated. A larger surface area of the system for monitoring motion 28 decreases the amount of material in contact between the opposed first and second surfaces. Therefore, by optimizing the dimensions of the system for monitoring motion 28 so as to decrease the foot-print, there will be an increase in the amount of material in contact between the opposed first and second surfaces. As a result, a weakness of the portion of the mouth-guard 10 where the system for monitoring motion 28 is encapsulated may be reduced (includes reduced air pockets and delamination). Thus, instances of failure of this portion during an impact (e.g. when a wearer may clench together the teeth of the upper and lower jaws, thereby increasing pressure on the mouth-guard 10) may be reduced.

Minimising the footprint of electronic components of the system for monitoring motion and a board, or boards, carrying the system may improve the integrity of the mouth-guard 10, because the volume of the mouth-guard 10 that is not occupied by material from which the mouth-guard 10 is formed is minimized. In particular, the space between external surfaces (i.e. first and second surfaces) of the wall of the mouth-guard 10 in which the system for monitoring motion 28 is encapsulated may be lessened, if the circuit board is smaller. This may improve the creation of a vacuum in the vacuum forming process and thus improve integrity of the mouth-guard 10. Specific implementations may include splitting the circuit board up to have smaller circuit board elements. Thus, although the system for monitoring motion 28 is represented by a single unit in the figures, it may, in optional arrangements, comprise multiple units, which are electrically coupled.

Also, minimizing the footprint of electronic components of the system for monitoring motion and a board, or boards carrying the system may provide for a more comfortable mouth-guard, because there are smaller deformities (from the electronic components) compared with known types of mouth-guards.

In the above described one or more embodiments, at least one operating parameter of the power source is monitored and controlled. The operating parameter of the power source may comprise at least one of: a power output level of the power source; a charge level of the power source; a state-of-health of the power source.

In the above described one or more embodiments data representative of impact events is transmitted to the monitoring station in real-time. However, optionally the data may be stored in memory on-board the mouth-guard for transmission at particular intervals, or may be stored for download at a later time.

In the above described one or more embodiments, the motion monitoring unit 44 comprises a gyroscope unit 54. However, optionally the gyroscope 54 may be replaced by an inertial measurement unit comprising a gyroscope, a magnetometer, and an accelerometer. An inertial measurement unit of this nature may be available in a single package and may comprise an LSM9DS1 microelectromechanical system (MEMS) from an iNEMO inertial module range, produced by STMicroelectronics of 39, Chemin du Champ des Filles Plan-Les-Ouates, Geneva, CH 1228, Switzerland.

Optionally, the accelerometer 52 of motion monitoring unit 44 comprises a H3LIS331DL MEMS motion sensor produced by STMicroelectronics of 39, Chemin du Champ des Filles Plan-Les-Ouates, Geneva, CH 1228, Switzerland.

In the above described one or more embodiments, the first, second and third walls 14, 16, 18 of body 12 define a channel 20 for receiving a plurality of teeth of a wearer, with the channel 20 structured so as to cover teeth that include the incisors of a wearer when the mouth-guard 10 is inserted. Optionally, it may be desirable to cover only parts of at least one of vestibular, palatal, incisal and occlusal surfaces in other arrangements, and so the mouth-guard may be configured to provide appropriate levels of surface cover as required.

In the above described one or more embodiments, the mouth-guard 10 comprises a body 12 that defines a formation to be located around at least a portion of maxillary teeth of a wearer (i.e. teeth in the upper jaw of the wearer), to cover, surround, and/or envelope the upper teeth of the wearer. Optionally, the mouth-guard 10 may comprise a body that defines a formation to be located around at least a portion of mandibular teeth of a wearer (i.e. teeth in the lower jaw of the wearer), to cover, surround, and/or envelope the lower teeth of the wearer. Further optionally, the mouth-guard 10 may be locatable around at least a portion of both maxillary and mandibular teeth of a wearer.

In the above described one or more embodiments, the mouth-guard 10 comprises an open area 24. Optionally, the space between the two arms may comprise a solid portion that covers the upper palate.

In the above described one or more embodiments, the memory 46 and transceiver 48 are shown as separate units from the motion monitoring unit 44. Optionally, the memory 46 and transceiver 48 may form part of a same device as the motion monitoring unit 44, e.g. a single unit comprising the motion monitoring unit 44, the memory 46 and the transceiver 48. Further optionally, the accelerometer 52, gyroscope unit 54, processor 56, memory 46 and transceiver 48 may be combined on multiple units in any combination. Yet further optionally, the accelerometer 52, gyroscope unit 54, processor 56, memory 46 and transceiver 48 may comprise individual, discrete units.

In the above described one or more embodiments, each of the motion monitoring unit 44 and the gyroscope unit 54 are communicatively coupled to the processor 56 by way of Inter-Integrated Circuit (I2C) buses 58, 60 respectively. Optionally, communicative coupling of the motion monitoring unit 44 and the gyroscope unit 54 to the processor 56 may be by any other suitable communication interface, e.g. Serial Peripheral Interface bus.

In the above described one or more embodiments, system for monitoring motion 28 is typically formed from components mounted on a printed circuit board. The printed circuit board may optionally comprise a flex-printed circuit and/or a rigid circuit board. In an optional arrangement, the printed circuit board may comprise both flexible portions and rigid portions, e.g. components of the system mounted on rigid portions with rigid portions connected to one another by flexible portions (i.e. a flex-rigid arrangement). In another optional arrangement, the printed circuit board may comprise both rigid portions, on which components of the system are mounted, with the rigid portions connected to one another by flexible electrical wire.

Optionally, the memory 46 may comprise flash memory and/or RAM and/or ROM.

In the above described one or more embodiments, the components of the mouth-guard are encapsulated (i.e. wholly embedded) within material forming the mouth-guard 10. Optionally, one or more of the components may be embedded, or partially encapsulated in the material forming the mouth-guard 10. Further optionally, the one or more components may be encapsulated within a second material, optionally a medically inert material (e.g. parylene C). The one or more components encapsulated with the second material may be partially embedded, or wholly embedded, within the material forming the mouth-guard 10.

Although the motion monitoring unit 44 includes a three axis accelerometer 52 and a three axis gyroscope unit 54 in the one or more embodiments described above, optionally other motion monitoring components may be used in other embodiments. For example, a two axis gyroscope in combination with a single axis gyroscope may be used instead of a three axis gyroscope. Also, a two axis accelerometer in combination with a single axis accelerometer may be used instead of a three axis accelerometer. Further, additional linear accelerometers may be used instead of a gyroscope.

In the above described one or more embodiments, the system for monitoring motion 28 and power source 26 may comprise separate elements, which are electrically connected by a connection lead. Optionally, the connection lead may comprise the antenna 50 of the system for monitoring motion 28, there being a high frequency/radio frequency coupling to the connection lead.

In the above described one or more embodiments, the antenna 42 comprises an omni-directional antenna so as to provide coverage of an entire field-of-play. Optionally, other antennas may be used e.g. with a narrower range of receiving angles. For example, multiple antennas with directionalities that individually do not allow for reception of signals from the entire field-of-play, but in combination receive signals from the entire field-of play may be used. For example, four antennas located at each corner of the field-of-play may be used to cover the entire field. This arrangement may also provide redundancy in the system so that, if a signal fails to be received by a closest antenna, it could, potentially, be received by another one of the four antennas.

All references made herein to orientation (e.g. front, rear, upper, lower, anterior and posterior) are made for the purposes of describing relative spatial arrangements of features, and are not intended to be limiting in any sense.

It will be understood by those skilled in the art that the drawings are merely diagrammatic and that further items of equipment may be required in a commercial apparatus. The position of such ancillary items of equipment forms no part of the present disclosure and is in accordance with conventional practice in the art.

Insofar as embodiments of the disclosure described above are implementable, at least in part, using a software-controlled programmable processing device such as a general purpose processor or special-purposes processor, digital signal processor, microprocessor, or other processing device, data processing apparatus or computer system it will be appreciated that a computer program for configuring a programmable device, apparatus or system to implement methods and apparatus is envisaged as an aspect of the present disclosure. The computer program may be embodied as any suitable type of code, such as source code, object code, compiled code, interpreted code, executable code, static code, dynamic code, and the like. The instructions may be implemented using any suitable high-level, low-level, object-oriented, visual, compiled and/or interpreted programming language, such as, Liberate, OCAP, MHP, Flash, HTML and associated languages, JavaScript, PHP, C, C++, Python, Nodejs, Java, BASIC, Perl, Matlab, Pascal, Visual BASIC, ActiveX, assembly language, machine code, and so forth. A skilled person would readily understand that term "computer" in its most general sense encompasses programmable devices as referred to above, and data processing apparatus and computer systems.

Suitably, the computer program is stored on a carrier medium in machine readable form, for example the carrier medium may comprise memory, removable or non-removable media, erasable or non-erasable media, writeable or re-writeable media, digital or analog media, hard disk, floppy disk, Compact Disk Read Only Memory (CD-ROM), Company Disk Recordable (CD-R), Compact Disk Rewriteable (CD-RW), optical disk, magnetic media, magneto-optical media, removable memory cards or disks, various types of Digital Versatile Disk (DVD) subscriber identity module, tape, cassette solid-state memory.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion.

For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the disclosure. This is done merely for convenience and to give a general sense of the disclosure. This description should be read to include one or at least one and the singular also includes the plural unless it is obvious that it is meant otherwise.

In view of the foregoing description it will be evident to a person skilled in the art that various modifications may be made within the scope of the disclosure.

For example, although embodiments have been described in which impact event data may be transmitted to a monitoring station in real-time, impact event data may be stored and downloaded wirelessly, or by wired coupling, at breaks in a match, e.g. half-time, or at the end of the match. This may be particularly suitable for non-professional environments and download may be to a device such as a smartphone or other mobile communication device running a suitable application.

One or more embodiments have been described in the context of acceleration monitoring. Optionally, monitoring circuitry, power sources and transmitter and/or receiver circuitry may be included for monitoring other factors such as, for example, physiological data, for example, hydration, temperature, electrolyte levels, amongst other things.

In one or more embodiments, the measurement of the actual battery voltage may be communicated to the monitoring station, optionally a "traffic light" system may be implemented to indicate the battery state.

The specific embodiments have been described with reference to a mouthguard. However, one or more embodiments may be incorporated in an intra oral appliance that is not a mouthguard or sometimes called "gumshield". Such an intra oral appliance may be removable or may be more permanently located in the oral cavity. One or more embodiments of an oral appliance may be located adjacent or close to the oral cavity are not necessarily within it.

The scope of the present disclosure includes any novel feature or combination of features disclosed therein either explicitly or implicitly or any generalisation thereof irrespective of whether or not it relates to the claimed disclosure or mitigate against any or all of the problems addressed by the present disclosure. The applicant hereby gives notice that new claims may be formulated to such features during prosecution of this application or of any such further application derived therefrom. In particular, with reference to the appended claims, features from dependent claims may be combined with those of the independent claims and features from respective independent claims may be combined in any appropriate manner and not merely in specific combinations enumerated in the claims.

Further aspects and embodiments in accordance with the present disclosure are now enumerated with reference to the following numbered clauses.

1. An oral appliance, such as a mouth guard for detecting acceleration experienced by a head of a wearer, the mouth-guard comprising:
   a body comprising a formation for extending around at least a portion of at least one of maxillary and mandibular teeth of a wearer and configured for location against at least a portion of at least one of maxillary and mandibular teeth at least at one of:
   an anterior teeth region of a mouth of the wearer;
   a posterior teeth region of a mouth of the wearer; and
   a position between the anterior and posterior teeth regions of a mouth of the wearer;
   a system for monitoring acceleration experienced by the mouth-guard and operative to communicate acceleration data to a monitoring station;
   a power source electrically coupled to the system for monitoring acceleration and for providing power thereto;
   wherein the power source is embedded within material of the body and is located within a region of the body that is locatable at a posterior teeth region of a mouth of a wearer, and further wherein the system for monitoring acceleration is embedded within the material of the body and is located within a region of the body that is locatable at a posterior teeth region of a mouth of a wearer.
2. A oral appliance according to clause 1, wherein the formation comprises a trench in which at least one of maxillary and mandibular teeth of a wearer are locatable, the trench defined by:
   a first wall configured to cover at least a portion of a vestibular surface of at least one of maxillary and mandibular teeth of a wearer;
   a second wall configured to cover at least a portion of a palatal surface of at least one of maxillary and mandibular teeth of a wearer; and
   a third wall connecting the first and second walls and configured to cover at least a portion of incisal and occlusal surfaces of at least one of maxillary and mandibular teeth of a wearer.
3. A oral appliance according to clause 2, wherein the power source is embedded within material of the second wall.
4. A oral appliance according to clause 2 or 3, wherein the system for monitoring acceleration is embedded within material of the second wall.
5. A oral appliance according to any one of clauses 2 to 4, wherein the system for monitoring acceleration is embedded within material of the first wall.
6. A mouth-guard according to any one of the preceding clauses, wherein the power source and/or the system for monitoring acceleration are encapsulated in an inert material.
7. An oral appliance according to clause 6, wherein the inert material comprises parylene C.
8. An oral appliance according to any one of the preceding clauses, wherein the power source and/or the system for monitoring acceleration are encapsulated in material of the body.
9. An oral appliance according to any one of the preceding clauses, wherein an antenna of the system for monitoring acceleration is located remote from the system for monitoring acceleration towards, or at, a region of the formation locatable against an anterior teeth region of the wearer.

10. An oral appliance according to clause 9, when directly or indirectly dependent upon clause 2, wherein the antenna is embedded within the protective material of the first wall.
11. An oral appliance according to any one of the preceding clauses, wherein the system for monitoring acceleration and the power source comprise separate discrete elements.
12. An oral appliance according to clause 11, wherein the system for monitoring acceleration and the power source are electrically connected by a connection lead.
13. An oral appliance according to clause 12, wherein the connection lead comprises an antenna of the system for monitoring acceleration.
14. An oral appliance according to any one of the preceding clauses, wherein at least one of:
    dimensions of components of the system for monitoring acceleration;
    dimensions of a circuit board upon which the system for monitoring acceleration is disposed;
    an arrangement and/or configuration of components of the system for monitoring acceleration upon a circuit board upon which the system for monitoring acceleration is disposed, are optimized and/or reduced to reduce a volume and/or footprint of the system for monitoring acceleration.
15. A device for wearing in the mouth for measuring physiological data, the device comprising:
    a formation for location against at least a portion of at least one maxillary tooth and/or at least one mandibular tooth of a wearer;
    monitoring circuitry for monitoring physiological data, the monitoring circuitry embedded within material of the formation; and
    a power source for providing power to the monitoring circuitry, the power source embedded within material of the formation.
16. A device according to clause 15, further comprising a transmitter communicatively coupled to the monitoring circuitry and operative to transmit physiological data received from the monitoring circuitry to a remote device.
17. A device according to clause 15 or 16, further comprising a receiver communicatively coupled to the monitoring circuitry and operative to communicate received data from a remote device to the monitoring circuitry.
18. A device according to any one of clauses 15 to 17, wherein said physiological data comprises at least one of: hydration; temperature; and electrolyte levels.
19. A system for monitoring acceleration of an intra oral appliance, comprising:
    control circuitry;
    a first motion measurement module operative to provide a value representative of a motion;
    wherein the first motion measurement module is operative in a first mode to provide a first motion value at a first rate and further operative to send a first signal to the control circuitry responsive to a first motion value criterion having been satisfied, and
    the control circuitry responsive to the first signal to send a second signal to the first motion measurement module to invoke a second mode operative to provide the first motion value at a second rate greater than or at least equal to the first rate;
    the first motion measurement module operative to send a third signal to the control circuitry indicative of a first motion value being available for reading;
    the control circuitry responsive to the third signal to initiate a read of a first motion value provided by the first motion measurement module.
20. A system according to clause 19, further comprising a second motion measurement module operative to provide a second motion value representative of a second motion; the control circuitry responsive to the first signal to send a fourth signal to the second motion measurement module to invoke a second motion measurement mode operative to measure a second motion, and to initiate a read of a second motion value provided by the second motion measurement module.
21. A system according to clause 19 or clause 20, wherein the control circuitry is operative in a low power mode pending receipt of the first signal from the first motion measurement module and invokes a second higher power mode responsive to receipt of the first signal.
22. A system according to clause 20 or clause 21, wherein the control circuitry is operative to initiate a read of the provided second motion value subsequent to initiating the read of the current first motion value.
23. A system according to clause 20 or any of clause 21 or clause 22 when dependent on clause 20, wherein the motion measurement module is operative such that the second rate is sufficient for the time period between chronologically adjacent third signals to encompass both reading the first motion value of the first motion measurement module and reading the second motion value of the second motion measurement module.
24. A system according to any of clause 19 to clause 23, wherein the first motion measurement module is operative in the second mode for a pre-set time period.
25. A system for monitoring acceleration of an intra oral appliance, comprising:
    control circuitry;
    a first motion measurement module operative to provide a value representative of a first motion;
    wherein the first motion measurement module is operative to provide the value representative of the first motion value at a rate;
    the first motion measurement module operative to send a first signal to the control circuitry responsive to the value representative of the first motion satisfying a criterion, the control circuitry responsive to the first signal operative to invoke a read mode for reading values representative of a first motion from the first motion measurement module; and wherein the first motion measurement module is operative to provide the value representative of the first motion at the rate for the control circuitry to read values representative of the first motion from the first motion measurement module for the control signal operative in the read mode.
26. A system according to clause 25, wherein the first signal is sent to the control circuitry at the rate following the value responsive to the first motion satisfying the criterion.
27. A system according to clause 25 or clause 26, further comprising a second motion measurement module operative to provide a value representative of a second motion; the control circuitry responsive to the first signal to read a value representative of a second motion.

28. A system according to any of clause 25 to clause 27, wherein the control circuitry is operative in a low power mode pending receipt of the first signal from the first motion measurement module and invokes the read mode at a higher power than the low power mode responsive to receipt of the first signal.

29. A system according to any of clause 27 or clause 28 dependent on clause 27, wherein the motion measurement module is operative such that the rate is sufficient for the control circuitry to read the value representative of the first motion value from the first motion measurement module and to read the value representative of the second motion value of the second motion measurement module within one cycle of the rate.

30. A system according to any of clause 25 to clause 29, wherein the control circuitry is operative in the read mode for a pre-set time period before ceasing the read mode.

31. A system according to clause 24 or clause 30, wherein the pre-set time period is at least sufficient for between 70 to 130 values to be provided, in particular sufficient for between 85 to 115 values to be provided, more particularly sufficient for between 95 to 110 values to be provided, yet more particularly sufficient for 104 values to be provided.

32. A system according to any of clause 19 to clause 24, wherein the first motion measurement module is responsive to a fifth signal indicative of the first motion value satisfying a second first motion value criterion to return to the first mode.

33. A system according to clause 32, wherein the second first motion value criterion comprises a first motion value less than a peak first motion value provided during the second mode.

34. A system according to clause 33, wherein the second first motion value criterion is provided during the second mode.

35. A system according to clause 33 or clause 34, wherein the fifth signal is internal to the first motion measurement module.

36. A system according to clause 35, wherein the first motion measurement module transmits a sixth signal to the control circuitry responsive to the fifth signal to indicate return to the first mode.

37. A system according to any of clause 33 or clause 34, wherein the fifth signal is generated in the control circuitry and transmitted to the first motion module to invoke the return to the first mode.

38. A system according to any of clause 19 to clause 37, wherein the first motion value comprises respective component first motion values representative of a first motion measured for each of mutually orthogonal directions (X, Y, Z).

39. A system according to clause 20 or any of clause 21 to clause 37 dependent on clause 21, wherein the second motion value comprises respective component values representative of a second motion measured for each of mutually orthogonal directions (X, Y, Z).

40. A system according to any of clause 19 to clause 39, wherein the first motion measurement module is operative to determine a first motion vector from the first motion measured for each of mutually orthogonal directions (X, Y, Z) and provide the first motion vector as the first motion value.

41. A system according to any of clause 19 to clause 40, wherein the first motion measurement module is operative to sample first motion values measured for each of mutually orthogonal directions (X, Y, Z) and provide the first motion values to the control circuitry.

42. A system according to any of clause 19 to clause 41, wherein the first motion is a linear motion.

43. A system according to clause 42, wherein the linear motion is linear acceleration and the first motion measurement module is a linear acceleration measurement module.

44. A system according to clause 43, wherein the linear acceleration measurement module is an accelerometer.

45. A system according to clause 20 or any of clause 21 to clause 25 dependent on clause 20 or clause 28 or any of clause 29 to clause 31 dependent on clause 28, wherein the second motion is an angular motion.

46. A system according to clause 45, wherein the angular motion is angular velocity and the second motion measurement module is an angular velocity measurement module.

47. A method for monitoring acceleration of an intra oral appliance, comprising:
operating a first motion measurement module in a first mode to
provide a first motion value at a first rate and to send a first signal to control circuitry responsive to a first motion value criterion having been satisfied, and
operating the control circuitry to respond to the first signal by sending a second signal to the first motion measurement module to invoke a second mode to provide the first motion value at a second rate greater than or at least equal to the first rate;
operating the first motion measurement module to send a third signal to the control circuitry indicative of a first motion value being available for reading; and
operating the control circuitry to initiate, responsive to the third signal, a read of a first motion value provided by the first motion measurement module.

48. A method according to clause 47, further comprising operating a second motion measurement module to provide a second motion value representative of a second motion; and operating the control circuitry to send a fourth signal to the second motion measurement module to invoke a second motion measurement mode to measure a second motion responsive to the first signal and to initiate a read of a second motion value of the second motion measurement module.

49. A method according to clause 47 or clause 30, further comprising operating the control circuitry in a low power mode pending receipt of the first signal from the first motion measurement module and invoking a second higher power mode responsive to receipt of the first signal.

50. A method according to clause 47 or any of clause 48 to clause 49 dependent on clause 47, wherein the control circuitry is operative to initiate a read of the provided second motion value subsequent to initiating the read of the current first motion value.

51. A method according to clause 48 or any of clause 49 to clause 50 dependent on clause 48, further comprising operating the motion measurement module such that the second rate is sufficient for the time period between chronologically adjacent third signals to encompass both reading the first motion value of the first motion measurement module and reading the second motion value of the second motion measurement module.

52. A method according to any of clause 47 to clause 51, further comprising operating the first motion measurement module in the second mode for a pre-set time period.
53. A method for monitoring acceleration of an intra oral appliance, comprising:
    operating a first motion measurement module to provide a value representative of a first motion at a rate;
    operating the first motion measurement module to send a first signal to the control circuitry responsive to the value representative of the first motion satisfying a criterion;
    operating the control circuitry to respond to the first signal by invoking a read mode for reading values representative of the first motion from the first motion measurement module;
    operating the first motion measurement module to provide the value representative of the first motion at the rate; and
    operating the control circuitry to read values representative of the first motion from the first motion measurement module provided at the rate in the read mode.
54. A method according to clause 53, further comprising operating the first motion measurement module to send the second signal to the control circuitry at the rate.
55. A method according to clause 53 or clause 54, further comprising operating a second motion measurement module to provide a value representative of a second motion; and
    operating the control circuitry to respond to the second signal to initiate a read of the value representative of a second motion subsequent to the read of the value representative of the first motion for the control circuitry operating in the read mode.
56. A method according to any of clause 53 to clause 55, further comprising operating the control circuitry in a low power mode pending receipt of the first signal from the first motion measurement module and invoking the read mode at a higher power than the low power mode responsive to receipt of the first signal.
57. A method according to any of clause 55 or clause 56 dependent on clause 54, further comprising operating the motion measurement module such that the rate is sufficient for the control circuitry to read the value representative of the first motion value from the first motion measurement module and to read the value representative of the second motion value of the second motion measurement module within one cycle of the rate.
58. A method according to clause 53 to clause 57, wherein the control circuitry is operative in the read mode for a pre-set time period before ceasing the read mode.
59. A method according to clause 52 or clause 58, wherein the pre-set time period is at least sufficient for between 70 to 130 values to be provided, in particular sufficient for between 85 to 115 values to be provided, more particularly sufficient for between 95 to 110 values to be provided, yet more particularly sufficient for 104 values to be provided.
60. A method according to any of clause 47 to clause 52, further comprising operating the first motion measurement module to respond to a fifth signal indicative of the first motion value satisfying a second first motion value criterion to return to the first mode.
61. A method according to clause 60, wherein the second first motion value criterion comprises a first motion value less than a peak first motion value provided during the second mode.
62. A method according to clause 61, wherein the second first motion value criterion is provided during the second mode.
63. A method according to clause 61 or clause 62, wherein the fifth signal is internal to the first motion measurement module.
64. A method according to clause 63, further comprising operating the first motion measurement module to transmit a sixth signal to the control circuitry responsive to the fifth signal to indicate return to the first mode.
65. A method according to any of clause 61 or clause 62, further comprising generating the fifth signal in the control circuitry and transmitting the fifth signal to the first motion module to invoke the return to the first mode.
66. A method according to any of clause 47 to clause 65, further comprising operating the first motion measurement module to determine a first motion vector from the first motion measured for each of mutually orthogonal directions (X, Y, Z) and provide the first motion vector as the first motion value.
67. A method according to any of clause 47 to clause 54, further comprising operating the first motion measurement module to sample first motion values measured for each of mutually orthogonal directions (X, Y, Z) and provide the sampled first motion values to the control circuitry.
68. A method according to any of clause 47 to clause 67, wherein the first motion is a linear motion.
69. A method according to clause 68, wherein the linear motion is linear acceleration and the first motion measurement module is a linear acceleration measurement module.
70. A method according to clause 69, wherein the linear acceleration measurement module is an accelerometer.
71. A method according to clause 48 or any of clause 49 to clause 52 dependent on clause 48 or clause 53 or any of clause 54 to clause 58 dependent on clause 53, wherein the second motion is an angular motion.
72. A method according to clause 71, wherein the angular motion is angular velocity and the second motion measurement module is an angular velocity measurement module.
73. A computer program comprising computer program elements, operative in one or more processor resources to implement a method according to any of clause 47 to clause 72.
74. A computer program carrier medium, carrying a computer program according to clause 73.
75. A computer program carrier medium according to clause 74, the carrier medium comprising a one or more of: memory, in particular electronic or optical memory, removable or non-removable media, erasable or non-erasable media, writeable or re-writeable media, digital or analog media, hard disk, floppy disk, Compact Disk Read Only Memory (CD-ROM), Company Disk Recordable (CD-R), Compact Disk Rewriteable (CD-RW), optical disk, magnetic media, magneto-optical media, removable memory cards or disks, various types of Digital Versatile Disk (DVD) subscriber identity module, tape cassette, solid-state memory, an electronic or electrical signal, an optical signal, a radio frequency signal.

76. A system according to any of clause 19 to clause 46, wherein the intra oral appliance is removable.

77. A system according to any of clause 47 to clause 46 or clause 76, wherein the intra oral appliance is a mouth guard.

78. A method according to any of clause 47 to clause 72, wherein the intra oral appliance is removable.

79. A system according to any of clause 47 or clause 72 or clause 78, wherein the intra oral appliance is a mouth guard.

80. A system for monitoring acceleration of an intra oral appliance, comprising:
   control circuitry;
   a first motion measurement module operative to provide a value representative of a first motion; and
   a second motion measurement module operative to provide a second motion value representative of a second motion;
   wherein the first motion measurement module is operative in a first mode to provide a first motion value at a first rate and further operative to send a first signal to the control circuitry responsive to a first motion value criterion having been satisfied, and
   the control circuitry responsive to the first signal to:
      send a second signal to the first motion measurement module to invoke a second mode operative to provide the first motion value at a second rate greater than or at least equal to the first rate; and
      send a "wake up" signal to the second motion measurement module to invoke a second motion measurement mode from a low power mode;
   the first motion measurement module operative to send a third signal to the control circuitry indicative of a first motion value being available for reading;
   the control circuitry responsive to the third signal to initiate a read of a first motion value provided by the first motion measurement module and a read of a second motion value provided by the second motion measurement module.

81. A system for monitoring acceleration of an intra oral appliance, comprising:
   control circuitry;
   a first motion measurement module operative to provide a value representative of a first motion;
   wherein the first motion measurement module is operative to provide the value representative of the first motion value at a rate; and
   a second motion measurement module operative to provide a second motion value representative of a second motion;
   the first motion measurement module operative to send a first signal to the control circuitry responsive to the value representative of the first motion satisfying a criterion, the control circuitry responsive to the first signal to:
      send a "wake up" signal to the second motion measurement module to invoke a second motion measurement mode operative to provide the second motion value;
      invoke a read mode for reading values representative of a first motion from the first motion measurement module; and
   wherein the first motion measurement module is operative to provide the value representative of the first motion at the rate for the control circuitry to read values representative of the first motion from the first motion measurement module and read values representative of the second motion value from the second motion measurement module, for the control signal operative in the read mode.

82. A system for monitoring acceleration of an intra oral appliance, comprising:
   control circuitry operative in a first control circuitry low power sleep mode and a second control circuitry higher power normal operation mode;
   a first motion measurement module operative to provide a value representative of a first motion; and
   a second motion measurement module operative to provide a second motion value representative of a second motion;
   wherein the first motion measurement module is operative in a first mode to provide a first motion value at a first rate and further operative to send a first signal to the control circuitry responsive to a first motion value criterion having been satisfied, and
   the control circuitry responsive to the first signal in the first control circuitry mode to:
      invoke the second control circuitry mode and in the second control circuitry mode;
      send a second signal to the first motion measurement module to invoke a second mode operative to provide the first motion value at a second rate greater than or at least equal to the first rate; and
      send a "wake up" signal to the second motion measurement module to invoke a second motion measurement mode from a low power mode;
   the first motion measurement module operative to send a third signal to the control circuitry indicative of a first motion value being available for reading;
   the control circuitry responsive to the third signal to initiate a read of a first motion value provided by the first motion measurement module and a read of a second motion value provided by the second motion measurement module.

83. A system for monitoring acceleration of an intra oral appliance, comprising:
   control circuitry operative in a first control circuitry low power sleep mode and a second control circuitry higher power normal operation mode;
   a first motion measurement module operative to provide a value representative of a first motion;
   wherein the first motion measurement module is operative to provide the value representative of the first motion value at a rate; and
   a second motion measurement module operative to provide a second motion value representative of a second motion;
   the first motion measurement module operative to send a first signal to the control circuitry responsive to the value representative of the first motion satisfying a criterion, the control circuitry responsive to the first signal to:
      invoke the second control circuitry mode and in the second control circuitry mode;
      invoke a read mode for reading values representative of a first motion from the first motion measurement module; and
   wherein the first motion measurement module is operative to provide the value representative of the first motion at the rate for the control circuitry to read values representative of the first motion from the first motion measurement module and read values representative of the second motion value from the second motion measurement module, for the control signal operative in the read mode.
84. A system according to clause 81, wherein the first signal is sent to the control circuitry at the rate responsive to the value representative of the first motion satisfying the criterion.
85. A system according to clause 81 or clause 84, wherein the control circuitry is operative in a low power mode pending receipt of the first signal from the first motion measurement module and invokes the read mode at a higher power than the low power mode responsive to receipt of the first signal.
86. A system according to any of clause 81 to clause 85, wherein the motion measurement module is operative such that the rate is sufficient for the control circuitry to read the value representative of the first motion value from the first motion measurement module and to read the value representative of the second motion value of the second motion measurement module within one cycle of the rate.
87. A system according to any of clause 80 to clause 86, wherein the control circuitry is operative to send a "go to sleep" signal to the second motion measurement module to invoke a low power mode following elapse of a pre-set time period.
88. A system according to clause 81 or any of clause 83 to clause 87, wherein the control circuitry is operative in the read mode for a second pre-set time period before ceasing the read mode.
89. A system according to clause 87 or clause 88, wherein the pre-set time period and the second time period are the same time period.
90. A system according to any of clause 80 to clause 89, wherein the predetermined criterion comprises the value representative of the first motion exceeding an acceleration threshold.
91. A system according to clause 90, wherein the acceleration threshold is in the range 3 g to 5 g, in particular the threshold is 5 g, where "g" is the acceleration due to gravity.
92. A system according to any of clause 80 to clause 91, wherein the predetermined criterion comprises the value representative of the first motion indicative of the first motion comprising increasing acceleration exceeding a threshold rate of increase.
93. A system according to clause 93, wherein the predetermined criterion comprises the increasing acceleration exceeding the threshold rate for the increasing acceleration traversing an acceleration threshold.
94. A system according to clause 93 dependent on clause 91, wherein the acceleration threshold traversed by the increasing acceleration is in the range 3 g-5 g, in particular 5 g.
95. A system according to any of clause 80 to clause 94, further comprising wireless communications circuitry operative in a low-power mode and responsive to the "wake" signal from the control circuitry to initiate a higher power communications mode in which the communications circuitry is operative to transmit and receive wireless communications.
96. A system according to any of clause 80 to clause 95, wherein the first motion value comprises respective component first motion values representative of a first motion measured for each of mutually orthogonal directions (X, Y, Z).
97. A system according to any of clause 80 to clause 96, wherein the second motion value comprises respective component values representative of a second motion measured for each of mutually orthogonal directions (X, Y, Z).
98. A system according to any of clause 80 to clause 97, wherein the first motion measurement module is operative to determine a first motion vector from the first motion measured for each of mutually orthogonal directions (X, Y, Z) and provide the first motion vector as the first motion value.
99. A system according to any of clause 80 to clause 97, wherein the first motion measurement module is operative to sample first motion values measured for each of mutually orthogonal directions (X, Y, Z) and provide the first motion values to the control circuitry.
100. A system according to any of clause 80 to clause 99, wherein the first motion is a linear motion.
101. A system according to clause 100, wherein the linear motion is linear acceleration and the first motion measurement module is a linear acceleration measurement module, in particular wherein the linear acceleration measurement module is an accelerometer.
102. A system according to any of clause 80 to clause 101, wherein the second motion is an angular motion measured around respective axes of rotation in mutually orthogonal directions (X', Y', Z').
103. A system according to clause 102, wherein the angular motion is angular velocity and the second motion measurement module is an angular velocity measurement module.
104. A method for monitoring acceleration of an intra oral appliance, comprising:
operating a first motion measurement module in a first mode to
provide a first motion value at a first rate and to send a first signal to control circuitry responsive to a first motion value criterion having been satisfied;
operating a second motion measurement module to provide a second motion value representative of a second motion;
operating the control circuitry to respond to the first signal by:
sending a second signal to the first motion measurement module to invoke a second mode to provide the first motion value at a second rate greater than or at least equal to the first rate: and
sending a "wake up" signal to the second motion measurement module to invoke a second motion measurement mode operative to provide the second motion value;
operating the first motion measurement module to send a third signal to the control circuitry indicative of a first motion value being available for reading; and
operating the control circuitry to initiate, responsive to the third signal, a read of a first motion value provided by the first motion measurement module and a read of a second motion value provided by the second motion measurement module.
105. A method for monitoring acceleration of an intra oral appliance, comprising:
operating a first motion measurement module to provide a value representative of a first motion at a rate;
operating a second motion measurement module to provide a second motion value representative of a second motion;

operating the first motion measurement module to send a first signal to control circuitry responsive to the value representative of the first motion satisfying a criterion;

operating the control circuitry to respond to the first signal by:

invoking a read mode for reading values representative of the first motion from the first motion measurement module; and sending a "wake up" signal to the second motion measurement module to invoke a second motion measurement mode operative to provide the second motion value; and operating the control circuitry to read values representative of the first motion from the first motion measurement module provided at the rate in the read mode and to read values representative of the second motion value from the second motion measurement module.

106. A method for monitoring acceleration of an intra oral appliance, comprising:

operating control circuitry in a first control circuitry low power sleep mode and in a second control circuitry higher power normal operation mode;

operating a first motion measurement module in a first mode to provide a first motion value at a first rate and to send a first signal to the control circuitry responsive to a first motion value criterion having been satisfied;

operating a second motion measurement module to provide a second motion value representative of a second motion;

further operating the control circuitry to respond to the first signal when in the first control circuitry mode by:

invoking the second control circuitry mode and when in the second control circuitry mode;

sending a second signal to the first motion measurement module to invoke a second mode to provide the first motion value at a second rate greater than or at least equal to the first rate: and sending a "wake up" signal to the second motion measurement module to invoke a second motion measurement mode operative to provide the second motion value;

operating the first motion measurement module to send a third signal to the control circuitry indicative of a first motion value being available for reading; and operating the control circuitry to initiate, responsive to the third signal, a read of a first motion value provided by the first motion measurement module and a read of a second motion value provided by the second motion measurement module.

107. A method for monitoring acceleration of an intra oral appliance, comprising:

operating control circuitry in a first control circuitry low power sleep mode and in a second control circuitry higher power normal operation mode;

operating a first motion measurement module to provide a value representative of a first motion at a rate;

operating a second motion measurement module to provide a second motion value representative of a second motion;

operating the first motion measurement module to send a first signal to control circuitry responsive to the value representative of the first motion satisfying a criterion;

operating the control circuitry in the first control circuitry mode to respond to the first signal by:

invoking the first control circuitry mode and in the first control circuitry mode;

invoking a read mode for reading values representative of the first motion from the first motion measurement module; and operating the control circuitry to read values representative of the first motion from the first motion measurement module provided at the rate in the read mode and to read values representative of the second motion value from the second motion measurement module.

108. A method according to clause 105, further comprising operating the first motion measurement module to send the second signal to the control circuitry at the rate responsive to the value representative of the first motion satisfying the criterion.

109. A method according to clause 105 or clause 108, further comprising operating the control circuitry in a low power mode pending receipt of the first signal from the first motion measurement module and invoking the read mode at a higher power than the low power mode responsive to receipt of the first signal.

110. A method according to any of clause 104 to clause 109, further comprising operating the motion measurement module such that the rate is sufficient for the control circuitry to read the value representative of the first motion value from the first motion measurement module and to read the value representative of the second motion value of the second motion measurement module within one cycle of the rate.

111. A method according to any of clause 102 to clause 110, further comprising operating the control circuitry to send a "go to sleep" signal to the second motion measurement module to invoke a low power mode following elapse of a pre-set time period.

112. A method according to clause 105 or any of clause 106 to clause 112, wherein the control circuitry is operative in the read mode for a second pre-set time period before ceasing the read mode.

113. A method according to clause 111 or clause 112, wherein the pre-set time period and the second time period are the same time period.

114. A method according to any of clause 104 to clause 113, further comprising operating the first motion measurement module to determine a first motion vector from the first motion measured for each of mutually orthogonal directions (X, Y, Z) and provide the first motion vector as the first motion value.

115. A method according to any of clause 104 to clause 114, further comprising operating the first motion measurement module to sample first motion values measured for each of mutually orthogonal directions (X, Y, Z) and provide the sampled first motion values to the control circuitry.

116. A method according to any of clause 104 to clause 115, wherein the first motion is a linear motion. in particular wherein the linear motion is linear acceleration.

117. A method according to any of clause 104 to clause 116, wherein the second motion is an angular motion measured around respective axes of rotation in mutually orthogonal directions (X', Y', Z').

118. A method according to clause 117, wherein the angular motion is angular velocity and the second motion measurement module is an angular velocity measurement module.

119. A system according to any of clause 80 to clause 103, wherein the intra oral appliance is removable, in particular wherein the intra oral appliance is a mouth guard.

120. A method according to any of clause 104 to clause 118, wherein the intra oral appliance is removable, in particular wherein the intra oral appliance is a mouth guard.

121. A system according any of clause 80 to clause 103 or clause 120, wherein the control circuitry is further operative to set a flag responsive to a first motion value satisfying a second criterion.

122. A system according to clause 121, wherein the control circuitry is further operative to unset the flag responsive to the first motion value not satisfying the second criterion.

123. A system according to clause 121 or clause 122, wherein the control circuitry is further operative to determine the flag as set or unset after a read of a first motion value and to make a subsequent read of the first motion value for determining the flag is set.

124. A system according to any of clause 121 to clause 123, wherein the control circuitry is further operative to determine the flag as set or unset after a pre-set number of first motion value read operations and to make subsequent reads of the first motion value for determining the flag is set.

125. A system according to any of clause 121 to clause 124, wherein the first motion value comprises one or more acceleration values.

126. A method according any of clause 104 to clause 118 or clause 120, comprising setting a flag responsive to the first motion value satisfying a second criterion.

127. A method according to clause 126, further comprising unsetting the flag responsive to the first motion value not satisfying the second criterion.

128. A method according to clause 126 or clause 127, further comprising determining the flag as set or unset after a read of a first motion value and making a subsequent read of the first motion value for determining the flag is set.

129. A method according to any of clause 126 to clause 128, further comprising determining the flag as set or unset after a pre-set number of first motion value read operations and making subsequent reads of the first motion value for determining the flag is set.

130. A system for monitoring acceleration of an intra oral appliance, the system comprising:
  a motion monitoring system operative to monitor acceleration experienced by the intra oral application and operative to communicate acceleration data to a monitoring station, the motion monitoring system comprising:
    a motion measurement module operative to provide data representative of a motion;
    a data packet compiler for compiling a data transmission comprising at least one data packet for transmission to a monitoring station;
    an incomplete transmission management module to retrieve at least one data packet from a storage device of said motion monitoring system responsive to notification, from a monitoring station, of an incomplete receipt of a data transmission;
  a power source for providing power to the motion monitoring system; and
  a power source monitoring system to monitor a power source operating parameter of said power source and to output data representative of a power source status based upon a monitored operating parameter of said power source.

131. A system according to clause 130, wherein said data packet compiler is operative to compile an impact data transmission comprising a plurality of data packets, each data packet comprising data representative of a part of said motion.

132. A system according to clause 130 or 132, wherein the power source monitoring system comprises power source monitoring circuitry and a power source monitoring module, said power source monitoring circuitry coupled to said power source and configured to output, to said power source monitoring module, a signal comprising a measured value of a parameter of said power source.

133. A system according to clause 132, wherein said power source monitoring module is operative to compare said measured value of said parameter of said power source to a threshold value.

134. A system according to clause 133, wherein responsive to a determination that said measured value is less than, or equal to, said threshold value, said power source monitoring module issues an instruction invoking an inactive state of said system.

135. A system according to clause 133 or 134, wherein responsive to a determination that said measured value is greater than said threshold value, said power source monitoring module issues an instruction invoking an active state of said system.

136. A system according to any of the preceding clauses, further comprising a status monitoring module operative to at least one of:
  monitor a status of a plurality of operating conditions and/or parameters of said motion monitoring system and forward data representative of said plurality of operating conditions and/or parameters to said data packet compiler; and
  retrieve historic impact data from a storage device of said motion monitoring system and forward said historic impact data to said data packet compiler.

137. A system according to clause 136, wherein said data packet compiler, responsive to receipt of: said data representative of said plurality of operating conditions and/or parameters; and/or said historic impact data, is operative to, or further operative to, create a status data packet containing: said data representative of said plurality of operating conditions and/or parameters; and/or said historic impact data, for transmission to a monitoring station.

138. A system according to clause 137, when dependent upon clause 6, wherein said status monitoring module and said data packet compiler, responsive to said instruction invoking said active state, create said status data packet on a periodic basis.

139. A system according to clause 138, wherein a status data packet is created and transmitted at a specific time period from creation and transmission of a previous status data packet.

140. A system according to clause 138, wherein a status data packet is created and transmitted at a specific time period from creation and transmission of a previous status data packet, unless a transmission comprising impact data has been created and transmitted responsive to measurement of an impact event during the specific period following the transmission of the previous status data packet, in which case said status data packet is created and transmitted at a specific time period from creation and transmission of said transmission comprising impact data.
141. A system according to clause 140, wherein said specific time period from creation and transmission of a previous status data packet and said specific time period from creation and transmission of said transmission comprising impact data are of a same duration.
142. A system according to clause 141, wherein said duration is ten seconds.
143. A system according to any of clauses 136 to 142, wherein said historic impact data comprises a number of impact events recorded by the motion monitoring system in a current session.
144. A system according to any of clauses 136 to 143, wherein said historic impact data comprises data representative of a maximum acceleration value reached during at least one previous impact event.
145. A system according to any one of clauses 136 to 144, wherein said data representative of said plurality of operating conditions and/or parameters comprises data representative of at least one of: a status of said power source; an identifier unique to the motion monitoring system; and a time period for which the motion monitoring system has been active.
146. A system according to clause 145, wherein said data representative of said status of said power source comprises data representative of at least one of: a power output level of said power source; a charge level of said power source; and a state-of-health of said power source.
147. A system according to any of clause 130 to clause 146, wherein said incomplete transmission management module is operative to retrieve at least one data packet from a storage device of said motion monitoring system responsive to notification, from a monitoring station, of an incomplete receipt of an impact data transmission.
148. A monitoring station for receiving a data transmission from a system according to any of the preceding clauses, the monitoring station comprising:
a received data packet monitor for determining if a data transmission received from said system is complete and/or comprises non-erroneous data;
an incomplete data notifier operative, responsive to a determination from said received data packet monitor that a received data transmission is incomplete and/or comprises erroneous data, to prepare a message, for transmission to said system, said message containing data identifying missing and/or erroneous data packets and a request for these data packets to be re-sent by the system;
a power source status alert module operative to, from data received in said data transmission, compare a value representative of a power source status of a power source of said system to a threshold value and, if said value is less than, or equal to, said threshold value, to initiate issue of an alert indicative of a sub-optimal status of said power source.
149. A monitoring station according to clause 148, further comprising a remaining charge assessment module operative to receive an indication from said power source status alert module that, in said comparison, said value is greater than said threshold value, and responsive thereto operative to determine a period of time for which the value is likely to exceed the threshold value.
150. A monitoring station according to clause 149, wherein said determination is based upon a comparison with a charge versus voltage graph or table for the battery.
151. A monitoring station according to clause 149 or 150, wherein said remaining charge assessment module is further operative to compare a value representative of said determined period of time to a value representative of a threshold period of time.
152. A monitoring station according to clause 151, wherein responsive to a determination that said value representative of said determined period of time is less than, or equal to, said value representative of a threshold period of time, said remaining charge assessment module operates to initiate issue of an alert indicative of impending low charge of said power source of said system.
153. An impact assessment system, comprising:
a system for monitoring acceleration of an intra oral appliance according to any of clauses 130 to 147; and
a monitoring station according to any of clauses 148 to 152.

What is claimed is:
1. An oral appliance for detecting acceleration experienced by a head of a wearer, the oral appliance being a mouth-guard comprising:
a body comprising a formation for extending around at least a portion of at least one of maxillary and mandibular teeth of the wearer and configured for location against at least a portion of at least one of maxillary and mandibular teeth at least at one of:
an anterior teeth region of a mouth of the wearer;
a posterior teeth region of the mouth of the wearer; and
a position between the anterior and posterior teeth regions of the mouth of the wearer;
a system configured to monitor acceleration experienced by the mouth-guard and operative to communicate acceleration data to a monitoring station;
a power source electrically coupled to the system configured to monitor acceleration and for providing power thereto;
wherein the power source is embedded within material of the body and is located within a region of the body that is locatable at the posterior teeth region of the mouth of the wearer, and further wherein the system configured to monitor acceleration is embedded within the material of the body and is located within a region of the body that is locatable at the posterior teeth region of the mouth of the wearer, and
wherein the system configured to monitor acceleration has an antenna that is located remote from the system and towards, or at, a region of the formation locatable against the anterior teeth region of the wearer, and wherein the antenna is embedded in a protective material of a first wall.
2. The oral appliance according to claim 1, wherein the formation comprises a trench in which at least one of maxillary and mandibular teeth of the wearer are locatable, the trench defined by:
the first wall configured to cover at least a portion of a vestibular surface of at least one of maxillary and mandibular teeth of the wearer;

a second wall configured to cover at least a portion of a palatal surface of at least one of maxillary and mandibular teeth of the wearer; and a third wall connecting the first and second walls and configured to cover at least a portion of incisal and occlusal surfaces of at least one of maxillary and mandibular teeth of the wearer.

3. The oral appliance according to claim 2, wherein the power source is embedded within material of the second wall.

4. The oral appliance according to claim 2, wherein the system configured to monitoring acceleration is embedded in material of the second wall.

5. The oral appliance according to claim 2, wherein the system configured to monitoring acceleration is embedded in material of the first wall.

6. The oral appliance according to claim 1, wherein the power source and/or the system configured to monitor acceleration are encapsulated in an inert material.

7. The oral appliance according to claim 6, wherein the inert material comprises parylene C.

8. The oral appliance according to claim 1, wherein the power source and/or the system configured to monitor acceleration are encapsulated in material of the body.

9. The oral appliance according to claim 1, wherein the system configured to monitor acceleration and the power source comprise separate discrete elements.

10. The oral appliance according to claim 9, wherein the system configured to monitor acceleration and the power source are electrically connected by a connection lead.

11. The oral appliance according to claim 10, wherein the connection lead comprises an antenna of the system configured to monitor acceleration.

12. The oral appliance according to claim 1,
wherein at least one of:
dimensions of components of the system configured to monitor acceleration;
dimensions of a circuit board upon which the system configured to monitor acceleration is disposed;
an arrangement and/or configuration of components of the system configured to monitor acceleration upon a circuit board upon which the system configured to monitor acceleration is disposed,
are optimized and/or reduced to reduce a volume and/or footprint of the system configured to monitor acceleration.

* * * * *